(12) United States Patent
Tang

(10) Patent No.: US 12,116,571 B2
(45) Date of Patent: *Oct. 15, 2024

(54) COMPOSITIONS AND METHODS FOR DETECTING NUCLEIC ACID REGIONS

(71) Applicant: LIFE TECHNOLOGIES CORPORATION, Carlsbad, CA (US)

(72) Inventor: Pei-Zhong Tang, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1174 days.

This patent is subject to a terminal disclaimer.

(21) Appl. No.: 16/864,445

(22) Filed: May 1, 2020

(65) Prior Publication Data

US 2020/0325471 A1 Oct. 15, 2020

Related U.S. Application Data

(63) Continuation of application No. 15/646,851, filed on Jul. 11, 2017, now Pat. No. 10,676,734.

(60) Provisional application No. 62/361,239, filed on Jul. 12, 2016.

(51) Int. Cl.
| | |
|---|---|
| *C12Q 1/6853* | (2018.01) |
| *C12N 15/10* | (2006.01) |
| *C12Q 1/6855* | (2018.01) |
| *C12Q 1/6858* | (2018.01) |

(52) U.S. Cl.
CPC ....... *C12N 15/1065* (2013.01); *C12Q 1/6853* (2013.01); *C12Q 1/6855* (2013.01); *C12Q 1/6858* (2013.01)

(58) Field of Classification Search
CPC .......... C12N 15/1065; C12N 15/907; C12Q 1/6853; C12Q 1/6855; C12Q 1/6858; C12Q 2535/122
See application file for complete search history.

(56) References Cited

U.S. PATENT DOCUMENTS

| | | | |
|---|---|---|---|
| 2013/0231253 A1 | 9/2013 | Amorese et al. | |
| 2014/0120529 A1 | 5/2014 | Andersen et al. | |
| 2015/0051116 A1 | 2/2015 | Kim et al. | |
| 2018/0016572 A1* | 1/2018 | Tang | C12Q 1/6853 |

FOREIGN PATENT DOCUMENTS

| | | |
|---|---|---|
| WO | WO-2015078631 A1 | 6/2015 |
| WO | WO-2015185427 A1 | 12/2015 |
| WO | WO-2015200378 A1 | 12/2015 |

OTHER PUBLICATIONS

Ahern, H. Biochemical, reagents kits offer scientists good return on investment. The Scientist, vol. 9, No. 10, p. 20, Jul. 24, 1995, printed as pp. 1/7-7/7. (Year: 1995).*

Hietpas et al. Fitness analyses of all possible point mutations for regions of genes in yeast. Nature Protocols, vol. 7, No. 7, pp. 1382-1396, Jun. 21, 2012. (Year: 2012).*

Agencourt® AMPure®. PCR Purification. Protocol 000601v0204, Beckman Coulter®, pp. 1-9; 2006. (Year: 2006).

Blow, N. "To edit or not: The NgAgo story", Bio Techniques, vol. 61, Oct. 2016, pp. 172-174.

Cox, et al., "Therapeutic genome editing: prospects and challenges", Nature Medicine. vol. 21, No. 2, Feb. 2015, 121-131.

Crosetto, et al., "Nucleotide-resolution DNA double-strand break mapping by next-generation sequencing", Nature Methods, vol. 10, No. 4, Apr. 2013, 361-368.

De Ravin, et al., "CRISPR-Cas9 gene repair of hematopoietic stem cells from patients with X-linked chronic granulomatous disease", Science Translational Medicine, vol. 9, Jan. 11, 2017, 1-10.

Digiusto, et al., "Preclinical development and qualification of ZFN-mediated CCR5 disruption in human hematopoietic stem/progenitor cells", Molecular Therapy—Methods & Clinical Development vol. 3, 2016, 1-12.

Frock, , "Genome-wide detection of DNA double-stranded breaks induced by engineered nucleases", Nature Biotechnology. vol. 33, No. 2, Feb. 2015, 179-187.

Fu, et al., "Improving CRISPR-Cas nuclease specificity using truncated guide RNAs", Nature Biotechnology. vol. 32, No. 3, Mar. 2014, 279-284.

Gabriel, et al., "An unbiased genome-wide analysis of zinc-finger nuclease specificity", Nature Biotechnology. vol. 29, No. 9, Sep. 2011, 816-824.

Gao, F. et al., "DNA-guided Genome Editing Using the Natronobacterium Gregoryi Argonaute", Nature Biotechnology, vol. 34, No. 7, 2017, pp. 768-773, including one page of Online Methods, originally published online May 2016, including one page of Addendum, and one page of Retraction, retracted on Aug. 2, 2017.

GenBank Accession No. KF184840.1, publicly available Jun. 2014, printed as pp. 1/42-42/42. (Year: 2014).

Guilinger, et al., "Fusion of catalytically inactive Cas9 to FokI nuclease improves the specificity of genome modification", Nature Biotechnology. vol. 32, 2014, 577-582.

Guo, et al., "Directed Evolution of an Enhanced and Highly Efficient FokI Cleavage Domain for Zinc Finger Nucleases", Journal of Molecular Biology, vol. 400, May 2010, 96-107.

Haapa S. et al. An efficient and accurate integration of mini-Mu transposons in vitro: a general methodology for functional genetic analysis and molecular biology applications, Nucleic Acids Research, 1999, 27:13, pp. 2777-2784.

Holt, et al., "Human hematopoietic stem/progenitor cells modified by zinc-finger nucleases targeted to CCR5 control HIV-1 in vivo", Nature Biotechnology. vol. 28, No. 8, Aug. 2010, 839-847.

Hultman, et. al. Direct solid phase sequencing of genomic and plasmid DNA using magnetic beads as solid support. Nucleic Acis Research, vol. 17, pp. 4937-4946. 1988.

(Continued)

*Primary Examiner* — Jennifer Dunston
(74) *Attorney, Agent, or Firm* — Stephen G. Whiteside

(57) ABSTRACT

Provided are methods, compositions, reagents, kits that are useful for detecting a specific nucleic acid region in genome with high efficiency and high sensitivity.

11 Claims, 5 Drawing Sheets

Specification includes a Sequence Listing.

(56) References Cited

OTHER PUBLICATIONS

Javidi-Parsijani, P. et al., "No Evidence of Genome Editing Activity from Natronobacterium Gregoryi Argonaute (NgAgo) in Human Cells", PLOS ONE, vol. 12, No. 5, e0177444, May 11, 2017, printed as pp. 1/14, 14/14.
Khin, N. et al., "No Evidence for Genome Editing in Mouse Zygotes and HEK293T Human Cell Line Using the DNA-guided Natronobacterium Gregoryi Argonaute (NgAgo)", PLOS ONE, vol. 12, No. 6, e0178768, Jun. 13, 2017, printed as pp. 1/10-10/10.
Kim, et al., "Digenome-seq: genome-wide profiling of CRISPR-Cas9 off-target effects in human cells", Nature Methods, vol. 12, No. 3, Mar. 2015, 237-243.
Kleinstiver, et al., "High-fidelity CRISPR-Cas9 nucleases with no detectable genome-wide off-target effects", Nature vol. 529, Jan. 28, 2016, 490-495.
Koo, et al., "Measuring and Reducing Off-Target Activities of Programmable Nucleases Including CRISPR-Cas9", Molecules and Cells vol. 38, No. 6, May 19, 2015,475-481.
Lee et al., "Failure to Detect DNA-guided Genome Editing Using Natronobacterium Gregoryi Argonaute", Nature Biotechnology, vol. 35, No. 1, Jan. 2017, pp. 17-18, published online Nov. 28, 2016, including pp. 1/24-24/24 of Supplementary Information.
Liang, X. et al., "Enhanced CRISPR/Cas9-mediated precise genome editing by improved design and delivery of gRNA, Cas9 nuclease, and donor DNA", Journal of Biotechnology, vol. 241, Nov. 11, 2016, 136-146.
Li, et al., "Genomic Editing of the HIV-1 Coreceptor CCR5 in Adult Hematopoietic Stem and Progenitor Cells Using Zinc Finger Nucleases", Molecular Therapy, vol. 21, No. 6, Jun. 2013, 1259-1269.
Illumina. Overview of Indexed Sequencing on the NextSeq, MiSeq, and Hi Seq Platforms. Part# 15057 455 Rev. B, pp. 1-14, Feb. 2015. (Year: 2015).
Mali, et al., "CAS9 transcriptional activator for target specificity screening and paired nickases for cooperative genome engineering", Nature Biotechnology, vol. 31, No. 9, Sep. 2013, 833-838.
Mandal, et al., "Efficient Ablation of Genes in Human Hematopoietic Stem and Effector Cells using CRISPR/Cas9", Cell Stem Cell, vol. 15, Nov. 6, 2014, 643-652.
Miller, et al., "An improved zinc-finger nuclease architecture for highly specific genome editing", Nature Biotechnology, vol. 25, No. 7, Jul. 2007, 778-785.
Mussolino, et al., "A novel TALE nuclease scaffold enables high genome editing activity in combination with low toxicity", Nucleic Acids Research, vol. 39, No. 21, Aug. 3, 2011, 9283-9293.
Ochiai, et al., "Single-Base Pair Genome Editing in Human Cells by Using Site-Specific Endonucleases", International Journal of Molecular Sciences, vol. 16, Sep. 3, 2015, 21128-21137.
O'Geen, H. et al., "Unexpected Binding Behaviors of Bacterial Argonautes in Human Cells Cast Doubts on their Use as Targetable Gene Regulators", PLOS ONE, vol. 13, No. 3, e0193818, Mar. 27, 2018, printed as pp. 1/12-12/12, including pp. 1/11-11/11 of Supplementary Information.
PCT/US2017/041525, "International Search Report mailed", Dec. 7, 2017,7 Pages.
Perez, et al., "Establishment of HIV-1 resistance in CD4+ T cells by genome editing using zinc-finger nucleases", Nature Biotechnology, vol. 26, No. 7, Jul. 2008,808-816.
Ran, et al., "Double Nicking by RNA-Guided CRISPR Cas9 for Enhanced Genome Editing Specificity", Cell vol. 154, Sep. 12, 2013, 1380-1389.
Richardson, C. et al., "Enhancing homology-directed genome editing by catalytically active and inactive CRISPR-Cas9 using asymmetric donor DNA", Nature Biotechnology, vol. 34, No. 3, Mar. 2016, 339-344.
Singh, et al., "A Mouse Geneticist's Practical Guide to CRISPR Applications", Genetics, vol. 199, Jan. 2015, 1-15.
Slaymaker, et al., "Rationally engineered Cas9 nucleases with improved specificity", Science vol. 351, Issue 6268, Dec. 1, 2015, 84-88.
Sorek, R. et al., "CRISPR-Mediated Adaptive Immune Systems in Bacteria and Archaea", Annual Review of Biochemistry, vol. 82, Mar. 2013, pp. 237-266.
Tebas, et al., "Gene Editing of CCR5 in Autologous CD4 T Cells of Person Infected with HIV", The New England Journal of Medicine vol. 370, No. 10, Mar. 6, 2014, 901-910.
Tsai et al., "GUIDE-seq enables genome-wide profiling of off-target cleavage by CRISPR-Cas nucleases", Nature Biotechnology, vol. 33, No. 2, pp. 187-197, Feb. 2015, published online Dec. 16, 2014, including p. 1/1 of Online Methods and pp. 1/38-38/38 of Supplementary Text and Figures.
Tsai, et al., "Dimeric CRISPR RNA-guided FokI nucleases for highly specific genome editing", Nature Biotechnology, vol. 32, 2014, 569-576.
Tsai, et al., "GUIDE-seq enables genome-wide profiling of off-target cleavage by CRISPR-Cas nucleases", Nature Biotechnology. vol. 33, No. 2, Dec. 16, 2014, 187-198.
Van Pelt-Verkuil et al. Principles and Technical Aspects of PCR Amplification. Springer, 2008, pp. i-xii, 1-323, and 1/6-6/6 of Color Plates. (Year: 2008).
Wang, Xiaoling et al., "Unbiased detection of off-target cleavage by CRISPR-Cas9 and TALENs using integrase-defective lentiviral vectors", Nature Biotechnology, vol. 33, No. 2, Feb. 2015, 175-179.
Xu, Xiaojun et al., "CRISPR-Cas9 cleavage efficiency correlates strongly with target-sgRNA folding stability: from physical mechanism to off-target assessment", Scientific Reports, 7:143 DOI: 1 0.1 038/s41598-017 -00180-1, Mar. 10, 2017, 1-9.
Ye, Lin et al., "Seamless modification of wild-type induced pluripotent stem cells to the natural CCR5Delta32 mutation confers resistance to HIV infection", Proceedings National Academy of Science, vol. 111, No. 26, Jul. 1, 2014, 9591-9596.
Yoshimi, et al., "Allele-specific genome editing and correction of disease-associated phenotypes in rats using the CRISPR-Cas platform", Nature Communications, vol. 5, Jun. 26, 2014,4240.

* cited by examiner

SEQUENCE LISTING

<160> NUMBER OF SEQ ID NOS: 243

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ccactacgcc tccgctttcc tctctatggg cagtcggtga                40

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcaccgactg cccatagaga ggacc                                25

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccactacgcc tccgctttcc tctctatggg cagtcggtga tttcgtgcgt cagttca     57

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caagcagaag acggcatacg agattcgcct tagtgactgg agtcctctct atgggcagtc    60
ggtga                                                                65

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caagcagaag acggcatacg agatctagta cggtgactgg agtcctctct atgggcagtc    60
ggtga                                                                65

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caagcagaag acggcatacg agatttctgc ctgtgactgg agtcctctct atgggcagtc    60
ggtga                                                                65

<210> SEQ ID NO 7

-continued

```
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caagcagaag acggcatacg agatgctcag gagtgactgg agtcctctct atgggcagtc    60
ggtga                                                                65

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caagcagaag acggcatacg agataggagt ccgtgactgg agtcctctct atgggcagtc    60
ggtga                                                                65

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caagcagaag acggcatacg agatcatgcc tagtgactgg agtcctctct atgggcagtc    60
ggtga                                                                65

<210> SEQ ID NO 10
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caagcagaag acggcatacg agatgtagag aggtgactgg agtcctctct atgggcagtc    60
ggtga                                                                65

<210> SEQ ID NO 11
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caagcagaag acggcatacg agatcctctc tggtgactgg agtcctctct atgggcagtc    60
ggtga                                                                65

<210> SEQ ID NO 12
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 12
aatgatacgg cgaccaccga gatcta                                              26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aatgatacgg cgaccaccga gatctacac                                           29

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gatcggaaga gcca                                                           14

<210> SEQ ID NO 15
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 15
aatgatacgg cgaccaccga gatctacact agatcgcnnw nnwnnacact ctttccctac         60
acgacgctct tccgatc                                                        77

<210> SEQ ID NO 16
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
```

<223> OTHER INFORMATION: a, c, t, g, unknown or other

<400> SEQUENCE: 16
aatgatacgg cgaccaccga gatctacacc tctctatnnw nnwnnacact ctttccctac    60
acgacgctct tccgatct                                                 78

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 17
aatgatacgg cgaccaccga gatctacact atcctctnnw nnwnnacact ctttccctac    60
acgacgctct tccgatct                                                 78

<210> SEQ ID NO 18
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 18
aatgatacgg cgaccaccga gatctacaca gagtagannw nnwnnacact ctttccctac    60
acgacgctct tccgatct                                                 78

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:

```
<221> NAME/KEY: modified_base
<222> LOCATION: (44)..(45)
<223> OTHER INFORMATION: a, c, t, g, unknown or other

<400> SEQUENCE: 19
aatgatacgg cgaccaccga gatctacacg taaggagnnw nnwnnacact ctttccctac    60
acgacgctct tccgatct                                                  78

<210> SEQ ID NO 20
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 20
aatgatacgg cgaccaccga gatctacaca ctgcatannw nnwnnacact ctttccctac    60
acgacgctct tccgatct                                                  78

<210> SEQ ID NO 21
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 21
aatgatacgg cgaccaccga gatctacaca aggagtannw nnwnnacact ctttccctac    60
acgacgctct tccgatct                                                  78

<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
```

```
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 22
aatgatacgg cgaccaccga gatctacacc taagcctnnw nnwnnacact ctttccctac    60
acgacgctct tccgatct                                                 78

<210> SEQ ID NO 23
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 23
aatgatacgg cgaccaccga gatctacacg acattgtnnw nnwnnacact ctttccctac    60
acgacgctct tccgatct                                                 78

<210> SEQ ID NO 24
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 24
aatgatacgg cgaccaccga gatctacaca ctgatggnnw nnwnnacact ctttccctac    60
acgacgctct tccgatct                                                 78

<210> SEQ ID NO 25
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
```

```
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 25
aatgatacgg cgaccaccga gatctacacg tacctagnnw nnwnnacact ctttccctac    60
acgacgctct tccgatct                                                  78

<210> SEQ ID NO 26
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 26
aatgatacgg cgaccaccga gatctacacc agagctannw nnwnnacact ctttccctac    60
acgacgctct tccgatct                                                  78

<210> SEQ ID NO 27
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 27
aatgatacgg cgaccaccga gatctacacc atagtgannw nnwnnacact ctttccctac    60
acgacgctct tccgatct                                                  78

<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
```

```
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 28
aatgatacgg cgaccaccga gatctacact acctagtnnw nnwnnacact ctttccctac      60
acgacgctct tccgatct                                                   78

<210> SEQ ID NO 29
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 29
aatgatacgg cgaccaccga gatctacacc gcgatatnnw nnwnnacact ctttccctac      60
acgacgctct tccgatct                                                   78

<210> SEQ ID NO 30
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other

<400> SEQUENCE: 30
aatgatacgg cgaccaccga gatctacact ggattgtnnw nnwnnacact ctttccctac      60
acgacgctct tccgatct                                                   78

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (30)..(39)
<223> OTHER INFORMATION: a, c, t, g, unknown or other

<400> SEQUENCE: 31
catctcatcc ctgcgtgtct ccgactcagn nnnnnnnnng at                    42

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atcgttacct tagctgagtc ggagacacgc                                  30

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccactacgcc tccgctttcc tctctatggg cagtcggtga                       40

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcaccgactg cccatagaga ggacc                                       25

<210> SEQ ID NO 35
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccactacgcc tccgctttcc tctctatggg cagtcggtga tttcgtgcgt cagttca    57

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccactacgcc tccgctttcc tctctatg                                    28

<210> SEQ ID NO 37
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 37
gtttaattga gttgtcatat gttaat                                              26

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ataccgttat taacatatga caactc                                              26

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gttgtcatat gttaataacg gtat                                                24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
taacatatga caactcaatt aaac                                                24

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(40)
<223> OTHER INFORMATION: a, c, t, g, unknown or other

<400> SEQUENCE: 41
ccatctcatc cctgcgtgtc tccgactcag nnnnnnnnnn gat                           43

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atcgttacct tagctgagtc ggagacacgc                                          30

<210> SEQ ID NO 43
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gggaaaagat gg                                                         12

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccactacgcc tccgctttcc tctctatg                                        28

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccatcttttc cc                                                         12

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other

<400> SEQUENCE: 46 nnnnnnnnnn                                                            10

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttaattgagt tgtcatatgt taataacgg                                       29

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
accgttatta acatatgaca actcaatta                                       29
```

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccactacgcc tccgctttcc tctctatggg cagtcggtga                              40

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcaccgactg cccatagaga ggacc                                              25

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccactacgcc tccgctttcc tctctatg                                           28

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtttaattga gttgtcatat gttaat                                             26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ataccgttat taacatatga caactc                                             26

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gttgtcatat gttaataacg gtat                                               24

-continued

```
<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
taacatatga caactcaatt aaac                                             24

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(40)
<223> OTHER INFORMATION: a, c, t, g, unknown or other

<400> SEQUENCE: 56
ccatctcatc cctgcgtgtc tccgactcag nnnnnnnnnn gat                        43

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atcgttacct tagctgagtc ggagacacgc                                       30

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gggaaaagat gg                                                          12

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccactacgcc tccgctttcc tctctatg                                         28

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
```
ccatcttttc cc                                                         12

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggaaagacc cagcatccgt ggg                                             23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggcactgcgg ctggaggtgg ggg                                             23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggtgggggg agtttgctcc tgg                                             23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ggtgagtgag tgtgtgcgtg tgg                                             23

<210> SEQ ID NO 65
<211> LENGTH: 20
<212> TYPE: DNA
<213> ORGANISM: Homo sapiens

<400> SEQUENCE: 65
ggcactgcgg ctggaggtgg                                                 20

<210> SEQ ID NO 66
<211> LENGTH: 20
<212> TYPE: DNA
<213> ORGANISM: Homo sapiens

<400> SEQUENCE: 66
tgcactgcgg ccggaggagg                                                 20

<210> SEQ ID NO 67
<211> LENGTH: 20
<212> TYPE: DNA
<213> ORGANISM: Homo sapiens

```
<400> SEQUENCE: 67
ggctctgcgg ctggaggggg                                          20

<210> SEQ ID NO 68
<211> LENGTH: 20
<212> TYPE: DNA
<213> ORGANISM: Homo sapiens

<400> SEQUENCE: 68
ggcacgacgg ctggaggtgg                                          20

<210> SEQ ID NO 69
<211> LENGTH: 20
<212> TYPE: DNA
<213> ORGANISM: Homo sapiens

<400> SEQUENCE: 69
ggcatcacgg ctggaggtgg                                          20

<210> SEQ ID NO 70
<211> LENGTH: 20
<212> TYPE: DNA
<213> ORGANISM: Homo sapiens

<400> SEQUENCE: 70
ggcgctgcgg cgggaggtgg                                          20

<210> SEQ ID NO 71
<211> LENGTH: 20
<212> TYPE: DNA
<213> ORGANISM: Homo sapiens

<400> SEQUENCE: 71
ggcactgaga ctggggtgg                                           20

<210> SEQ ID NO 72
<211> LENGTH: 20
<212> TYPE: DNA
<213> ORGANISM: Homo sapiens

<400> SEQUENCE: 72
agcagtgcgg ctagaggtgg                                          20

<210> SEQ ID NO 73
<211> LENGTH: 20
<212> TYPE: DNA
<213> ORGANISM: Homo sapiens

<400> SEQUENCE: 73
ggcactgctg ctggggtgg                                           20

<210> SEQ ID NO 74
<211> LENGTH: 20
<212> TYPE: DNA
<213> ORGANISM: Homo sapiens

<400> SEQUENCE: 74
ggcactgggg ctggggagg                                           20

<210> SEQ ID NO 75
<211> LENGTH: 20
<212> TYPE: DNA
```

-continued

<213> ORGANISM: Homo sapiens

<400> SEQUENCE: 75
ggcactgggg ttggaggtgg                                               20

<210> SEQ ID NO 76
<211> LENGTH: 20
<212> TYPE: DNA
<213> ORGANISM: Homo sapiens

<400> SEQUENCE: 76
aggactgcgg ctggggtgg                                                20

<210> SEQ ID NO 77
<211> LENGTH: 20
<212> TYPE: DNA
<213> ORGANISM: Homo sapiens

<400> SEQUENCE: 77
ggcactgagg gtggaggtgg                                               20

<210> SEQ ID NO 78
<211> LENGTH: 20
<212> TYPE: DNA
<213> ORGANISM: Homo sapiens

<400> SEQUENCE: 78
gacaccacgg ctggagatgg                                               20

<210> SEQ ID NO 79
<211> LENGTH: 20
<212> TYPE: DNA
<213> ORGANISM: Homo sapiens

<400> SEQUENCE: 79
ggcactgtgg ctgcaggtgg                                               20

<210> SEQ ID NO 80
<211> LENGTH: 20
<212> TYPE: DNA
<213> ORGANISM: Homo sapiens

<400> SEQUENCE: 80
agcactgtgg ctggggagg                                                20

<210> SEQ ID NO 81
<211> LENGTH: 20
<212> TYPE: DNA
<213> ORGANISM: Homo sapiens

<400> SEQUENCE: 81
ggcaatgtgg ctgaaggtgg                                               20

<210> SEQ ID NO 82
<211> LENGTH: 20
<212> TYPE: DNA
<213> ORGANISM: Homo sapiens

<400> SEQUENCE: 82
ggcacagcag ctggaggtgc                                               20

<210> SEQ ID NO 83
<211> LENGTH: 20

```
<212> TYPE: DNA
<213> ORGANISM: Homo sapiens

<400> SEQUENCE: 83
gccactgggg ctggggtgg                                                    20

<210> SEQ ID NO 84
<211> LENGTH: 20
<212> TYPE: DNA
<213> ORGANISM: Homo sapiens

<400> SEQUENCE: 84
tgcactgtgg ctggagatgg                                                   20

<210> SEQ ID NO 85
<211> LENGTH: 20
<212> TYPE: DNA
<213> ORGANISM: Homo sapiens

<400> SEQUENCE: 85
ggctctgtgg ctggaggagg                                                   20

<210> SEQ ID NO 86
<211> LENGTH: 20
<212> TYPE: DNA
<213> ORGANISM: Homo sapiens

<400> SEQUENCE: 86
ggcactgcag ctagaggtgg                                                   20

<210> SEQ ID NO 87
<211> LENGTH: 20
<212> TYPE: DNA
<213> ORGANISM: Homo sapiens

<400> SEQUENCE: 87
ggcactgcgg gtggaggcgg                                                   20

<210> SEQ ID NO 88
<211> LENGTH: 20
<212> TYPE: DNA
<213> ORGANISM: Homo sapiens

<400> SEQUENCE: 88
agcactgtgc ctggggtgg                                                    20

<210> SEQ ID NO 89
<211> LENGTH: 20
<212> TYPE: DNA
<213> ORGANISM: Homo sapiens

<400> SEQUENCE: 89
ggcaatgcgg ctggaggcgg                                                   20

<210> SEQ ID NO 90
<211> LENGTH: 20
<212> TYPE: DNA
<213> ORGANISM: Homo sapiens

<400> SEQUENCE: 90
gaggctgcgg ctggggtgg                                                    20

<210> SEQ ID NO 91
```

```
<211> LENGTH: 20
<212> TYPE: DNA
<213> ORGANISM: Homo sapiens

<400> SEQUENCE: 91
ggctccgcag ctggaggtgg                                               20

<210> SEQ ID NO 92
<211> LENGTH: 20
<212> TYPE: DNA
<213> ORGANISM: Homo sapiens

<400> SEQUENCE: 92
agcactgtgg ctggggagg                                                20

<210> SEQ ID NO 93
<211> LENGTH: 20
<212> TYPE: DNA
<213> ORGANISM: Homo sapiens

<400> SEQUENCE: 93
gtcactgcag ctggaggagg                                               20

<210> SEQ ID NO 94
<211> LENGTH: 20
<212> TYPE: DNA
<213> ORGANISM: Homo sapiens

<400> SEQUENCE: 94
ggctctgagg ccagaggtgg                                               20

<210> SEQ ID NO 95
<211> LENGTH: 20
<212> TYPE: DNA
<213> ORGANISM: Homo sapiens

<400> SEQUENCE: 95
agcactgcag ctgggagtgg                                               20

<210> SEQ ID NO 96
<211> LENGTH: 20
<212> TYPE: DNA
<213> ORGANISM: Homo sapiens

<400> SEQUENCE: 96
gggactgcgg ctggaggtgg                                               20

<210> SEQ ID NO 97
<211> LENGTH: 20
<212> TYPE: DNA
<213> ORGANISM: Homo sapiens

<400> SEQUENCE: 97
ggcactgctg ctagaggtgc                                               20

<210> SEQ ID NO 98
<211> LENGTH: 20
<212> TYPE: DNA
<213> ORGANISM: Homo sapiens

<400> SEQUENCE: 98
ggctgtgcgg ccagaggtgg                                               20
```

```
<210> SEQ ID NO 99
<211> LENGTH: 20
<212> TYPE: DNA
<213> ORGANISM: Homo sapiens

<400> SEQUENCE: 99
gacactgagg caggaggtgg                                               20

<210> SEQ ID NO 100
<211> LENGTH: 20
<212> TYPE: DNA
<213> ORGANISM: Homo sapiens

<400> SEQUENCE: 100
ggcacaatgg ctggaggtga                                               20

<210> SEQ ID NO 101
<211> LENGTH: 20
<212> TYPE: DNA
<213> ORGANISM: Homo sapiens

<400> SEQUENCE: 101
ggcactgcca ctggggtga                                                20

<210> SEQ ID NO 102
<211> LENGTH: 20
<212> TYPE: DNA
<213> ORGANISM: Homo sapiens

<400> SEQUENCE: 102
cacactgcgg atggaggtgg                                               20

<210> SEQ ID NO 103
<211> LENGTH: 20
<212> TYPE: DNA
<213> ORGANISM: Homo sapiens

<400> SEQUENCE: 103
agcactgcag atggaggagg                                               20

<210> SEQ ID NO 104
<211> LENGTH: 20
<212> TYPE: DNA
<213> ORGANISM: Homo sapiens

<400> SEQUENCE: 104
gccactgcga ctggaggagg                                               20

<210> SEQ ID NO 105
<211> LENGTH: 20
<212> TYPE: DNA
<213> ORGANISM: Homo sapiens

<400> SEQUENCE: 105
ggcgctgcgg ccggaggtgg                                               20

<210> SEQ ID NO 106
<211> LENGTH: 20
<212> TYPE: DNA
<213> ORGANISM: Homo sapiens

<400> SEQUENCE: 106
cccactgggg ctggaggtgg                                               20
```

```
<210> SEQ ID NO 107
<211> LENGTH: 20
<212> TYPE: DNA
<213> ORGANISM: Homo sapiens

<400> SEQUENCE: 107
ggcactgggg caggagatgg                                               20

<210> SEQ ID NO 108
<211> LENGTH: 20
<212> TYPE: DNA
<213> ORGANISM: Homo sapiens

<400> SEQUENCE: 108
gtcactgcgg ctgcagatgg                                               20

<210> SEQ ID NO 109
<211> LENGTH: 20
<212> TYPE: DNA
<213> ORGANISM: Homo sapiens

<400> SEQUENCE: 109
ggctcttcgg ctggaggtag                                               20

<210> SEQ ID NO 110
<211> LENGTH: 20
<212> TYPE: DNA
<213> ORGANISM: Homo sapiens

<400> SEQUENCE: 110
tggactgcgg ctggagaggg                                               20

<210> SEQ ID NO 111
<211> LENGTH: 20
<212> TYPE: DNA
<213> ORGANISM: Homo sapiens

<400> SEQUENCE: 111
ggtacagcgg ctgggggagg                                               20

<210> SEQ ID NO 112
<211> LENGTH: 20
<212> TYPE: DNA
<213> ORGANISM: Homo sapiens

<400> SEQUENCE: 112
ggcaccgcgg ccggagctgt                                               20

<210> SEQ ID NO 113
<211> LENGTH: 20
<212> TYPE: DNA
<213> ORGANISM: Homo sapiens

<400> SEQUENCE: 113
ggcacagcag gtggaggtgg                                               20

<210> SEQ ID NO 114
<211> LENGTH: 20
<212> TYPE: DNA
<213> ORGANISM: Homo sapiens

<400> SEQUENCE: 114
agcactgtag caagaggtgg                                               20
```

<210> SEQ ID NO 115
<211> LENGTH: 20
<212> TYPE: DNA
<213> ORGANISM: Homo sapiens

<400> SEQUENCE: 115
ggcgctgcgg ctggagccgg                                                 20

<210> SEQ ID NO 116
<211> LENGTH: 20
<212> TYPE: DNA
<213> ORGANISM: Homo sapiens

<400> SEQUENCE: 116
cagactgcgg caggggtgg                                                  20

<210> SEQ ID NO 117
<211> LENGTH: 20
<212> TYPE: DNA
<213> ORGANISM: Homo sapiens

<400> SEQUENCE: 117
gtaactgcgg ctggcggtgg                                                 20

<210> SEQ ID NO 118
<211> LENGTH: 20
<212> TYPE: DNA
<213> ORGANISM: Homo sapiens

<400> SEQUENCE: 118
ggggctgcgg ccggaggtgg                                                 20

<210> SEQ ID NO 119
<211> LENGTH: 20
<212> TYPE: DNA
<213> ORGANISM: Homo sapiens

<400> SEQUENCE: 119
ggcactgtgg caagaggtgg                                                 20

<210> SEQ ID NO 120
<211> LENGTH: 20
<212> TYPE: DNA
<213> ORGANISM: Homo sapiens

<400> SEQUENCE: 120
ggcactgcgg gaggaggtgg                                                 20

<210> SEQ ID NO 121
<211> LENGTH: 20
<212> TYPE: DNA
<213> ORGANISM: Homo sapiens

<400> SEQUENCE: 121
ggaacggcgg ccggaggtgt                                                 20

<210> SEQ ID NO 122
<211> LENGTH: 20
<212> TYPE: DNA
<213> ORGANISM: Homo sapiens

<400> SEQUENCE: 122

| | |
|---|---|
| ggcactgggg ctggagacgg | 20 |

<210> SEQ ID NO 123
<211> LENGTH: 20
<212> TYPE: DNA
<213> ORGANISM: Homo sapiens

<400> SEQUENCE: 123

| | |
|---|---|
| agcactgggg ccagaggtga | 20 |

<210> SEQ ID NO 124
<211> LENGTH: 20
<212> TYPE: DNA
<213> ORGANISM: Homo sapiens

<400> SEQUENCE: 124

| | |
|---|---|
| ggcaccgagg ccggaggtgc | 20 |

<210> SEQ ID NO 125
<211> LENGTH: 20
<212> TYPE: DNA
<213> ORGANISM: Homo sapiens

<400> SEQUENCE: 125

| | |
|---|---|
| agcaccatgg ctagaggtgt | 20 |

<210> SEQ ID NO 126
<211> LENGTH: 20
<212> TYPE: DNA
<213> ORGANISM: Homo sapiens

<400> SEQUENCE: 126

| | |
|---|---|
| ggcactgagg ctgcaggcgg | 20 |

<210> SEQ ID NO 127
<211> LENGTH: 19
<212> TYPE: DNA
<213> ORGANISM: Homo sapiens

<400> SEQUENCE: 127

| | |
|---|---|
| ggcacgcggc tggaggagg | 19 |

<210> SEQ ID NO 128
<211> LENGTH: 20
<212> TYPE: DNA
<213> ORGANISM: Homo sapiens

<400> SEQUENCE: 128

| | |
|---|---|
| gggcatgcgg ctggaagtgg | 20 |

<210> SEQ ID NO 129
<211> LENGTH: 20
<212> TYPE: DNA
<213> ORGANISM: Homo sapiens

<400> SEQUENCE: 129

| | |
|---|---|
| ggaactgagg ctagagggggg | 20 |

<210> SEQ ID NO 130
<211> LENGTH: 19
<212> TYPE: DNA
<213> ORGANISM: Homo sapiens

<400> SEQUENCE: 130
ggcactgggc tggaggcgg                                                19

<210> SEQ ID NO 131
<211> LENGTH: 19
<212> TYPE: DNA
<213> ORGANISM: Homo sapiens

<400> SEQUENCE: 131
ggcaggcggc tggaggtgg                                                19

<210> SEQ ID NO 132
<211> LENGTH: 20
<212> TYPE: DNA
<213> ORGANISM: Homo sapiens

<400> SEQUENCE: 132
ggctatacgg caggtggtgg                                               20

<210> SEQ ID NO 133
<211> LENGTH: 20
<212> TYPE: DNA
<213> ORGANISM: Homo sapiens

<400> SEQUENCE: 133
ggcagtgagg ctggaaggga                                               20

<210> SEQ ID NO 134
<211> LENGTH: 20
<212> TYPE: DNA
<213> ORGANISM: Homo sapiens

<400> SEQUENCE: 134
gacacagagg cgagaggagg                                               20

<210> SEQ ID NO 135
<211> LENGTH: 20
<212> TYPE: DNA
<213> ORGANISM: Homo sapiens

<400> SEQUENCE: 135
ggcattaatg ctggcggggg                                               20

<210> SEQ ID NO 136
<211> LENGTH: 20
<212> TYPE: DNA
<213> ORGANISM: Homo sapiens

<400> SEQUENCE: 136
ggcagggagg agggaggagg                                               20

<210> SEQ ID NO 137
<211> LENGTH: 19
<212> TYPE: DNA
<213> ORGANISM: Homo sapiens

<400> SEQUENCE: 137
ggcagggcgg ccgaggtgg                                                19

<210> SEQ ID NO 138
<211> LENGTH: 19
<212> TYPE: DNA
<213> ORGANISM: Homo sapiens

```
<400> SEQUENCE: 138
ggcactgggg aggaggtgg                                                19

<210> SEQ ID NO 139
<211> LENGTH: 20
<212> TYPE: DNA
<213> ORGANISM: Homo sapiens

<400> SEQUENCE: 139
ggcaatgcga cgggaggtgg                                               20

<210> SEQ ID NO 140
<211> LENGTH: 20
<212> TYPE: DNA
<213> ORGANISM: Homo sapiens

<400> SEQUENCE: 140
gccccggggg gtgggggtgg                                               20

<210> SEQ ID NO 141
<211> LENGTH: 20
<212> TYPE: DNA
<213> ORGANISM: Homo sapiens

<400> SEQUENCE: 141
ggagctgtgg ccgggcgtgg                                               20

<210> SEQ ID NO 142
<211> LENGTH: 20
<212> TYPE: DNA
<213> ORGANISM: Homo sapiens

<400> SEQUENCE: 142
ggcagtgggg cagggcttgg                                               20

<210> SEQ ID NO 143
<211> LENGTH: 19
<212> TYPE: DNA
<213> ORGANISM: Homo sapiens

<400> SEQUENCE: 143
ggccctgcgg cggcggcgg                                                19

<210> SEQ ID NO 144
<211> LENGTH: 20
<212> TYPE: DNA
<213> ORGANISM: Homo sapiens

<400> SEQUENCE: 144
agcagtgagc ctggagcagg                                               20

<210> SEQ ID NO 145
<211> LENGTH: 19
<212> TYPE: DNA
<213> ORGANISM: Homo sapiens

<400> SEQUENCE: 145
agctctgcgc tggaggagg                                                19

<210> SEQ ID NO 146
<211> LENGTH: 20
<212> TYPE: DNA
<213> ORGANISM: Homo sapiens
```

```
<400> SEQUENCE: 146
accactcggg gtggggtgg                                            20

<210> SEQ ID NO 147
<211> LENGTH: 21
<212> TYPE: DNA
<213> ORGANISM: Homo sapiens

<400> SEQUENCE: 147
ggctctgtgg atagaggtgg a                                         21

<210> SEQ ID NO 148
<211> LENGTH: 19
<212> TYPE: DNA
<213> ORGANISM: Homo sapiens

<400> SEQUENCE: 148
gacactgctt tggagatgg                                            19

<210> SEQ ID NO 149
<211> LENGTH: 19
<212> TYPE: DNA
<213> ORGANISM: Homo sapiens

<400> SEQUENCE: 149
ggcctgggcc tggagtggg                                            19

<210> SEQ ID NO 150
<211> LENGTH: 20
<212> TYPE: DNA
<213> ORGANISM: Homo sapiens

<400> SEQUENCE: 150
ttcagtaggg ctggagtggg                                           20

<210> SEQ ID NO 151
<211> LENGTH: 19
<212> TYPE: DNA
<213> ORGANISM: Homo sapiens

<400> SEQUENCE: 151
ggcactgtgc tggggtgg                                             19

<210> SEQ ID NO 152
<211> LENGTH: 20
<212> TYPE: DNA
<213> ORGANISM: Homo sapiens

<400> SEQUENCE: 152
accatttcgg ctggacgcgg                                           20

<210> SEQ ID NO 153
<211> LENGTH: 19
<212> TYPE: DNA
<213> ORGANISM: Homo sapiens

<400> SEQUENCE: 153
ggcatcaggc tggtcgtgg                                            19

<210> SEQ ID NO 154
<211> LENGTH: 19
<212> TYPE: DNA
```

```
<213> ORGANISM: Homo sapiens

<400> SEQUENCE: 154
ggctctgggc tggtactgg                                            19

<210> SEQ ID NO 155
<211> LENGTH: 20
<212> TYPE: DNA
<213> ORGANISM: Homo sapiens

<400> SEQUENCE: 155
tacactctgg ctggcgaggg                                           20

<210> SEQ ID NO 156
<211> LENGTH: 20
<212> TYPE: DNA
<213> ORGANISM: Homo sapiens

<400> SEQUENCE: 156
ttccctgccc caggaggtcg                                           20

<210> SEQ ID NO 157
<211> LENGTH: 20
<212> TYPE: DNA
<213> ORGANISM: Homo sapiens

<400> SEQUENCE: 157
aaccctgcgg ggggggggg                                            20

<210> SEQ ID NO 158
<211> LENGTH: 20
<212> TYPE: DNA
<213> ORGANISM: Homo sapiens

<400> SEQUENCE: 158
cacactgggg cctgttgtgg                                           20

<210> SEQ ID NO 159
<211> LENGTH: 20
<212> TYPE: DNA
<213> ORGANISM: Homo sapiens

<400> SEQUENCE: 159
gagacggcgg cggggggggg                                           20

<210> SEQ ID NO 160
<211> LENGTH: 18
<212> TYPE: DNA
<213> ORGANISM: Homo sapiens

<400> SEQUENCE: 160
ggcagtgggg tggggtgg                                             18

<210> SEQ ID NO 161
<211> LENGTH: 20
<212> TYPE: DNA
<213> ORGANISM: Homo sapiens

<400> SEQUENCE: 161
ggcactgcgg ctggaggtgg                                           20

<210> SEQ ID NO 162
<211> LENGTH: 20
```

```
<212> TYPE: DNA
<213> ORGANISM: Homo sapiens

<400> SEQUENCE: 162
ggcacgacgg ctggaggtgg                                              20

<210> SEQ ID NO 163
<211> LENGTH: 20
<212> TYPE: DNA
<213> ORGANISM: Homo sapiens

<400> SEQUENCE: 163
aggactgcgg ctggggtgg                                               20

<210> SEQ ID NO 164
<211> LENGTH: 20
<212> TYPE: DNA
<213> ORGANISM: Homo sapiens

<400> SEQUENCE: 164
ggcaatgcgg ctggaggcgg                                              20

<210> SEQ ID NO 165
<211> LENGTH: 20
<212> TYPE: DNA
<213> ORGANISM: Homo sapiens

<400> SEQUENCE: 165
ggcactgaga ctggggtgg                                               20

<210> SEQ ID NO 166
<211> LENGTH: 20
<212> TYPE: DNA
<213> ORGANISM: Homo sapiens

<400> SEQUENCE: 166
tgcactgcgg ccggaggagg                                              20

<210> SEQ ID NO 167
<211> LENGTH: 20
<212> TYPE: DNA
<213> ORGANISM: Homo sapiens

<400> SEQUENCE: 167
ggctctgcgg ctggaggggg                                              20

<210> SEQ ID NO 168
<211> LENGTH: 20
<212> TYPE: DNA
<213> ORGANISM: Homo sapiens

<400> SEQUENCE: 168
ggcactgctg ctggggtgg                                               20

<210> SEQ ID NO 169
<211> LENGTH: 20
<212> TYPE: DNA
<213> ORGANISM: Homo sapiens

<400> SEQUENCE: 169
ggcactgtgg ctgcaggtgg                                              20

<210> SEQ ID NO 170
```

```
<211> LENGTH: 20
<212> TYPE: DNA
<213> ORGANISM: Homo sapiens

<400> SEQUENCE: 170
agcagtgcgg ctagaggtgg                                               20

<210> SEQ ID NO 171
<211> LENGTH: 20
<212> TYPE: DNA
<213> ORGANISM: Homo sapiens

<400> SEQUENCE: 171
ggcgctgcgg cgggaggtgg                                               20

<210> SEQ ID NO 172
<211> LENGTH: 20
<212> TYPE: DNA
<213> ORGANISM: Homo sapiens

<400> SEQUENCE: 172
gaggctgcgg ctggggtgg                                                20

<210> SEQ ID NO 173
<211> LENGTH: 20
<212> TYPE: DNA
<213> ORGANISM: Homo sapiens

<400> SEQUENCE: 173
ggcatcacgg ctggaggtgg                                               20

<210> SEQ ID NO 174
<211> LENGTH: 20
<212> TYPE: DNA
<213> ORGANISM: Homo sapiens

<400> SEQUENCE: 174
agcactgtgg ctgggggagg                                               20

<210> SEQ ID NO 175
<211> LENGTH: 20
<212> TYPE: DNA
<213> ORGANISM: Homo sapiens

<400> SEQUENCE: 175
ggcactgagg gtggaggtgg                                               20

<210> SEQ ID NO 176
<211> LENGTH: 20
<212> TYPE: DNA
<213> ORGANISM: Homo sapiens

<400> SEQUENCE: 176
ggcactgggg ttggaggtgg                                               20

<210> SEQ ID NO 177
<211> LENGTH: 20
<212> TYPE: DNA
<213> ORGANISM: Homo sapiens

<400> SEQUENCE: 177
ggcactgcgg gtggaggcgg                                               20
```

```
<210> SEQ ID NO 178
<211> LENGTH: 20
<212> TYPE: DNA
<213> ORGANISM: Homo sapiens

<400> SEQUENCE: 178
tgcactgtgg ctggagatgg                                          20

<210> SEQ ID NO 179
<211> LENGTH: 20
<212> TYPE: DNA
<213> ORGANISM: Homo sapiens

<400> SEQUENCE: 179
gacaccacgg ctggagatgg                                          20

<210> SEQ ID NO 180
<211> LENGTH: 20
<212> TYPE: DNA
<213> ORGANISM: Homo sapiens

<400> SEQUENCE: 180
gccactgggg ctggggtgg                                           20

<210> SEQ ID NO 181
<211> LENGTH: 20
<212> TYPE: DNA
<213> ORGANISM: Homo sapiens

<400> SEQUENCE: 181
ggcactgggg ctgggggagg                                          20

<210> SEQ ID NO 182
<211> LENGTH: 20
<212> TYPE: DNA
<213> ORGANISM: Homo sapiens

<400> SEQUENCE: 182
ggcacagcag ctggaggtgc                                          20

<210> SEQ ID NO 183
<211> LENGTH: 20
<212> TYPE: DNA
<213> ORGANISM: Homo sapiens

<400> SEQUENCE: 183
ggctccgcag ctggaggtgg                                          20

<210> SEQ ID NO 184
<211> LENGTH: 20
<212> TYPE: DNA
<213> ORGANISM: Homo sapiens

<400> SEQUENCE: 184
agcactgtgg ctgggggagg                                          20

<210> SEQ ID NO 185
<211> LENGTH: 20
<212> TYPE: DNA
<213> ORGANISM: Homo sapiens

<400> SEQUENCE: 185
ggctctgtgg ctggaggagg                                          20
```

```
<210> SEQ ID NO 186
<211> LENGTH: 20
<212> TYPE: DNA
<213> ORGANISM: Homo sapiens

<400> SEQUENCE: 186
ggctctgagg ccagaggtgg                                              20

<210> SEQ ID NO 187
<211> LENGTH: 20
<212> TYPE: DNA
<213> ORGANISM: Homo sapiens

<400> SEQUENCE: 187
gtcactgcag ctggaggagg                                              20

<210> SEQ ID NO 188
<211> LENGTH: 20
<212> TYPE: DNA
<213> ORGANISM: Homo sapiens

<400> SEQUENCE: 188
ggcaatgtgg ctgaaggtgg                                              20

<210> SEQ ID NO 189
<211> LENGTH: 20
<212> TYPE: DNA
<213> ORGANISM: Homo sapiens

<400> SEQUENCE: 189
ggcactgcag ctagaggtgg                                              20

<210> SEQ ID NO 190
<211> LENGTH: 20
<212> TYPE: DNA
<213> ORGANISM: Homo sapiens

<400> SEQUENCE: 190
agcactgtgc ctgggggtgg                                              20

<210> SEQ ID NO 191
<211> LENGTH: 20
<212> TYPE: DNA
<213> ORGANISM: Homo sapiens

<400> SEQUENCE: 191
gggtgggggg agtttgctcc                                              20

<210> SEQ ID NO 192
<211> LENGTH: 20
<212> TYPE: DNA
<213> ORGANISM: Homo sapiens

<400> SEQUENCE: 192
ggatggaggg agtttgctcc                                              20

<210> SEQ ID NO 193
<211> LENGTH: 20
<212> TYPE: DNA
<213> ORGANISM: Homo sapiens

<400> SEQUENCE: 193
cgggggaggg agtttgctcc                                              20
```

<210> SEQ ID NO 194
<211> LENGTH: 20
<212> TYPE: DNA
<213> ORGANISM: Homo sapiens

<400> SEQUENCE: 194
ggggagggga agtttgctcc					20

<210> SEQ ID NO 195
<211> LENGTH: 20
<212> TYPE: DNA
<213> ORGANISM: Homo sapiens

<400> SEQUENCE: 195
gggagggtgg agtttgctcc					20

<210> SEQ ID NO 196
<211> LENGTH: 20
<212> TYPE: DNA
<213> ORGANISM: Homo sapiens

<400> SEQUENCE: 196
tagtggaggg agcttgctcc					20

<210> SEQ ID NO 197
<211> LENGTH: 20
<212> TYPE: DNA
<213> ORGANISM: Homo sapiens

<400> SEQUENCE: 197
gggtgggggg agtttgcccc					20

<210> SEQ ID NO 198
<211> LENGTH: 20
<212> TYPE: DNA
<213> ORGANISM: Homo sapiens

<400> SEQUENCE: 198
ctggtggggg agcttgctcc					20

<210> SEQ ID NO 199
<211> LENGTH: 20
<212> TYPE: DNA
<213> ORGANISM: Homo sapiens

<400> SEQUENCE: 199 gcgtggggggg tgtttgctcc					20

<210> SEQ ID NO 200
<211> LENGTH: 20
<212> TYPE: DNA
<213> ORGANISM: Homo sapiens

<400> SEQUENCE: 200
gtgggggtag agtttgctcc					20

<210> SEQ ID NO 201
<211> LENGTH: 20
<212> TYPE: DNA
<213> ORGANISM: Homo sapiens

<400> SEQUENCE: 201
ggtgagtgag tgtgtgcgtg                                         20

<210> SEQ ID NO 202
<211> LENGTH: 20
<212> TYPE: DNA
<213> ORGANISM: Homo sapiens

<400> SEQUENCE: 202
agtgagtgag tgtgtgtgtg                                         20

<210> SEQ ID NO 203
<211> LENGTH: 20
<212> TYPE: DNA
<213> ORGANISM: Homo sapiens

<400> SEQUENCE: 203
tgtgggtgag tgtgtgcgtg                                         20

<210> SEQ ID NO 204
<211> LENGTH: 20
<212> TYPE: DNA
<213> ORGANISM: Homo sapiens

<400> SEQUENCE: 204
cgcgagtgag tgtgtgcgcg                                         20

<210> SEQ ID NO 205
<211> LENGTH: 20
<212> TYPE: DNA
<213> ORGANISM: Homo sapiens

<400> SEQUENCE: 205
agtgaatgag tgtgtgtgtg                                         20

<210> SEQ ID NO 206
<211> LENGTH: 20
<212> TYPE: DNA
<213> ORGANISM: Homo sapiens

<400> SEQUENCE: 206
ggtgagtgag tgtgtgtgtg                                         20

<210> SEQ ID NO 207
<211> LENGTH: 20
<212> TYPE: DNA
<213> ORGANISM: Homo sapiens

<400> SEQUENCE: 207
agagagtgag tgtgtgcatg                                         20

<210> SEQ ID NO 208
<211> LENGTH: 20
<212> TYPE: DNA
<213> ORGANISM: Homo sapiens

<400> SEQUENCE: 208
tgtgagtaag tgtgtgtgtg                                         20

<210> SEQ ID NO 209
<211> LENGTH: 20
<212> TYPE: DNA
<213> ORGANISM: Homo sapiens

<400> SEQUENCE: 209

```
agcgagtggg tgtgtgcgtg                                              20

<210> SEQ ID NO 210
<211> LENGTH: 20
<212> TYPE: DNA
<213> ORGANISM: Homo sapiens

<400> SEQUENCE: 210
agtgtgtgag tgtgtgcgtg                                              20

<210> SEQ ID NO 211
<211> LENGTH: 20
<212> TYPE: DNA
<213> ORGANISM: Homo sapiens

<400> SEQUENCE: 211
gctgagtgag tgtatgcgtg                                              20

<210> SEQ ID NO 212
<211> LENGTH: 20
<212> TYPE: DNA
<213> ORGANISM: Homo sapiens

<400> SEQUENCE: 212
ggtgagtgag tgcgtgcggg                                              20

<210> SEQ ID NO 213
<211> LENGTH: 20
<212> TYPE: DNA
<213> ORGANISM: Homo sapiens

<400> SEQUENCE: 213
gttgagtgaa tgtgtgcgtg                                              20

<210> SEQ ID NO 214
<211> LENGTH: 20
<212> TYPE: DNA
<213> ORGANISM: Homo sapiens

<400> SEQUENCE: 214
actgtgtgag tgtgtgcgtg                                              20

<210> SEQ ID NO 215
<211> LENGTH: 20
<212> TYPE: DNA
<213> ORGANISM: Homo sapiens

<400> SEQUENCE: 215
tgtgggtgag tgtgtgcgtg                                              20

<210> SEQ ID NO 216
<211> LENGTH: 20
<212> TYPE: DNA
<213> ORGANISM: Homo sapiens

<400> SEQUENCE: 216
gggaaagacc cagcatccgt                                              20

<210> SEQ ID NO 217
<211> LENGTH: 20
<212> TYPE: DNA
<213> ORGANISM: Homo sapiens
```

```
<400> SEQUENCE: 217
gggaaagtcc cagcatcctt                                              20

<210> SEQ ID NO 218
<211> LENGTH: 20
<212> TYPE: DNA
<213> ORGANISM: Homo sapiens

<400> SEQUENCE: 218
gggaaaagcc cagcatccct                                              20

<210> SEQ ID NO 219
<211> LENGTH: 20
<212> TYPE: DNA
<213> ORGANISM: Homo sapiens

<400> SEQUENCE: 219
gggaaggacc cagcatcctg                                              20

<210> SEQ ID NO 220
<211> LENGTH: 20
<212> TYPE: DNA
<213> ORGANISM: Homo sapiens

<400> SEQUENCE: 220
gggaaatacc cagcatccaa                                              20

<210> SEQ ID NO 221
<211> LENGTH: 51
<212> TYPE: DNA
<213> ORGANISM: Homo sapiens

<400> SEQUENCE: 221
tcttaccata tttgacttca tccagrtatg taaaaataag taccgttaag t           51

<210> SEQ ID NO 222
<211> LENGTH: 51
<212> TYPE: DNA
<213> ORGANISM: Homo sapiens

<400> SEQUENCE: 222
agagaccatg cagaggtcgc ctctgbaaaa ggccagcgtt gtctccaaac t           51

<210> SEQ ID NO 223
<211> LENGTH: 51
<212> TYPE: DNA
<213> ORGANISM: Homo sapiens

<400> SEQUENCE: 223
aatatgctgg tttcataaca ggctcyctga tagattgtca gtaacttggc c           51

<210> SEQ ID NO 224
<211> LENGTH: 55
<212> TYPE: DNA
<213> ORGANISM: Homo sapiens
<220> FEATURE:
<221> NAME/KEY: misc_feature
<222> LOCATION: (26)..(30)
<223> OTHER INFORMATION: This region may or may not be present in its
      entirety

<400> SEQUENCE: 224
ttatccgtta tcatccattc ttatatgata gagaaactta ccctgatgat ccatg       55
```

<210> SEQ ID NO 225
<211> LENGTH: 51
<212> TYPE: DNA
<213> ORGANISM: Homo sapiens

<400> SEQUENCE: 225
tctgtggccg gtgtgagcac cacgtrccag gagcacagcc acatctgcct c            51

<210> SEQ ID NO 226
<211> LENGTH: 51
<212> TYPE: DNA
<213> ORGANISM: Homo sapiens

<400> SEQUENCE: 226
aacctcaagg gcacctttgc cacacbgagt gagctgcact gtgacaagct g            51

<210> SEQ ID NO 227
<211> LENGTH: 51
<212> TYPE: DNA
<213> ORGANISM: Homo sapiens

<400> SEQUENCE: 227
agacaccatg gtgcatctga ctcctvagga gaagtctgcc gttactgccc t            51

<210> SEQ ID NO 228
<211> LENGTH: 51
<212> TYPE: DNA
<213> ORGANISM: Homo sapiens

<400> SEQUENCE: 228
ctgaattttg gaagcagtat gttggyaagc aattcatttt atcctctagc t            51

<210> SEQ ID NO 229
<211> LENGTH: 51
<212> TYPE: DNA
<213> ORGANISM: Homo sapiens

<400> SEQUENCE: 229
ttcaggtaaa ttggaagagt ttgttyaagg gaaccttgag agagaatgta t            51

<210> SEQ ID NO 230
<211> LENGTH: 51
<212> TYPE: DNA
<213> ORGANISM: Homo sapiens

<400> SEQUENCE: 230
ttgaatggta aagttgatgc attctstgga ggctctatcg ttaatgaaaa a            51

<210> SEQ ID NO 231
<211> LENGTH: 51
<212> TYPE: DNA
<213> ORGANISM: Homo sapiens

<400> SEQUENCE: 231
aataaaacgt attcctttct tatcaygctg gatgtggata tcggcgagct g            51

<210> SEQ ID NO 232
<211> LENGTH: 51
<212> TYPE: DNA
<213> ORGANISM: Homo sapiens

<400> SEQUENCE: 232
tacctagtgt gcggggaacg aggctbcttc tacacaccca agacccgccg g            51

<210> SEQ ID NO 233
<211> LENGTH: 51
<212> TYPE: DNA
<213> ORGANISM: Homo sapiens

<400> SEQUENCE: 233
tgtgaaccaa cacctgtgcg gctcasacct ggtggaagct ctctacctag t        51

<210> SEQ ID NO 234
<211> LENGTH: 51
<212> TYPE: DNA
<213> ORGANISM: Homo sapiens

<400> SEQUENCE: 234
tgttcctgcg caggctgcgc ctctgratgg gcctcagcaa ggtcaaggag g        51

<210> SEQ ID NO 235
<211> LENGTH: 51
<212> TYPE: DNA
<213> ORGANISM: Homo sapiens

<400> SEQUENCE: 235
ggtggtgctc ggggtagcct acgccyagct ggccatcctg gtaggtgact g        51

<210> SEQ ID NO 236
<211> LENGTH: 51
<212> TYPE: DNA
<213> ORGANISM: Homo sapiens

<400> SEQUENCE: 236
cgaggccctg ctcacccagt ttgacygact caaccaggcc acagaggacg t        51

<210> SEQ ID NO 237
<211> LENGTH: 51
<212> TYPE: DNA
<213> ORGANISM: Homo sapiens

<400> SEQUENCE: 237
tgttgggggg tgccctccaa gtcagygact ctctcgatca gagcgcaatc g        51

<210> SEQ ID NO 238
<211> LENGTH: 51
<212> TYPE: DNA
<213> ORGANISM: Homo sapiens

<400> SEQUENCE: 238
cctggggaag agcagagata tacgtrccag gtggagcacc caggcctgga t        51

<210> SEQ ID NO 239
<211> LENGTH: 51
<212> TYPE: DNA
<213> ORGANISM: Homo sapiens

<400> SEQUENCE: 239
gagctgagaa aatctattgg gggttragag gagtgcctga ggaggtaatt a        51

<210> SEQ ID NO 240
<211> LENGTH: 51
<212> TYPE: DNA
<213> ORGANISM: Homo sapiens

<400> SEQUENCE: 240

```
acctcggccc ttctcagttc gctacraccc atacacccaa aggattgagg t            51

<210> SEQ ID NO 241
<211> LENGTH: 51
<212> TYPE: DNA
<213> ORGANISM: Homo sapiens

<400> SEQUENCE: 241
taggaacttt gctgccacaa tacctyggcc cttctcagtt cgctacgacc c            51

<210> SEQ ID NO 242
<211> LENGTH: 51
<212> TYPE: DNA
<213> ORGANISM: Homo sapiens

<400> SEQUENCE: 242
ttacaggaaa ttggccttgc ctctcygggt gcacctgatg aatacattga a            51

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ccatctcatc cctgcgtgtc                                               20
```

COMPOSITIONS AND METHODS FOR DETECTING NUCLEIC ACID REGIONS

CROSS-REFERENCE TO RELATED APPLICATIONS

This application is a continuation of U.S. Nonprovisional application Ser. No. 15/646,851, filed Jul. 11, 2017, now allowed, and claims the benefit of U.S. Provisional Application No. 62/361,239, filed Jul. 12, 2016, the disclosures of which are incorporated by reference in their entirety.

SEQUENCE LISTING

The instant application contains a Sequence Listing which has been submitted electronically in ASCII format and is hereby incorporated by reference in its entirety. Said ASCII copy, created on Sep. 18, 2017, is named LT01180_SL.txt and is 47,535 bytes in size.

BACKGROUND

Genome editing encompasses the powerful concept of directly correcting mutations in endogenous genes to cure or prevent diseases, particularly to cure or prevent inherited genetic disorders. An emerging example of this approach is the clinical trial of a zinc finger nuclease (ZFN) therapeutic engineered to disrupt CCR5, a co-receptor for HIV. Four main classes of engineered nucleases have been implicated in genome editing: 1) meganucleases, 2) zinc-finger nucleases, 3) transcription activator effector-like nucleases (TALEN), and 4) Clustered Regularly Interspaced Short Palindromic Repeats (CRISPR) Cas RNA-guided nucleases (RGN).

However, the potential therapeutic applications of these engineered nucleases will require a comprehensive knowledge of their off-target effects to minimize the risk of deleterious outcomes. Several in vivo or in vitro methods have been developed to detect off-target (Wang, et al., (2015), *Nat. Biotechnol.* 33:175-179); Crosetto, et al., (2013), *Nature Methods* 10:361-368); Frock, et al. (2016), *Nat. Biotechnol.* 33:179-187). Most of methods rely on an integration of viral DNA or short double strand DNA tags into the double strand break (DSB) followed by polymerase chain reaction (PCR) amplification and next generation sequencing (NGS). However, these methods can only detect partial off-targets due to DNA tag's degradation in cells, leading to the low efficiency of tag integration in DSB. A recent development of "Genome-wide, Unbiased Identification of DSBs Enabled by sequencing" (GUIDE-seq) method used phosphorothioate-modified double strand DNA as tag that prevented degradation and increased integration efficiency of tag into DSB in cells. However, one major issue of this method is non-specific PCR amplification that causes low specificity and low sensitivity due to a high-background. The invention provided herein addresses these and other shortcomings in the art.

SUMMARY

In a first aspect, there are provided methods of detecting one or more (e.g., from about one to about twenty, from about two to about twenty, from about four to about twenty, from about ten to about twenty, from about one to about fifteen, from about two to about fifteen, from about three to about fifteen, etc.) nucleic acid regions. Such methods include those involving contacting a nucleic acid sample containing the nucleic acid region with a primer (e.g., a 5'-phosphate primer). These methods may further include amplifying the nucleic acid region(s) using a first polymerase chain reaction procedure thereby forming a plurality of amplified nucleic acid regions (e.g., 5'-phosphate nucleic acid regions). These methods may further include ligating nucleic acid adapters to the plurality of amplified nucleic acid regions thereby forming a plurality of adapter nucleic acid regions. These methods may further include amplifying the plurality of adapter nucleic acid regions using a second polymerase chain reaction procedure thereby forming a plurality of amplified adapter nucleic acid regions. These methods may further include attaching the plurality of amplified adapter nucleic acid regions to one or more separation agents thereby forming a plurality of captured adaptor nucleic acid regions. These methods may further include detecting the captured adaptor nucleic acid regions thereby detecting the one or more nucleic acid regions.

In embodiments, the one or more nucleic acid regions detected by these methods may be within a genomic DNA sequence.

In embodiments, the one or more nucleic acid regions detected by these methods may be about 30 bp to 6000 bp in length.

In embodiments, the one or more nucleic acid regions detected by these methods may include an inserted sequence as a result of a double stranded break (DSB).

In embodiments, the one or more nucleic acid regions detected by these methods may include a foreign genomic fragment.

In embodiments, the one or more nucleic acid regions detected by these methods may include a genomic fragment of a virus. In embodiments, the virus may be an HIV.

In embodiments, the one or more nucleic acid regions detected by these methods may include a translocated genomic fragment.

In embodiments, the one or more nucleic acid regions detected by these methods may include a fragment of an IgG sequence.

In embodiments, these methods or embodiments thereof may further include isolating a genomic DNA including the one or more nucleic acid regions from a subject. In embodiments, the subject may be a cell. In embodiments, the cell may be a mammalian cell.

In embodiments, these methods or embodiment thereof may further include fragmenting the genomic DNA thereby forming a plurality of fragmented genomic DNA segments, where at least one of the fragmented genomic DNA segments includes the one or more nucleic acid regions. In embodiments, the fragmenting may be performed by hydroshearing, sonication, nebulization or enzymatic shearing. In embodiments, the fragmenting may be performed by contacting the genomic DNA with a DNase. In embodiments, the fragmenting may be performed by contacting the genomic DNA with a transposon-transposase complex. In embodiments, the transposase may be a MuA transposase, a Mos 1 transposase, a *Vibrio harvey* transposase or a Tn5 transposase. In embodiments, the fragmented genomic DNA segment may be about 100 bp to about 1000 bp in length. In embodiments, the fragmented genomic DNA segments may be blunt-ended.

In embodiments, these methods or embodiment thereof may further include ligating one or more universal adaptors to the plurality of fragmented genomic DNA segments thereby forming a plurality of universal adaptor fragmented genomic DNA segments. These methods may further include contacting the plurality of universal adaptor fragmented genomic DNA segments with primers complementary to the universal adaptors and primers complementary to the nucleic acid regions, and amplifying the universal adaptor fragmented genomic DNA segments involving a polymerase chain reaction procedure, thereby forming a plurality of amplified universal adapter fragmented genomic DNA segments.

In embodiments, the adapters used in these methods may be barcode adaptors.

In embodiments, amplifying the plurality of adapter nucleic acid regions may use primers complementary to the adaptors. In embodiments, the primers may include a spacer region.

In embodiments, the plurality of amplified adapter nucleic acid regions may each include a single strand tail on both ends. In embodiments, the separation agents may include a biotinylated tag oligo that is complementary to the single strand tail.

In embodiments, the separation agent may include at least one support. In embodiments, the supports may include at least one magnetic bead.

In embodiments, the detecting the captured adaptor nucleic acid regions may include sequencing the captured adaptor nucleic acid regions. In embodiments, the sequencing may be a next generation sequencing.

In one aspect, there are provided methods of detecting off-target insertion of nucleic acid into the genome of a cell. Such methods include those involving contacting the cell with at least one gene editing reagent and at least one donor nucleic acid molecule under conditions that allow for the generation of a double stranded break at a predetermined genetic locus. These methods may further include collecting nucleic acid from the cell of a previous step to generate a nucleic acid sample. These methods may further include contacting the nucleic acid sample containing the nucleic acid region with a primer (e.g., a 5'-phosphate primer). These methods may further include amplifying the nucleic acid region using a first polymerase chain reaction procedure thereby forming a plurality of amplified nucleic acid regions (e.g., 5'-phosphate nucleic acid regions). These methods may further include ligating nucleic acid adapters to the plurality of amplified nucleic acid regions (e.g., 5'-phosphate nucleic acid regions) thereby forming a plurality of adapter nucleic acid regions. These methods may further include amplifying the plurality of adapter nucleic acid regions using a second polymerase chain reaction procedure thereby forming a plurality of amplified adapter nucleic acid regions. These methods may further include attaching the plurality of amplified adapter nucleic acid regions to a separation agent thereby forming a plurality of captured adaptor nucleic acid regions. These methods may further include detecting the captured adaptor nucleic acid regions thereby detecting the nucleic acid region.

In embodiments of such methods, the gene editing reagents may include one or more zinc finger-FokI fusion protein, one or more TAL nuclease, one of more CRISPR-nucleic acid complex, or one or more argonaute-nucleic acid complex.

In one aspect, there are provided collections of reagents including at least one primer (e.g., a 5'-phosphate primer) and at least one barcode adaptor.

In embodiments, these reagents may be within one or more vessels. In embodiments, the collections or embodiments thereof may further include at least one primer complementary to the barcode adaptors. In embodiments, the primers may include a spacer region. In embodiments, In embodiments, the collections or embodiment thereof further may include at least one separation agent. In embodiments, the separation agents may include at least one support. In embodiments, the support may include at least one magnetic bead.

In embodiments, the collections or embodiments thereof may further includes at least one DNase.

In embodiments, the collections or embodiment thereof may further include at least one transposon-transposase complex.

In embodiments, the collections or embodiments thereof may further include at least one universal adaptor. In embodiments, the collections or embodiments thereof may further include at least one primer complementary to the universal adaptors.

In embodiments, the collections or embodiments thereof may include at least one primer for sequencing.

In one aspect, there are provided kits including an instruction and any collection of reagents described herein.

In one aspect, there are provided kits including an instruction, at least one primer (e.g., a 5'-phosphate primer) and at least one barcode adaptor. In embodiments, the at least one primer (e.g., a 5'-phosphate primer) may be within a first vessel and the at least one barcode adaptor may be within a second vessel. In embodiments, the first vessel and the second vessel may be the same vessel. In embodiments, the first vessel and the second vessel may be different vessels.

In embodiments, the kits or embodiments thereof may further include at least one primer complementary to the barcode adaptors. In embodiments, the primers may include a spacer region.

In embodiments, the kits or embodiments thereof may further include at least one separation agent. In embodiments, the separation agents may include at least one support. In embodiments, the supports may include at least one magnetic bead.

In embodiments, the kits or embodiments thereof may further include at least one DNase.

In embodiments, the kits or embodiments thereof may further include at least one transposon-transposase complex.

In embodiments, the kits or embodiments thereof may further include at least one universal adaptor. In embodiments, the kits or embodiments thereof may further include at least one primer complementary to the universal adaptors.

In embodiments, the kits or embodiments thereof may further include at least one primer for sequencing.

BRIEF DESCRIPTION OF THE DRAWINGS

FIG. 2A: Histogram depicting detection of HEK4 off-targets (that are detected by method of Tsai, et. al (2015) *GUIDE-seq enables genome-wide profiling of off-target cleavage by CRISPR-Cas nucleases. Nat. Biotechnol.* 33:187-197), developed in the Joung lab, transfected with All-in-One plasmid vector that expresses both CRISPR gRNA and Cas9 nuclease (GeneArt® CRISPR Nuclease Vector) followed by sample preparation using the method with 5'-phosphate primer based PCR and Magnetic Bead Enrichment (5pMBE, i.e., the method described herein) and without 5pMBE (similar to the method of Tsai, et. al (2015)). The ION PGM™ machine was used for next generation sequencing. A single Ion-Torrent 318 chip was used for each sample. Asterisk indicates on-target. The Y axis represents the normalized read count, i.e. read per million (RPM) and X-axis represents the off-targets detected by method of Tsai, et. al (2015). FIG. 2B: Histogram depicting new off-targets not detected by method of Tsai, et. al (2015), but detected by the methods with or without 5pMBE. There were more new off-targets were detected in the method with 5pMBE (i.e., the method described herein) than that without 5pMBE. Legend (FIGS. 2A-2B): with 5pBE (solid bars); without 5pBE (open bars).

FIG. 3A shows Venn diagram of number of on- and off-targets detected by Targeted ION AMPLISEQ™ and TEG-seq. FIG. 3B shows the correlation between detection percentage by Targeted ION AMPLISEQ™ and RPM by TEG-seq.

DETAILED DESCRIPTION

Figure 1:
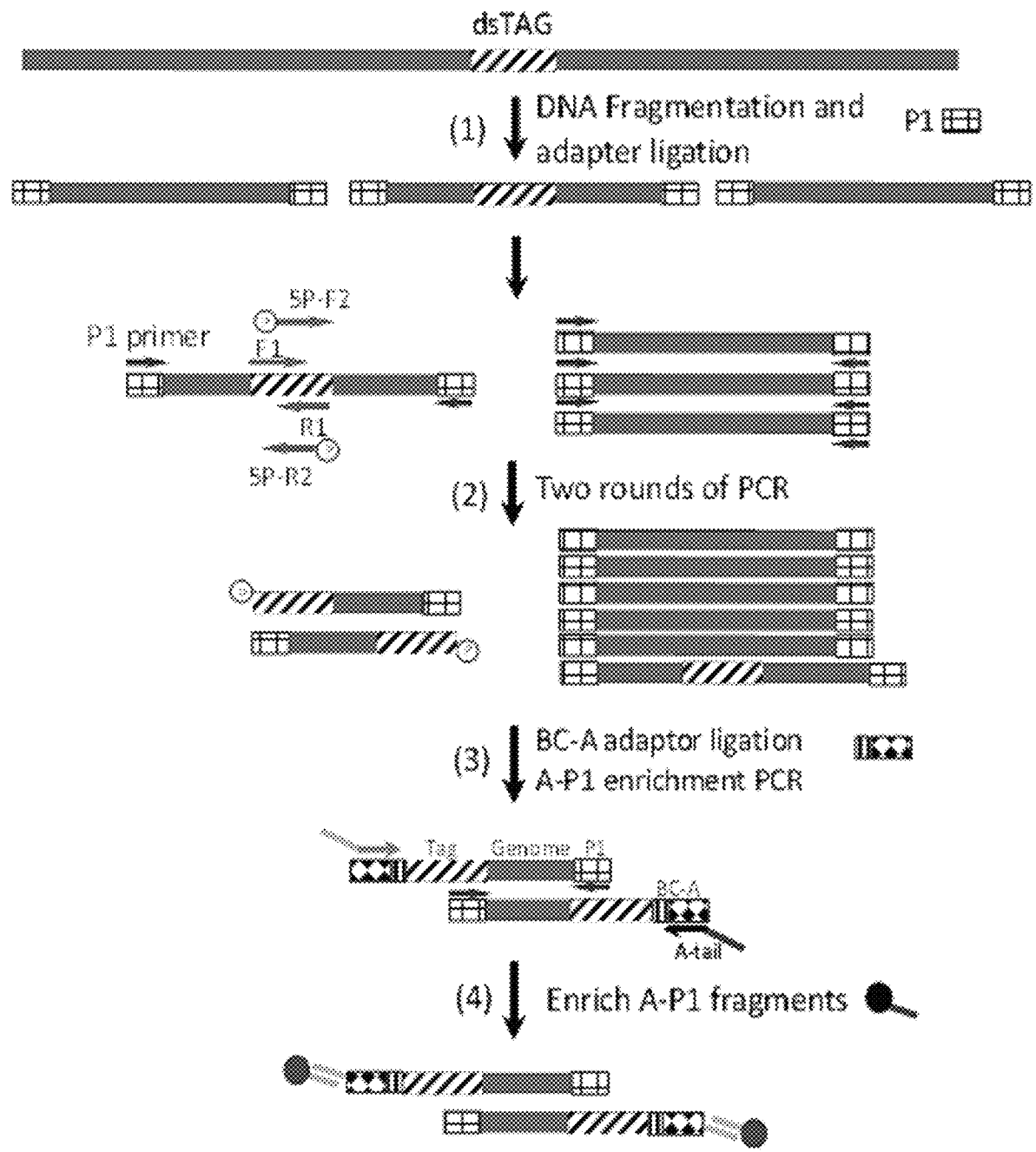
FIG. 1. Figure depicts an exemplary workflow for the invention described herein. Step 1: gDNA fragmentation and adaptor ligation. Step 2: PCR amplification; Step 3: BC-A adaptor ligation and BC-A/P1 enrichment PCR. Step 4: Enrichment of BC-A/P1 products. Legend: dsTAG (diagonal stripes); P1 (rectilinear grid); BC-A adaptor ligation with A-P1 enrichment PCR (diamond check region concatenated with vertical line region); A-P1 fragments (circle with tail).

Described herein are compositions and methods for an improved high throughput approach for detecting a nucleic acid region in a genome, with high efficiency and high sensitivity. The compositions and methods described herein are compatible with many next generation sequencing (NGS) platforms, such as the Ion Torrent Sequencers (PERSONAL GENOME MACHINE™ and Ion Torrent PROTON™ Sequencers (Life Technologies, CA) and Next-Generation Sequencing Platforms by ILLUMINA® (e.g., ILLUMINA® MISEQ®, ILLUMINA® HISEQ®, ILLUMINA® Genome Analyzer IIX).

Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

As used herein, the term "nucleotide" and its variants comprises any compound, including without limitation any naturally occurring nucleotide or analog thereof, which can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In embodiments, the nucleotide can optionally include a chain of phosphorus atoms comprising three, four, five, six, seven, eight, nine, ten or more phosphorus atoms. In embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In embodiments, the phosphorus atoms in the chain can have side groups having O, BH₃, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In embodiments, the nucleotide comprises a label and referred to herein as a "labeled nucleotide"; the label of the labeled nucleotide is referred to herein as a "nucleotide label". In embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g., α-thio-nucleotide 5'-triphosphates. For a review of nucleic acid chemistry, see: Shabarova, Z. and Bogdanov, A. Advanced Organic Chemistry of Nucleic Acids, VCH, New York, 1994.

As may be used herein, the terms "nucleic acid," "nucleic acid molecule," "nucleic acid oligomer," "oligonucleotide," "nucleic acid sequence," "nucleic acid region," "nucleic acid fragment," "nucleic acid tag," "nucleic acid segment," and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. A nucleic acid sequence, nucleic acid region, nucleic acid fragment, nucleic acid tag and/or nucleic acid segment may optionally be a portion of a larger nucleic acid polymer. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Nucleic acid" refers to deoxyribonucleotides or ribonucleotides and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press); and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include a spacer region. The spacer region can optionally include one or more nucleotides or can be comprised entirely of non-nucleotidyl moieties. In embodiments, the spacer region includes a non-replicable moiety that cannot be replicated by a polymerase. Such non-replicable moieties can include any moiety that cannot support template-based nucleotide polymerization by a polymerase. For example, the non-replicable moiety can include a non-nucleotidyl moiety (e.g., PEG or other carbon-based spacer, amino acid, or nucleotide analog that is not recognized by the polymerase used to perform the primer extension, for example uracil in conjunction with a DNA-dependent DNA polymerase, etc). When the primer containing a spacer region is used as a template for template-dependent nucleic acid synthesis by a polymerase, the polymerase cannot extend the synthesized nucleic acid strand beyond the non-replicable moiety. This typically results in the cessation or termination of nucleic acid synthesis after some portion of the primer has been copied into an opposing strand, leaving the remaining portion of the primer single stranded. The synthesized or replicated strand can remain base paired to the primer oligonucleotide, forming a primer extension product that is partly double stranded and partly single stranded. The single stranded region optionally includes some portion of the primer.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g., DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g., single stranded morpholino oligo).

With respect to particular nucleic acid sequences, "conservatively modified variants" refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

A "labeled nucleic acid or oligonucleotide" is one that is bound, either covalently, e.g., through a linker or a chemical bond, or noncovalently, e.g., through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

As used herein, the term "primer" or "probe" and their derivatives refer generally to any polynucleotide that can hybridize to a target sequence of interest. In embodiments, the primer can also serve to prime nucleic acid synthesis. Typically, the primer functions as a substrate onto which nucleotides can be polymerized by a polymerase; in embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In embodiments, the primer is a single-stranded oligonucleotide or polynucleotide. In embodiments, the primer is single-stranded but it can also be double-stranded. The primer optionally occurs naturally, as in a purified restriction digest, or can be produced synthetically. In embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In embodiments, the primer is an oligodeoxyribonucleotide or an oligoribonucleotide. In embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In embodiments, a primer can be paired with a compatible primer within an amplification or synthesis reaction to form a primer pair consisting or a forward primer and a reverse primer. In embodiments, the forward primer of the primer pair includes a sequence that is substantially complementary to at least a portion of a strand of a nucleic acid molecule, and the reverse primer of the primer pair includes a sequence that is substantially identical to at least of portion of the strand. In embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In embodiments, one end of an amplification or synthesis product is defined by the forward primer and the other end of the amplification or synthesis product is defined by the reverse primer. In embodiments, where the amplification or synthesis of lengthy primer extension products is required, such as amplifying an exon, coding region, or gene, several primer pairs can be created than span the desired length to enable sufficient amplification of the region. In embodiments, a primer can include one or more cleavable groups. In embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPS and a polymerase. In instances, the particular nucleotide sequence or a portion of the primer is known at the outset of the amplification reaction or can be determined by one or more of the methods disclosed herein. In embodiments, the primer includes one or more cleavable groups at one or more locations within the primer.

As used herein, "target-specific primer," or "sequence-specific primer," or "primer complementary to a sequence" or its derivatives, refers generally to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In embodiments, the target-specific primer is capable of hybridizing to at least a portion of its corresponding target sequence (or to a complement of the target sequence); such hybridization can optionally be performed under standard hybridization conditions or under stringent hybridization conditions. In embodiments, the target-specific primer is not capable of hybridizing to the target sequence, or to its complement, but is capable of hybridizing to a portion of a nucleic acid strand including the target sequence, or to its complement. In embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In embodiments, the target-specific primer is substantially non-complementary to other target sequences present in the sample; optionally, the target-specific primer is substantially non-complementary to other nucleic acid molecules present in the sample. In embodiments, nucleic acid molecules present in the sample that do not include or correspond to a target sequence (or to a complement of the target sequence) are referred to as "non-specific" sequences or "non-specific nucleic acids". In embodiments, the target-specific primer is designed to include a nucleotide sequence that is substantially complementary to at least a portion of its corresponding target sequence. In embodiments, a target-specific primer is at least 95% complementary, or at least 99% complementary, or identical, across its entire length to at least a portion of a nucleic acid molecule that includes its corresponding target sequence. In embodiments, a target-specific primer can be at least 90%, at least 95% complementary, at least 98% complementary or at least 99% complementary, or identical, across its entire length to at least a portion of its corresponding target sequence. In embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In embodiments, the target-specific primer can be substantially non-complementary at its 3' end or its 5' end to any other target-specific primer present in an amplification reaction. In embodiments, the target-specific primer can include minimal cross hybridization to other target-specific primers in the amplification reaction. In embodiments, target-specific primers include minimal cross-hybridization to non-specific sequences in the amplification reaction mixture. In embodiments, the target-specific primers include minimal self-complementarity. In embodiments, the target-specific primers can include one or more cleavable groups located at the 3' end. In embodiments, the target-specific primers can include one or more cleavable groups located near or about a central nucleotide of the target-specific primer. In embodiments, one of more targets-specific primers includes only non-cleavable nucleotides at the 5' end of the target-specific primer. In embodiments, a target specific primer includes minimal nucleotide sequence overlap at the 3' end or the 5' end of the primer as compared to one or more different target-specific primers, optionally in the same amplification reaction. In embodiments, 1, 2, 3, 4, 5, 6, 7, 8, 9, 10 or more, target-specific primers in a single reaction mixture include one or more of the above embodiments. In embodiments, substantially all of the plurality of target-specific primers in a single reaction mixture includes one or more of the above embodiments.

The probe may also be isolated nucleic acids immobilized on a solid surface (e.g., nitrocellulose, glass, quartz, fused silica slides), as in an array. In embodiments, the probe may be a member of an array of nucleic acids as described, for instance, in WO 96/17958. Techniques capable of producing high density arrays can also be used for this purpose (see, e.g., Fodor, et al., (1991) *Science* 251:767-773; Johnston (1998) *Curr. Biol.* 8: R171-R174; Schummer (1997) *Bio-*

*techniques* 23:1087-1092; Kern (1997) *Biotechniques* 23:120-124; U.S. Pat. No. 5,143,854).

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), *Laboratory Techniques In Biochemistry And Molecular Biology-Hybridization With Nucleic Acid Probes*, Part 1, Second Chapter "Overview of principles of hybridization and the strategy of nucleic acid probe assay", Elsevier, N.Y.

The term "hybridize" or "anneal" and their variants, as used herein in reference to two or more polynucleotides, refer to any process whereby any one or more nucleic acid sequences (each sequence comprising a stretch of contiguous nucleotide residues) within said polynucleotides undergo base pairing at two or more individual corresponding positions, for example as in a hybridized nucleic acid duplex. Optionally there can be "complete" or "total" hybridization between a first and second nucleic acid sequence, where each nucleotide residue in the first nucleic acid sequence can undergo a base pairing interaction with a corresponding nucleotide in the antiparallel position on the second nucleic acid sequence. In embodiments, hybridization can include base pairing between two or more nucleic acid sequences that are not completely complementary, or are not base paired, over their entire length. For example, "partial" hybridization occurs when two nucleic acid sequences undergo base pairing, where at least 20% but less than 100%, of the residues of one nucleic acid sequence are base paired to residues in the other nucleic acid sequence. In embodiments, hybridization includes base pairing between two nucleic acid sequences, where at least 50%, but less than 100%, of the residues of one nucleic acid sequence are base paired with corresponding residues in the other nucleic acid sequence. In embodiments, at least 70%, 80%, 90% or 95%, but less than 100%, of the residues of one nucleic acid sequence are base paired with corresponding residues in the other nucleic acid sequence. Two nucleic acid sequences are said to be "substantially hybridized" when at least 85% of the residues of one nucleic acid sequence are base paired with corresponding residues in the other nucleic acid sequence. In situations where one nucleic acid molecule is substantially longer than the other (or where the two nucleic acid molecule include both substantially complementary and substantially non-complementary regions), the two nucleic acid molecules can be described as "hybridized" even when portions of either or both nucleic acid molecule can remain unhybridized. "Unhybridized" describes nucleic acid sequences in which less than 20% of the residues of one nucleic acid sequence are base paired to residues in the other nucleic acid sequence. In embodiments, base pairing can occur according to some conventional pairing paradigm, such as the A-T/U and G-C base pairs formed through specific Watson-Crick type hydrogen bonding between the nucleobases of nucleotides and/or polynucleotides positions antiparallel to each other; in other embodiments, base pairing can occur through any other paradigm whereby base pairing proceeds according to established and predictable rules.

Hybridization of two or more polynucleotides can occur whenever said two or more polynucleotides come into contact under suitable hybridizing conditions. Hybridizing conditions include any conditions that are suitable for nucleic acid hybridization; methods of performing hybridization and suitable conditions for hybridization are well known in the art. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "Tm"; parameters such as salts, buffers, pH, temperature, GC % content of the polynucleotide and primers, and/or time. Typically, hybridization is favored in lower temperatures and/or increased salt concentrations, as well as reduced concentrations of organic solvents. High-stringency hybridization conditions will typically require a higher degree of complementary between two target sequences for hybridization to occur, whereas low-stringency hybridization conditions will favor hybridization even when the two polynucleotides to be hybridized exhibit lower levels of complementarity. The hybridization conditions can be applied during a hybridization step, or an optional and successive wash step, or both the hybridization and optional wash steps.

Examples of high-stringency hybridization conditions include any one or more of the following: salt concentrations (e.g., NaCl) of from about 0.0165 to about 0.0330 M; temperatures of from about 5° C. to about 10° C. below the melting point (Tm) of the target sequences (or polynucleotides) to be hybridized; and/or formamide concentrations of about 50% or higher. Typically, high-stringency hybridization conditions permit binding between sequences having high homology, e.g., ≥95% identity or complementarity. In one exemplary embodiment of high-stringency hybridization conditions, hybridization is performed at about 42° C. in a hybridization solution containing 25 mM $KPO_4$ (pH 7.4), 5×SSC, 5×Denhardt's solution, 50 µg/mL denatured, sonicated salmon sperm DNA, 50% formamide, 10% Dextran sulfate, and 1-15 ng/mL double stranded polynucleotide (or double stranded target sequence), while the washes are performed at about 65° C. with a wash solution containing 0.2×SSC and 0.1% sodium dodecyl sulfate.

Examples of medium-stringency hybridization conditions can include any one or more of the following: salt concentrations (e.g., NaCl) of from about 0.165 to about 0.330 M; temperatures of from about 20° C. to about 29° C. below the melting point (Tm) of the target sequences to be hybridized;

and/or formamide concentrations of about 35% or lower. Typically, such medium-stringency conditions permit binding between sequences having high or moderate homology, e.g., 80% identity or complementarity. In one exemplary embodiment of medium stringency hybridization conditions, hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL double stranded polynucleotide (or double stranded target sequence), while the washes are performed at about 50° C. with a wash solution containing 2×SSC and 0.1% sodium dodecyl sulfate.

Examples of low-stringency hybridization conditions include any one or more of the following: salt concentrations (e.g., NaCl) of from about 0.330 to about 0.825 M; temperatures of from about 40° C. to about 48° C. below the melting point (Tm) of the target sequences to be hybridized; and/or formamide concentrations of about 25% or lower. Typically, such low-stringency conditions permit binding between sequences having low homology, e.g., 50% identity or complementarity.

Some exemplary conditions suitable for hybridization include incubation of the polynucleotides to be hybridized in solutions having sodium salts, such as NaCl, sodium citrate and/or sodium phosphate. In embodiments, hybridization or wash solutions can include about 10-75% formamide and/or about 0.01-0.7% sodium dodecyl sulfate (SDS). In embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In embodiments, the hybridization or washing solution can include BSA (bovine serum albumin). In embodiments, hybridization or washing can be conducted at a temperature range of about 20-25° C., or about 25-30° C., or about 30-35° C., or about 35-40° C., or about 40-45° C., or about 45-50° C., or about 50-55° C., or higher.

In embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer.

In embodiments, hybridization or wash conditions can be conducted at a pH range of about 5-10, or about pH 6-9, or about pH 6.5-8, or about pH 6.5-7.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. Optionally, the polymerase can possess 5' exonuclease activity or terminal transferase activity. In embodiments, the polymerase can be optionally reactivated, for example through the use of heat, chemicals or re-addition of new amounts of polymerase into a reaction mixture. In embodiments, the polymerase can include a hot-start polymerase or an aptamer based polymerase that optionally can be reactivated.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $P^{32}$-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In embodiments, the plexy can be about 12-plex, 24-plex, 48-plex, 96-plex, 192-plex, 384-plex, 768-plex, 1536-plex, 3072-plex, 6144-plex or higher.

As used herein, "amplify", "amplifying" or "amplification reaction" and their derivatives, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In embodiments, such amplification is performed using isothermal conditions; in other embodiments, such amplification can include thermocycling. In embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In embodiments, the amplification conditions can include isothermal conditions or alternatively can include thermocycling conditions, or a combination of isothermal and thermocycling conditions. In embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in embodiments, amplification conditions include a plurality of cycles where the steps of annealing, extending and separating are repeated. Typically, the amplification conditions include cations such as Mg++ or Mn++(e.g., $MgCl_2$, etc.) and can also include various modifiers of ionic strength.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3' OH end of the nucleic acid molecule by the polymerase.

As used herein, "amplified sequences" and its derivatives, refers generally to a nucleic acid sequence produced by the amplification of/amplifying the sequences using sequence-specific primers and the methods provided herein. The amplified sequences may be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure, the amplified sequences are typically less than 50% complementary to any portion of another amplified sequence in the reaction.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In embodiments, the 3' end does not include any unlinked 3' hydroxyl group but can include any moiety capable of serving as a site for attachment of nucleotides via primer extension and/or nucleotide polymerization. In embodiments, the term "3' end" for example when referring to a target-specific primer, can include the terminal 10 nucleotides, the terminal 5 nucleotides, the terminal 4, 3, 2 or fewer nucleotides at the 3' end. In embodiments, the term "3' end" when referring to a target-specific primer can include nucleotides located at nucleotide positions 10 or fewer from the 3' terminus.

As used herein, "ligase" and its derivatives, refers generally to any agent capable of catalyzing the ligation of two substrate molecules. In embodiments, the ligase includes an enzyme capable of catalyzing the joining of nicks between adjacent nucleotides of a nucleic acid. In embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and *E. coli* DNA ligase.

As used herein, "ligation conditions" and its derivatives, generally refers to conditions suitable for ligating two molecules to each other. In embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap can be ligated in the presence of an enzyme, such as ligase at an appropriate temperature and pH. In embodiments, T4 DNA ligase can join a nick between nucleic acids at a temperature of about 70-72° C.

As used herein, "blunt-end ligation" and its derivatives, refers generally to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang". In embodiments, the end of nucleic acid molecule does not include any single stranded portion, such that every nucleotide in one strand of the end is based paired with opposing nucleotides in the other strand of the same nucleic acid molecule. In embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in Mitra and Varley, U.S. Pat. Publ. 2010/0129874, published May 27, 2010. In embodiments, blunt-ended ligation includes a nick translation reaction to seal a nick created during the ligation process.

As used herein, "5' end", and its derivatives, generally refers to an end of a nucleic acid molecule, for example a target sequence or amplified target sequence, which includes a free 5' phosphate group or its equivalent. In embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In embodiments, the 5' end does not include any unlinked 5' phosphate group but can include any moiety capable of serving as a site of attachment to a 3' hydroxyl group, or to the 3' end of another nucleic acid molecule. In embodiments, the term "5' end" for example when referring to a target-specific primer, can include the terminal 10 nucleotides, the terminal 5 nucleotides, the terminal 4, 3, 2 or fewer nucleotides at the 5' end. In embodiments, the term "5' end" when referring to a target-specific primer can include nucleotides located at positions 10 or fewer from the 5' terminus. In embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, the term "adaptor" includes polynucleotides or oligonucleotides comprising DNA, RNA, chimeric RNA/DNA molecules, or analogs thereof. The term "adaptor" as used herein refers to a non-target nucleic acid component, generally DNA, that provides a means of addressing a nucleic acid fragment to which it is joined. For example, an adaptor comprises a nucleotide sequence that permits identification, recognition, and/or molecular or biochemical manipulation of the DNA to which the adaptor is attached (e.g., by providing a site for annealing an oligonucleotide, such as a primer for extension by a DNA polymerase, or an oligonucleotide for capture or for a ligation reaction).

In embodiments, an adaptor can include one or more ribonucleoside residues. In embodiments, an adaptor can be single-stranded or double-stranded nucleic acids, or can include single-stranded and/or double-stranded portions. In embodiments, an adaptor can have any structure, including linear, hairpin, forked, or stem-loop.

In embodiments, an adaptor can have any length, including fewer than 10 bases in length, or about 10-20 bases in length, or about 20-50 bases in length, or about 50-100 bases in length, or longer.

In embodiments, an adaptor can have any combination of blunt end(s) and/or sticky end(s). In embodiments, at least one end of an adaptor can be compatible with at least one end of a nucleic acid fragment. In embodiments, a compatible end of an adaptor can be joined to a compatible end of a nucleic acid fragment. In embodiments, an adaptor can have a 5' or 3' overhang end.

In embodiments, an adaptor can have a 5' or 3' overhang tail. In embodiments, the tail can be any length, including 1-50 or more nucleotides in length.

In embodiments, an adaptor can include an internal nick. In embodiments, an adaptor can have at least one strand that lacks a terminal 5' phosphate residue. In embodiments, an adaptor lacking a terminal 5' phosphate residue can be joined to a nucleic acid fragment to introduce a nick at the junction between the adaptor and the nucleic acid fragment.

In embodiments, an adaptor can include a nucleotide sequence that is part of, or is complementary to, any portion of a primer, or to the entire sequence of a primer, present in the amplification reaction mixture, or any portion of a sequencing primer, or the entire sequence of a sequencing primer, or any portion thereof.

In embodiments, an adaptor can include degenerate sequences. In embodiments, an adaptor can include one or more inosine residues. In embodiments, a barcode adaptor can include a uniquely identifiable sequence. In embodiments, a barcode adaptor can be used for constructing multiplex nucleic acid libraries.

In embodiments, an adaptor can include at least one scissile linkage. In embodiments, a scissile linkage can be susceptible to cleavage or degradation by an enzyme or chemical compound. In embodiments, an adaptor can include at least one phosphorothiolate, phosphorothioate, and/or phosphoramidate linkage.

In embodiments, an adaptor can include identification sequences. In embodiments, an identification sequences can be used for sorting or tracking. In embodiments, an identification sequences can be a unique sequence (e.g., barcode sequence). In embodiments, a barcode sequence can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In embodiments, an adaptor can include any type of restriction enzyme recognition sequence, including type I, type II, type Hs, type IIB, type III or type IV restriction enzyme recognition sequences.

In embodiments, an adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

As used herein, the term "sequencing" and its variants comprise obtaining sequence information from a nucleic acid strand, typically by determining the identity of at least one nucleotide (including its nucleobase component) within the nucleic acid strand. While in embodiments, "sequencing" a given region of a nucleic acid molecule includes identifying each and every nucleotide within the region that is sequenced, "sequencing" can also include methods whereby the identity of one or more nucleotides in is determined, while the identity of some nucleotides remains undetermined or incorrectly determined.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "isolated" may also refer to a cell or sample cells. An isolated cell or sample cells are a single cell type that is substantially free of many of the components which normally accompany the cells when they are in their native state or when they are initially removed from their native state. In embodiments, an isolated cell sample retains those components from its natural state that are required to maintain the cell in a desired state. In embodiments, an isolated (e.g., purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In embodiments, the cells are isolated through the use of a cell sorter. In embodiments, antibodies against cell proteins are used to isolate cells.

As used herein, the term "conjugate" refers to the association between atoms or molecules. The association can be direct or indirect. For example, a conjugate between a first moiety (e.g., polyamine moiety) and a second moiety (peptide moiety) provided herein can be direct, e.g., by covalent bond, or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; ADVANCES IN CHEMISTRY SERIES, VOL. 198, American Chemical Society, Washington, D.C., 1982. In embodiments, the first moiety (e.g., polyamine moiety) is non-covalently attached to the second moiety (peptide moiety) through a non-covalent chemical reaction between a component of the first moiety (e.g., polyamine moiety) and a component of the second moiety (peptide moiety). In other embodiments, the first moiety (e.g., polyamine moiety) includes one or more reactive moieties, e.g., a covalent reactive moiety, as described herein (e.g., alkyne, azide, maleimide or thiol reactive moiety). In embodiments, the first moiety (e.g., polyamine moiety) includes a linker with one or more reactive moieties, e.g., a covalent reactive moiety, as described herein (e.g., alkyne, azide, maleimide or thiol reactive moiety). In embodiments, the second moiety (peptide moiety) includes one or more reactive moieties, e.g., a covalent reactive moiety, as described herein (e.g., alkyne, azide, maleimide or thiol reactive moiety). In embodiments, the second moiety (peptide moiety) includes a linker with one or more reactive moieties, e.g., a covalent reactive moiety, as described herein (e.g., alkyne, azide, maleimide or thiol reactive moiety).

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments, contacting includes, for example, allowing a nucleic acid to interact with an endonuclease.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $P^{32}$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

As defined herein, "sample" and its derivatives, is used in its broadest sense and includes any specimen, culture and the like that is suspected of including a target. In embodiments, the sample comprises DNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen.

"Biological sample" refers to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., Spodoptera) and human cells.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "vector" is a nucleic acid that is capable of transporting another nucleic acid into a cell. A vector is capable of directing expression of a protein or proteins encoded by one or more genes carried by the vector when it is present in the appropriate environment.

A "cell culture" is an in vitro population of cells residing outside of an organism. The cell culture can be established from primary cells isolated from a cell bank or animal, or secondary cells that are derived from one of these sources and immortalized for long-term in vitro cultures.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al., (2001) *Gene Therapy* 8:1-4 and Prochiantz (2007) *Nat. Methods* 4:119-20.

Methods

In some aspects, the invention includes compositions and methods for the identification of nucleic acid regions within nucleic acid molecules (e.g., chromosomes). An exemplary workflow of the invention is shown in FIG. 1.

In many instances, the invention will involve one or more of the following:

1. Contacting of a cell with a gene editing reagent and a donor nucleic acid molecule to generate cellular nucleic acid molecules containing all or part of the donor nucleic acid molecule.
2. The preparation of a nucleic acid sample from the cell.
3. Processing of nucleic acid in the nucleic acid sample to produce nucleic acid segments with an average desired length.
4. The additional of terminal adapters to the nucleic acid segments (e.g., by use of polymerase mediate amplification).
5. The addition of "barcodes" to the nucleic acid segments (e.g., by use of polymerase mediate amplification) to generate barcoded nucleic acid molecules.
6. The enrichment of barcoded nucleic acid molecules containing all or part of the donor nucleic acid.
7. The identification of one or more cellular nucleic acid regions associated with donor nucleic acid.

In embodiments, a donor nucleic acid molecule may include an insert sequence to the double strand break (DSB) created by a gene editing reagent (e.g., an engineered nuclease). In embodiments, a donor nucleic acid molecule may include a foreign genome or a fragment thereof. In embodiments, a donor nucleic acid molecule may include a translocated genomic sequence or a fragment thereof. In embodiments, a donor nucleic acid molecule may include a nucleic acid encoding an antibody sequence.

In a first aspect, there is provided a method of detecting a nucleic acid region. The method includes contacting a nucleic acid sample containing the nucleic acid region with a primer (e.g., a 5'-phosphate). The method further includes amplifying the nucleic acid region using a first polymerase chain reaction procedure thereby forming a plurality of amplified nucleic acid regions (e.g., 5'-phosphate nucleic acid regions). The method further includes ligating a nucleic acid adapter to the plurality of amplified nucleic acid regions (e.g., 5'-phosphate nucleic acid regions) thereby forming a plurality of adapter nucleic acid regions. The method further includes amplifying the plurality of adapter nucleic acid regions using a second polymerase chain reaction procedure thereby forming a plurality of amplified adapter nucleic acid regions. The method further includes attaching the plurality of amplified adapter nucleic acid regions to a separation agent thereby forming a plurality of captured adaptor nucleic acid regions. The method further includes detecting the captured adapter nucleic acid regions thereby detecting the nucleic acid regions.

In embodiments, the polymerase can be an enzyme such as Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*). In some embodiments, the DNA polymerase can include at least one polymerase such as AMPLITAQ GOLD® DNA polymerase (Applied Biosciences), Stoffel fragment of AMPLITAQ® DNA Polymerase (Roche), KOD polymerase (EMD Biosciences), KOD Hot Start polymerase (EMD Biosciences), DEEP VENT™ DNA polymerase (New England Biolabs), PHUSION® polymerase (New England Biolabs), KlenTaql polymerase (DNA Polymerase Technology, Inc), KlenTaq Long Accuracy polymerase (DNA Polymerase Technology, Inc), OMNI KLENTAQ™ LA DNA polymerase (DNA Polymerase Technology, Inc), PLATINUM® Taq DNA Polymerase (Invitrogen), HEMO KLENTAQ™ (New England Biolabs), PLATINUM® Taq DNA Polymerase High Fidelity (Invitrogen), PLATINUM® Pfx (Invitrogen), ACCUPRIME™ Pfx (Invitrogen), or ACCUPRIME™ Taq DNA Polymerase High Fidelity (Invitrogen).

In embodiments, the nucleic acid region is within a genomic DNA sequence. The term "genomic DNA sequence," "gDNA," "genomic fragment" and the like refer, in the usual and customary sense, to DNA of chromosomal origin, in contrast to extrachromosomal DNA, e.g., plasmid DNA.

In embodiments, the nucleic acid region is about 30 bp to about 6000 bp in length, e.g., about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950 or 6000 bp in length.

In embodiments, the nucleic acid region is about 100 bp to 5000 bp in length. In embodiments, the nucleic acid region is about 200 bp to about 4000 bp in length. In embodiments, the nucleic acid region is about 300 bp to about 3000 bp in length. In embodiments, the nucleic acid region is about 400 bp to about 2000 bp in length. In embodiments, the nucleic acid region is about 500 bp to about 1000 bp in length. In embodiments, the nucleic acid region is about 30 bp to about 500 bp in length. In embodiments, the nucleic acid region is about 500 bp to about 1000 bp in length. In embodiments, the nucleic acid region is about 1000 bp to about 2000 bp in length. In embodiments, the nucleic acid region is about 2000 bp to about 3000 bp in length. In embodiments, the nucleic acid region is about 3000 bp to 4000 bp in length. In embodiments, the nucleic acid region is about 4000 bp to 5000 bp in length. In embodiments, the nucleic acid region is about 5000 bp to 6000 bp in length.

The term "bp" or the like refers in the context of duplex nucleic acid, in the usual and customary sense, to the number of base pairs characteristic of duplex nucleic acid, e.g., A-T or G-C base pairs. In the context of non-duplex nucleic acid, the term refers to the number of nucleotides included within a sequence.

In embodiments, the method described herein can identify the locations of engineered nuclease cleavage sites in living cells, e.g., cells in which the non-homologous end joining (NHEJ) repair pathway is active. Accordingly, in embodiments, the nucleic acid region that is detected by the methods described herein includes an insert sequence (i.e., a donor nucleic acid molecule) as a result of a double stranded break (DSB), where the DSB is generated by an engineered nuclease. The term "double stranded break" or the like in the context of nucleic acids (e.g., duplex DNA) refers, in the usual and customary sense, to scission of both sense and anti-sense strands.

The methods described herein can be used in any cell that is capable of repairing a DSB in genomic DNA. The two major DSB repair pathways in eukaryotic cells are homologous recombination (HR) and non-homologous end joining (NHEJ). In embodiments, the methods are performed in cells capable of NHEJ. Methods for detecting NHEJ activity are known in the art; for a review of the NHEJ canonical and alternative pathways, see Liu et al, *Nucleic Acids Res*. Jun. 1, 2014; 42(10):6106-6127. In embodiments, the methods are performed using the genomic DNA isolated from the cells capable of NHEJ under a condition that promotes NHEJ.

As used herein the term "gene editing reagent" refers to a composition that has one or more sequence specific nucleic acid cleavage activity or contains a component of a complex that has one or more sequence specific nucleic acid cleavage activity. Exemplary gene altering reagents are reagents that contain (i) functional zinc finger-FokI fusion proteins, (ii) functional TAL-FokI fusion protein, and (iii) gRNA/

CRISPR and/or gDNA/argonaute protein complexes capable of site specific cleavage of target nucleic acid molecules.

In embodiments, the nuclease can be transiently or stably expressed in the cell, using methods known in the art. Suitable nucleases that can be used include, but are not limited to, meganucleases, zinc-finger nucleases, transcription activator effector-like nucleases (TALEN), and Clustered Regularly Interspaced Short Palindromic Repeats (CRISPR) Cas RNA-guided nucleases (RGN).

For specific proteins described herein, the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In embodiments, variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

For example, a "CRISPR associated protein 9," "Cas9" or "Cas9 protein" as referred to herein includes any of the recombinant or naturally-occurring forms of the Cas9 endonuclease or variants or homologs thereof that maintain Cas9 endonuclease enzyme activity (e.g., within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 protein. In embodiments, the Cas9 protein is substantially identical to the protein identified by the UniProt reference number Q99ZW2 or a variant or homolog having substantial identity thereto. Cas9 refers to the protein also known in the art as "nickase". In embodiments, Cas9 binds a CRISPR (clustered regularly interspaced short palindromic repeats) nucleic acid sequence. In embodiments, the CRISPR nucleic acid sequence is a prokaryotic nucleic acid sequence. The term "all-in-one" or the like refers, in the usual and customary sense, to a ready to use vector construction system for CRISPR/Cas9-mediated multiplex genome engineering, typically providing multiple guide RNA (gRNA) expression cassettes and a Cas9 nuclease/ nickase expression cassette. See, e.g., Sakuma et al., 2014, *Sci. Rep.* 4:5400.

In some embodiments of the invention, CRISPR/Cas9-mediated multiplex genome engineering is mediated by the introduction into a cell of Cas9/gRNA complexes. It has been found that in many instances, transfection of Cas9/gRNA complexes into cells results in a lower level of off-target effects than when (1) Cas9 is transcribed and translated and (2) gRNA is transcribed from DNA in cells. Data to this effect is set out in Example 3. Thus, the invention includes compositions and methods for reducing off-target insertions of nucleic acid molecules into the genomes of cells by the introduction of Cas9/gRNA complexes into these cells.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. A zinc finger nuclease is a site-specific endonuclease designed to bind and cleave DNA at specific positions. There are two protein domains. The first domain is the DNA binding domain, which consists of eukaryotic transcription factors and contains the zinc finger. The second domain is the nuclease domain, which consists of the FokI restriction enzyme and is responsible for the catalytic cleavage of DNA.

Transcription activator-like effector nucleases (TALEN) are restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ, a technique known as genome editing with engineered nucleases. TAL effectors are proteins that are secreted by Xanthomonas bacteria via their type III secretion system when they infect plants. The DNA binding domain contains a repeated highly conserved 33-34 amino acid sequence with divergent 12th and 13th amino acids. These two positions, referred to as the Repeat Variable Diresidue (RVD), are highly variable and show a strong correlation with specific nucleotide recognition. This straightforward relationship between amino acid sequence and DNA recognition has allowed for the engineering of specific DNA-binding domains by selecting a combination of repeat segments containing the appropriate RVDs. Notably, slight changes in the RVD and the incorporation of "nonconventional" RVD sequences can improve targeting specificity. The non-specific DNA cleavage domain from the end of the FokI endonuclease can be used to construct hybrid nucleases that are active in a yeast assay. These reagents are also active in plant cells and in animal cells. Initial TALEN studies used the wild-type FokI cleavage domain, but some subsequent TALEN studies also used FokI cleavage domain variants with mutations designed to improve cleavage specificity and cleavage activity. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity.

In embodiments, the method described herein can be used to detect the existing and/or the integration site of a foreign genome or a fragment of a foreign genome. In embodiments, the nucleic acid region that is detected by the methods described herein includes a foreign genomic fragment sequence. The term "foreign genome," or "foreign genomic fragment" in this context refers, in the usual and customary sense, to genomic DNA originated from another species, i.e., a species that is different from the species where the nucleic acid sample is obtained. Accordingly, in embodiments, nucleic acid region that is detected by the methods described herein can include a genomic fragment sequence of a virus, a bacterium, or a fungus. In embodiments, the virus is an HIV, e.g., HIV-1, HIV-2, and groups and subgroups thereof as known in the art.

In embodiments, the method described herein can be used to detect if there is a translocated genomic sequence or a fragment thereof and/or where the translocated genomic sequence is now located. The term "translocated" or the like in the context of a genomic fragment refers, in the usual and customary sense, to a chromosomal abnormality due to rearrangement of parts of a chromosome, e.g., between nonhomologous chromosomes. A translocated genomic fragment can join two otherwise separated genes or fragments thereof. Accordingly, in embodiments, the nucleic acid region that is detected by the methods described herein includes a translocated genomic sequence or a fragment thereof.

In embodiments, the method described herein can be used to detect an integration of an antibody sequence in a living cells' genome, where the cell is engineered to produce this antibody. The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

In embodiments, the nucleic acid region that is detected by the methods described herein includes a nucleic acid sequence encoding an IgG, IgM, IgA, IgD or IgE antibody or a fragment thereof. In embodiments, the nucleic acid region that is detected by the methods described herein includes a nucleic acid sequence encoding an IgG antibody or a fragment thereof.

In embodiments, the method further includes isolating a genomic DNA including the nucleic acid sequence from a cell or a sample. In embodiments, the cell is a mammalian cell. Any methods known in the art can be used for isolating genomic DNA from a cell or a biological sample isolated from subject. The terms "subject" used herein to refers to a vertebrate, preferably a mammal, more preferably a human. The mammal can be, e.g., a human or appropriate non-human mammal, such as primate, mouse, rat, dog, cat, cow, horse, goat, camel, sheep or a pig. The subject can also be a bird or fowl. Tissues, cells and their progeny of a biological entity obtained in vivo or cultured in vitro are also encompassed.

In embodiments, the method includes:
(i) isolating a genomic DNA including the nucleic acid sequence from a cell or a sample;
(ii) contacting a nucleic acid sample containing the nucleic acid region (e.g., the genomic DNA) with a primer (e.g., a 5'-phosphate primer);
(iii) amplifying the nucleic acid region using a first polymerase chain reaction procedure thereby forming a plurality of amplified nucleic acid regions (e.g., 5'-phosphate nucleic acid regions);
(iv) ligating a nucleic acid adapter to the plurality of amplified nucleic acid regions (e.g., 5'-phosphate nucleic acid regions) thereby forming a plurality of adapter nucleic acid regions;
(v) amplifying the plurality of adapter nucleic acid regions using a second polymerase chain reaction procedure thereby forming a plurality of amplified adapter nucleic acid regions;
(vi) attaching the plurality of amplified adapter nucleic acid regions to a separation agent thereby forming a plurality of captured adaptor nucleic acid regions; and
(vii) detecting the captured adapter nucleic acid regions thereby detecting the nucleic acid regions.

In embodiments, the method further includes fragmenting the genomic DNA thereby forming a plurality of fragmented genomic DNA segments, where at least one of the fragmented genomic DNA segments includes the nucleic acid region to be detected.

In embodiments, the method includes:
(i) isolating a genomic DNA including the nucleic acid sequence from a cell or a sample;
(ii) fragmenting the genomic DNA thereby forming a plurality of fragmented genomic DNA segments, where at least one of the fragmented genomic DNA segments includes the nucleic acid region to be detected;
(iii) contacting a nucleic acid sample containing the nucleic acid region (e.g., a plurality of fragmented genomic DNA segments) with a primer (e.g., a 5'-phosphate primer);
(iv) amplifying the nucleic acid region using a first polymerase chain reaction procedure thereby forming a plurality of amplified nucleic acid regions (e.g., 5'-phosphate nucleic acid regions);
(v) ligating a nucleic acid adapter to the plurality of amplified nucleic acid regions (e.g., 5'-phosphate nucleic acid regions) thereby forming a plurality of adapter nucleic acid regions;
(vi) amplifying the plurality of adapter nucleic acid regions using a second polymerase chain reaction procedure thereby forming a plurality of amplified adapter nucleic acid regions;
(vii) attaching the plurality of amplified adapter nucleic acid regions to a separation agent thereby forming a plurality of captured adaptor nucleic acid regions; and
(viii) detecting the captured adapter nucleic acid regions thereby detecting the nucleic acid regions.

In embodiments, the fragmenting is performed by hydroshearing, sonication, nebulization or enzymatic shearing. The terms "hydroshearing," "hydrodynamic shearing" or the like in the context of nucleic acid fragmentation refers, in the usual and customary sense, to the use of hydrodynamic forces (e.g., rapidly moving liquid containing nucleic acid in a confined cross sectional area). The term "sonication" or the like in this context refers to use of acoustic energy to physically shear nucleic acid in solution. The term "nebulization" or the like in this context refers to use of atomized liquid, e.g., using compressed gas, to physically shear nucleic acid in solution. The term "enzymatic shearing" or the like in this context refers to use of enzymes to shear nucleic acid in solution.

In embodiments, the fragmenting is not performed by sonication.

In embodiments, the fragmenting is performed by contacting the genomic DNA with an effective amount of a DNase enzyme (e.g., DNase I or DNase II). In embodiments, fragmented genomic DNA segments are further purified. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents. Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

In embodiments, fragmenting is performed by contacting the genomic DNA with a transposon-transposase complex. In embodiments, the transposase is a MuA transposase, a Mos 1 transposase, a *Vibrio harvey* transposase or a Tn5 transposase, all well known in the art.

The term "transposon" as used herein is a nucleic acid segment that is recognized by a transposase or an integrase enzyme and which is an essential component of a functional nucleic acid-protein complex ("transposome complex") capable of transposition. The inventive transposons in one embodiment belong to class II transposable DNA elements, which use fundamentally similar reactions for their movement within and between genomes, namely, the transposition reaction is catalyzed by a transposase enzyme by either a double- or single-stranded DNA intermediate and transposon DNA is translocated in the "cut and paste" manner within genome. The term "transposon" as used herein also includes all derivatives of the original transposable element, such as mini-transposons or other reiterations of minimal nucleic acid-protein complex capable of transposition, including but not limited to two individual not interconnected transposon ends, or said ends joined by some artificial linker.

The term "transposase" as used herein refers to an enzyme that is a component of a functional nucleic acid-protein complex capable of transposition and that mediates transposition.

The terms "transposon end" or "transposon end" sequencers a sequence recognized by a transposase enzyme necessary to form a synaptic complex or a "transpososome complex", sufficient for a subsequent transposition event to occur in vitro. "Sufficient for a subsequent transposition event to occur in vitro" means transposon end sequences necessary for both recognition and binding of a transposase enzyme, including a terminal stretch of nucleotides of about five base pairs, the last two base pairs being the attacking 5'-CA, these five base pairs necessary for the transposition reaction to occur. A transposon end and transposase protein form a "complex" or a "synaptic complex" or a "transposome complex", the complex capable of inserting or transposing the transposon end into target DNA with which it is incubated in an in vitro transposition reaction. Transpososomes contain multiple subunits of a transposase protein, bound to DNA sequences from both of the transposon's ends. These protein-DNA complexes are also called "synaptic complexes" because they bring together the two ends of the transposon DNA. The phage Mu transposase, MuA, is monomeric in solution but forms a tetramer upon binding to specific DNA recognition sites near the transposon ends. The critical reaction steps mimicking Mu transposition into external target DNA can be reconstituted in vitro using MuA transposase, 50 bp Mu R-end DNA segments, and target DNA as the only macromolecular components (Haapa et al., An efficient and accurate integration of mini-Mu transposons in vitro: A general methodology for functional genetic analysis and molecular biology applications. *Nucleic Acids Res.* 27 (1999) 2777-2784). Additional information about transposon/transposase-mediated genomic DNA fragmenting method can be found in PCT Publication WO 2015/113725, the contents of which is incorporated herein by reference in its entirety.

In embodiments, the fragmented genomic DNA segments are about 100 bp to about 1000 bp in length, e.g., about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 bp.

In embodiments, the fragmented genomic DNA segments are about 100 bp to about 500 bp. In embodiments, the fragmented genomic DNA segments are about 100 bp to about 250 bp. In embodiments, the fragmented genomic DNA segments are about 175 bp to about 375 bp. In embodiments, the fragmented genomic DNA segments are about 250 bp to about 500 bp.

In embodiments, the fragmented genomic DNA segments are about 250 bp to about 750 bp. In embodiments, the fragmented genomic DNA segments are about 250 bp to about 500 bp. In embodiments, the fragmented genomic DNA segments are about 350 bp to about 750 bp.

In embodiments, the fragmented genomic DNA segments are about 500 bp to about 1000 bp. In embodiments, the fragmented genomic DNA segments are about 500 bp to about 750 bp. In embodiments, the fragmented genomic DNA segments are about 625 bp to about 850 bp. In embodiments, the fragmented genomic DNA segments are about 725 bp to about 1000 bp.

In embodiments, the fragmented genomic DNA segments are blunt-ended. The term "blunt ended" or the like in the context of nucleic acid refers, in the usual and customary sense, to a duplex nucleic acid wherein both strands terminate in a base pair, thereby lacking an overhang of one of the strands, as known in the art.

In embodiments, the method further includes ligating a universal adaptor to the plurality of fragmented genomic DNA segments, thereby forming a plurality of universal adaptor fragmented genomic DNA segments.

In embodiments, the method includes:
(i) isolating a genomic DNA including the nucleic acid sequence from a cell or a sample;
(ii) fragmenting the genomic DNA thereby forming a plurality of fragmented genomic DNA segments, where at least one of the fragmented genomic DNA segments includes the nucleic acid region to be detected;
(iii) ligating a universal adaptor to the plurality of fragmented genomic DNA segments, thereby forming a plurality of universal adaptor fragmented genomic DNA segments;
(iv) contacting a nucleic acid sample containing the nucleic acid region (e.g., a plurality of universal adaptor fragmented genomic DNA segments) with a primer (e.g., a 5'-phosphate primer);
(v) amplifying the nucleic acid region using a first polymerase chain reaction procedure thereby forming a plurality of amplified nucleic acid regions (e.g., 5'-phosphate nucleic acid regions);
(vi) ligating a nucleic acid adapter to the plurality of amplified nucleic acid regions (e.g., 5'-phosphate nucleic acid regions) thereby forming a plurality of adapter nucleic acid regions;

(vii) amplifying the plurality of adapter nucleic acid regions using a second polymerase chain reaction procedure thereby forming a plurality of amplified adapter nucleic acid regions;
(viii) attaching the plurality of amplified adapter nucleic acid regions to a separation agent thereby forming a plurality of captured adaptor nucleic acid regions; and
(ix) detecting the captured adapter nucleic acid regions thereby detecting the nucleic acid regions.

In embodiments, both ends of the plurality of fragmented genomic DNA segments are ligated with a universal adaptor. In embodiments, the same universal adaptor is ligated to the both ends of the plurality of fragmented genomic DNA segments. In embodiments, two different universal adaptors are lighted to the two ends of the plurality of fragmented genomic DNA segments. Any methods that are known in the art for ligating an adaptor to a nucleic acid fragment can be used in the methods described herein. In an illustrative embodiment, adaptor ligation is carried out by including the fragmented genomic DNA segments with a universal adaptor (e.g., a P1 adaptor), a dNTP mix, a DNA ligase, and a nick repair polymerase. In embodiments, the ligation reaction is carried out for about 15 minutes at 37° C., followed by about 5 minutes at 72° C. and stored at 4° C.

Any universal adaptors that are designed for high-throughput sequencing can be used in the methods described herein. Exemplary universal adaptors that can be used in the methods described herein include, but are not limited to:

TABLE 1

| Exemplary Universal Adaptors | | SEQ ID |
|---|---|---|
| P1 Adaptor-Up (sense strand) | 5'-CCACTACGCCTCCGCTTTCCTCTCTATGGGCAGTCGGTGA*-3' | 1 |
| P1 Adaptor-Down (anti-sense strand) | 5'-TCACCGACTGCCCATAGAGAGGA*C*C-3' | 2 |
| MuP1 Adaptor primer | 5'-CCACTACGCCTCCGCTTTCCTCTCTATGGGCAGTCGGTGATTTCGTGCGTCAGTTCA-3' | 3 |
| P7 Adapters | | |
| P701 | CAAGCAGAAGACGGCATACGAGATTCGCCTTAGTGACTGGAGTCCTCTCTATGGGCAGTCGGTGA | 4 |
| P702 | CAAGCAGAAGACGGCATACGAGATCTAGTACGGTGACTGGAGTCCTCTCTATGGGCAGTCGGTGA | 5 |
| P703 | CAAGCAGAAGACGGCATACGAGATTTCTGCCTGTGACTGGAGTCCTCTCTATGGGCAGTCGGTGA | 6 |
| P704 | CAAGCAGAAGACGGCATACGAGATGCTCAGGAGTGACTGGAGTCCTCTCTATGGGCAGTCGGTGA | 7 |
| P705 | CAAGCAGAAGACGGCATACGAGATAGGAGTCCGTGACTGGAGTCCTCTCTATGGGCAGTCGGTGA | 8 |
| P706 | CAAGCAGAAGACGGCATACGAGATCATGCCTAGTGACTGGAGTCCTCTCTATGGGCAGTCGGTGA | 9 |
| P707 | CAAGCAGAAGACGGCATACGAGATGTAGAGAGGTGACTGGAGTCCTCTCTATGGGCAGTCGGTGA | 10 |
| P708 | CAAGCAGAAGACGGCATACGAGATCCTCTCTGGTGACTGGAGTCCTCTCTATGGGCAGTCGGTGA | 11 |
| P5 Adapters Sequence (5'→3') | | |
| P5_1 | AATGATACGGCGACCACCGAGATCTA | 12 |
| P5_2 | AATGATACGGCGACCACCGAGATCTACAC | 13 |
| Adapters 1-16 (with Molecular Index tag NNWNNWNN) | | |
| MISEQ® Common Adapter | [Phos]GATCGGAAGAGC*C*A | 14 |
| A01 | AATGATACGGCGACCACCGAGATCTACACTAGATCGCNNWNNWNNACACTCTTTCCCTACACGACGCTCTTCCGATC | 15 |
| A02 | AATGATACGGCGACCACCGAGATCTACACCTCTCTATNNWNNWNNACACTCTTTCCCTACACGACGCTCTTCCGATC*T | 16 |
| A03 | AATGATACGGCGACCACCGAGATCTACACTATCCTCTNNWNNWNNACACTCTTTCCCTACACGACGCTCTTCCGATC*T | 17 |
| A04 | AATG ATACGGCGACCACCG AGATCTACACAGAGTAGAN NWN NWN N ACACTCTTTCCCTACACGACGCTCTTCCGATC*T | 18 |
| A05 | AATGATACGGCGACCACCGAGATCTACACGTAAGGAGNNWNNWNNACACTCTTTCCCTACACGACGCTCTTCCGATC*T | 19 |

TABLE 1-continued

| | Exemplary Universal Adaptors | SEQ ID |
|---|---|---|
| A06 | AATGATACGGCGACCACCGAGATCTACACACTGCATANNWNNWNNAC ACTCTTTCCCTACACGACGCTCTTCCGATC*T | 20 |
| A07 | AATGATACGGCGACCACCGAGATCTACACAAGGAGTANNWNNWNNAC ACTCTTTCCCTACACGACGCTCTTCCGATC*T | 21 |
| A08 | AATGATACGGCGACCACCGAGATCTACACCTAAGCCTNNWNNWNNAC ACTCTTTCCCTACACGACGCTCTTCCGATC*T | 22 |
| A09 | AATG ATACGGCGACCACCG AGATCTACACGACATTGTN N WN N ACACTCTTTCCCTA CACGACGCTCTTCCGATC*T | 23 |
| A10 | AATGATACGGCGACCACCGAGATCTACACACTGATGGNNWNNWNNAC ACTCTTTCCCTACACGACGCTCTTCCGATC*T | 24 |
| A11 | AATGATACGGCGACCACCGAGATCTACACGTACCTAGNNWNNWNNAC ACTCTTTCCCTACACGACGCTCTTCCGATC*T | 25 |
| A12 | AATGATACGGCGACCACCGAGATCTACACCAGAGCTANNWNNWNNAC ACTCTTTCCCTACACGACGCTCTTCCGATC*T | 26 |
| A13 | AATGATACGGCGACCACCGAGATCTACACCATAGTGANNWNNWNNAC ACTCTTTCCCTACACGACGCTCTTCCGATC*T | 27 |
| A14 | AATGATACGGCGACCACCGAGATCTACACTACCTAGTNNWNNWNNAC ACTCTTTCCCTACACGACGCTCTTCCGATC*T | 28 |
| A15 | AATGATACGGCGACCACCGAGATCTACACCGCGATATNNWNNWNNAC ACTCTTTCCCTACACGACGCTCTTCCGATC*T | 29 |
| A16 | AATGATACGGCGACCACCGAGATCTACACTGGATTGTNNWNNWNNAC ACTCTTTCCCTACACGACGCTCTTCCGATC*T | 30 |

In embodiments, the method further includes contacting the plurality of universal adaptor fragmented genomic DNA segments with a primer complementary to the universal adaptor and a primer complementary to the nucleic acid region, and then amplifying the universal adaptor fragmented genomic DNA sequences using a polymerase chain reaction procedure, thereby forming a plurality of amplified universal adapter fragmented genomic DNA segments.

In embodiments, the method includes:
(i) isolating a genomic DNA including the nucleic acid sequence from a cell or a sample;
(ii) fragmenting the genomic DNA thereby forming a plurality of fragmented genomic DNA segments, where at least one of the fragmented genomic DNA segments includes the nucleic acid region to be detected;
(iii) ligating a universal adaptor to the plurality of fragmented genomic DNA segments, thereby forming a plurality of universal adaptor fragmented genomic DNA segments;
(iv) contacting the plurality of universal adaptor fragmented genomic DNA segments with a primer complementary to the universal adaptor and a primer (primer 1) complementary to the nucleic acid region;
(v) amplifying the universal adaptor fragmented genomic DNA sequences using a polymerase chain reaction procedure, thereby forming a plurality of amplified universal adapter fragmented genomic DNA segments;
(vi) contacting a nucleic acid sample containing the nucleic acid region (e.g., a plurality of amplified universal adapter fragmented genomic DNA segments) with a primer (e.g., a 5'-phosphate), where the primer (e.g., a 5'-phosphate primer) is complementary to the nucleic acid region and the 5'-phosphate primer is a nested primer of the primer 1;

(vii) amplifying the nucleic acid region using a first polymerase chain reaction procedure thereby forming a plurality of amplified nucleic acid regions (e.g., 5'-phosphate nucleic acid regions);
(viii) ligating a nucleic acid adapter to the plurality of amplified nucleic acid regions (e.g., 5'-phosphate nucleic acid regions) thereby forming a plurality of adapter nucleic acid regions;
(ix) amplifying the plurality of adapter nucleic acid regions using a second polymerase chain reaction procedure thereby forming a plurality of amplified adapter nucleic acid regions;
(x) attaching the plurality of amplified adapter nucleic acid regions to a separation agent thereby forming a plurality of captured adapter nucleic acid regions; and
(xi) detecting the captured adapter nucleic acid regions thereby detecting the nucleic acid regions.

In embodiments, the adaptor is a barcode adaptor. The term "barcode" or the like in this context refers, in the usual and customary sense, to sequences of nucleotides, biomolecule components and/or subunits, or polymer component and/or subunits that are used for sample discriminating codes. In embodiments, a sample discriminating code or barcode may correspond to a sequence of individual nucleotides in a nucleic acid or subunits of a biomolecule or polymer or to sets, groups, or continuous or discontinuous sequences of such nucleotides or subunits. In embodiments, a sample discriminating code or barcode may also correspond to or with (whether directly or indirectly) transitions between nucleotides, biomolecule subunits, or polymer subunits, or other relationships between subunits forming a sample discriminating code or barcode.

In embodiments, sample discriminating codes or barcodes may have properties that permit them to be read, or otherwise recognized, identified, or interpreted with improved accuracy and/or reduced error rates for a given code type, length, or complexity.

Any barcode adaptors known in the art can be used in the methods described herein. In embodiments, the methods described herein utilize barcode adaptors that can be ligated to a 5'-phosphate nucleic acid region. Exemplary barcode adaptors that can be used in the methods described herein include, but are not limited to,

TABLE 2

| Exemplary Barcode Adaptors | | SEQ ID |
|---|---|---|
| BC-A adaptor-Up (sense strand) | 5'-CATCTCATCCCT*G*CGTGTCTCCGACT CAGNNNNNNNNNNNGAT-3' | 31 |
| BC-A adaptor-Down (anti-sense strand) | 5'-ATCGTTACCTTAGCTGAGTCGGAGACAC GC-3' | 32 |

Additional information about barcode and barcode adaptors and additional examples of barcode adaptors can be found in U.S. Pat. Publ. 2013/0053256, the contents of which are incorporated herein as their entireties.

In embodiments, a primer that is complementary to the adaptor (i.e., the barcode adaptor) is used to amplify the plurality of adapter nucleic acid regions of the methods described herein uses. In embodiments, the primer includes a spacer region. As defined above, the spacer region can optionally include one or more modified nucleotides or one or more non-nucleotidyl moieties that prevent the extension during PCR. Hence, each of the amplified barcode adapter nucleic acid regions comprises a single strand tail on both 5' and 3' ends because of the use of the spacer region in the primer (also called A-tail primer). Additional information about the design of A-tail primer can be found in U.S. Pat. No. 9,133,510, the contents of which is incorporated herein by reference in its' entirety.

Any spacer modifications known in the art can be included in the primer that is complementary to the barcode adaptor. Exemplary spacer region that can be used includes, but is not limited to:

In embodiments, methods described herein utilize one or more separation agents for capturing and/or enriching the amplified barcode adaptor nucleic acid regions. In embodiments, the separation agent is covalently linked to an oligonucleotide sequence that is complementary to the single strand of the amplified barcode adaptor nucleic acid regions. In embodiments, the separation agent is attached to each of the amplified barcode adaptor nucleic acid regions by contacting the amplified barcode adaptor nucleic acid regions with the separation agent, thereby forming a plurality of captured adaptor nucleic acid regions.

As used herein, "separation agent" and its variants may include one molecule of a binding partner that can capture and enrich a specific pool of nucleic acid sequences (e.g., amplified barcode adaptor nucleic acid regions). As used herein, the term "binding partners" includes two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions.

In embodiments, molecules that function as binding partners include: biotin (and its derivatives) and their binding partner avidin moieties, streptavidin moieties (and their derivatives); His-tags which bind with nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; Protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen et al., *BMC Structural Biology* 7:8).

TABLE 3

| Exemplary Spacer Regions | |
|---|---|
| C3 spacer | The C3 Spacer phosphoramidite can be incorporated internally or at the 5'-end of the oligo. Multiple C3 spacers can be added at either end of an oligo to introduce a long hydrophilic spacer arm for the attachment of fluorophores or other pendent groups. |
| PC spacer | PC (Photo-Cleavable) Spacer can be placed between DNA bases or between the oligo and a 5'-modifier group. It offers a 10-atom spacer arm which can be cleaved with exposure to UV light in the 300-350 nm spectral range. Cleavage releases the oligo with a 5'-phosphate group. |
| hexanediol | Hexanediol is a six carbon glycol spacer that is capable of blocking extension by DNA polymerases. This 3' modification is capable of supporting synthesis of longer oligos. |
| Spacer 9 | Spacer 9 is a triethylene glycol spacer that can be incorporated at the 5'-end or 3'-end of an oligo or internally. Multiple insertions can be used to create long spacer arms. |
| Spacer 18 | Spacer 18 is an 18-atom hexa-ethyleneglycol spacer. It is the longest spacer arm that can be added as a single modification. |
| 1',2'-Dideoxyribose (dSpacer) | The 1',2'-Dideoxyribose modification is used to introduce a stable abasic site within an oligonucleotide. |

An avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g., nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products EXTRAVIDIN™, CAPTAVIDIN™, NEUTRAVIDIN™ and NEUTRALITE AVIDIN™.

In embodiments, the oligonucleotide sequence covalently linked to the separation agent is biotinylated.

In embodiments, the separation agent includes a support. In embodiments, a "support" comprises a planar surface, as well as concave, convex, or any combination of surfaces thereof. In embodiments, a "support" includes a bead, particle, microparticle, sphere, filter, flowcell, well, microwell, groove, channel reservoir, gel or inner wall of a capillary. In embodiments, the support includes the inner walls of a capillary, a channel, a well, microwell, groove, channel, reservoir. In embodiments, the support includes include texture (e.g., etched, cavitated, pores, three-dimensional scaffolds or bumps). In embodiments, the support can be porous, semi-porous or non-porous. In embodiments, the support includes one or more beads having cavitation or pores, or can include three-dimensional scaffolds. In embodiments, the support includes an ION SPHERE™ particle (from Ion Torrent, part of Life Technologies, Carlsbad, California). In embodiments, the particles have any shape including spherical, hemispherical, cylindrical, barrel-shaped, toroidal, rod-like, disc-like, conical, triangular, cubical, polygonal, tubular, wire-like or irregular. In embodiments, the support can be made from any material, including glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). In embodiments, the support can be magnetic or paramagnetic. In embodiments, the support includes paramagnetic beads attached with streptavidin (e.g., DYNABEADS™ M-270 from Invitrogen, Carlsbad, CA). In embodiments, the bead or particle can have an iron core, or comprise a hydrogel or agarose (e.g., SEPHAROSE™). In embodiments, the support is coupled to at least one sensor that detects physicochemical byproducts of a nucleotide incorporation reaction, where the byproducts include pyrophosphate, hydrogen ion, charge transfer, or heat. In embodiments, the support includes a magnetic bead.

In embodiments, the detecting the captured barcode adaptor nucleic acid regions includes sequencing the captured adaptor nucleic acid sequences.

Any method of sequencing can be used in the present methods, including chain terminator (Sanger) sequencing and dye terminator sequencing. In embodiments, Next Generation Sequencing (NGS), a high-throughput sequencing technology that performs thousands or millions of sequencing reactions in parallel, is used. Although the different NGS platforms use varying assay chemistries, they all generate sequence data from a large number of sequencing reactions run simultaneously on a large number of templates. Typically, the sequence data is collected using a scanner, and then assembled and analyzed bioinformatically. Thus, the sequencing reactions are performed, read, assembled, and analyzed in parallel (see, e.g., U.S. Patent Publ. 2014/0162897, as well as Voelkerding et al., *Clinical Chem.*, 55:641-658 (2009); and MacLean et al., *Nature Rev. Microbiol.*, 7:287-296 (2009)). Some NGS methods require template amplification and some that do not. Amplification-requiring methods include pyrosequencing (see, e.g., U.S. Pat. Nos. 6,210,891 and 6,258,568; commercialized by Roche); the SolexaIJLLuMINA® platform (see, e.g., U.S. Pat. Nos. 6,833,246; 7,115,400; and 6,969,488); and the Supported Oligonucleotide Ligation and Detection (SOLiD) platform (Applied Biosystems; see, e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476,503). See, e.g., U.S. Pat. Publ. 2013/0274147; U.S. Pat. Publ. 2014/0038831; Metzker, *Nat. Rev. Genet.* 11(1):31-46 (2010). Alternatively, hybridization-based sequence methods or other high-throughput methods can also be used, e.g., microarray analysis, NANOSTRING, ILLUMINA®, or other sequencing platforms.

In embodiments, the sequencing is a next-generation sequencing. The term "next generation sequencing" or the like refers, in the usual and customary sense, to high-throughput DNA sequencing technologies which are not based on the classic work of Sanger, as well known in the art.

In embodiments, the next generation sequencing platform used herein is an Ion Torrent platform. Further details regarding the compositions, design and operation of the ION PGM™ sequencer can be found, for example, in U.S. Patent Publication No. 2009/0026082; U.S. Patent Publication No. 2010/0137143; and U.S. Patent Publication No. 2010/0282617, all of which applications are incorporated by reference herein in their entireties. Various library preparation methods and kits exist within the NGS field that allow for the preparation of multiple target nucleic acid molecules from a single source (ION AMPLISEQ™ Library Preparation, Publication Part Number: MAN0006735 or ION XPRESS™ Plus gDNA Fragment Library Preparation, Publication Part Number 4471989 (Life Technologies, CA); NEBNEXT® Fast DNA Library Prep Set for Ion Torrent, New England Biolabs Catalog No. E6270L). The advent of barcoding has expanded this functionality by allowing the indexing of multiple target nucleic acid molecules from multiple samples or sources in a single sequencing run (ION XPRESS™ Barcode Adaptors 1-96 for use with ION XPRESS™ Plus Fragment Library Kit (Life Technologies, CA); ACCESS ARRAY™ Barcode Library, Fluidigm Corp, CA). Some areas of NGS, such as targeted re-sequencing, typically utilize many samples prepared in parallel, for example in several 96-well plates. The starting amounts of barcoded and non-barcoded nucleic acid libraries prepared using known library preparation methods vary widely and thus must be individually quantified before being transitioned into downstream processes. Quantification of target nucleic acid libraries can be achieved using a variety of protocols, including qPCR, Qubit® Fluorometer (Life Technologies, CA) and BIOANALYZER™ (Agilent Technologies, CA).

In an aspect provided herein are methods for detecting off-target insertion of nucleic acid into the genome of a cell. The methods include those involving contacting the cell with at least one gene editing reagent and at least one donor nucleic acid molecule under conditions that allow for the generation of a double stranded break at a predetermined genetic locus. These methods may further include collecting nucleic acid from the cell of a previous step to generate a nucleic acid sample. These methods may further include contacting the nucleic acid sample containing the nucleic acid region with a primer (e.g., a 5'-phosphate primer). These methods may further include amplifying the nucleic acid region using a first polymerase chain reaction procedure thereby forming a plurality of amplified nucleic acid regions (e.g., 5'-phosphate nucleic acid regions). These methods may further include ligating nucleic acid adapters to the plurality of amplified nucleic acid regions (e.g., 5'-phosphate nucleic acid regions) thereby forming a plurality of adapter nucleic acid regions. These methods may further include amplifying the plurality of adapter nucleic acid regions using a second polymerase chain reaction procedure thereby forming a plurality of amplified adapter nucleic acid regions. These methods may further include attaching the plurality of amplified adapter nucleic acid regions to a separation agent thereby forming a plurality of captured adaptor nucleic acid regions. These methods may further include detecting the captured adaptor nucleic acid regions thereby detecting the nucleic acid region.

In embodiments of such methods, the gene editing reagents may include one or more zinc finger-FokI fusion protein, one or more TAL nuclease, one of more CRISPR-nucleic acid complex, or one or more argonaute-nucleic acid complex.

Compositions and Kits

Another aspect provided herein is a collection of reagents. The collection includes at least primer (e.g., one 5'-phosphate primer) and at least one barcode adaptor. In embodiments, the at least one 5'-phosphate primer is complementary to the nucleic acid region to be detected by the methods described herein. Exemplary barcode adaptor includes, but is not limited to, those listed in Table 2.

In embodiments, the collection of reagents further includes at least one primer that is complementary to the barcode adaptor. In embodiments, the primer that is complementary to the barcode adaptor includes a spacer region. In embodiments, the collection includes at least one 5'-phosphate primer, at least one barcode adaptor and at least one primer that is complementary to the barcode adaptor.

In embodiments, the collection of reagents also includes a separation agent. In embodiments, the collection includes at least one 5'-phosphate primer and at least one barcode adaptor and a separation agent. In embodiments, the separation agent includes a support. In embodiments, the support includes a magnetic bead.

In embodiments, the collection of reagents also includes a DNase (e.g., DNase I or DNase II). In embodiments, the collection includes at least one 5'-phosphate primer and at least one barcode adaptor and a DNase (e.g., DNase I or DNase II). In embodiments, the collection of reagents also includes an ION SHEAR™ Plus Enzyme Mix. In embodiments, the collection includes at least one 5'-phosphate primer and at least one barcode adaptor and an ION SHEAR™ Plus Enzyme Mix.

In embodiments, the collection of reagents also includes a transposon-transposase complex. In embodiments, the collection includes at least one 5'-phosphate primer and at least one barcode adaptor and a transposon-transposase complex. In embodiments, the collection of reagents also includes a MuSeek Enzyme Mix. In embodiments, the collection includes at least one 5'-phosphate primer and at least one barcode adaptor and a MuSeek Enzyme Mix.

In embodiments, the collection of reagents also includes at least one universal adaptor. Exemplary universal adaptor includes, but is not limited to, those in Table 1. In embodiments, the collection includes at least one 5'-phosphate primer and at least one barcode adaptor and at least one universal adaptor.

In embodiments, the collection of reagents also includes at least one primer that is complementary to the universal adaptor. In embodiments, the collection includes at least one 5'-phosphate primer and at least one barcode adaptor and at least one universal adaptor and at least one primer that is complementary to the universal adaptor.

In embodiments, the collection of reagents also includes at least one primer for sequencing. In embodiments, the collection includes at least one 5'-phosphate primer and at least one barcode adaptor and at least one primer for sequencing.

In embodiments, the collection of reagents includes at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, and at least one primer for sequencing.

In embodiments, the collection of reagents can also include one or more of the following reagents: beads for purifying nucleic acid, dNTP mix, DNA ligase, nick repair polymerase, PHUSION® Hot Start II High-Fidelity DNA Polymerase (Thermo Fisher Scientific, cat. no. F549L) and one or more primers in Table 4.

In embodiments, the collection of reagents includes at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the collection of reagents includes genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, a donor nucleic acid molecule may include an insert sequence to the DSB created by an engineered nuclease. In embodiments, a donor nucleic acid molecule may include a foreign genome or a fragment thereof. In embodiments, a donor nucleic acid molecule may include a translocated genomic sequence or a fragment thereof. In embodiments, a donor nucleic acid molecule may include a nucleic acid encoding an antibody sequence.

In embodiments, the collection of reagents includes fragmented genomic segments of genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the collection of reagents includes universal adaptor fragmented genomic segments prepared from the genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the collection of reagents includes amplified 5'-phosphate nucleic acid regions prepared from the genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the collection of reagents includes adaptor 5'-phosphate nucleic acid regions prepared from the genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the collection of reagents includes amplified adaptor 5'-phosphate nucleic acid regions prepared from the genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the collection of reagents includes capture adaptor 5'-phosphate nucleic acid regions prepared from the genomic DNA isolated from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the reagents in the collections described herein are within one or more (e.g., 1, 2, 3, 4, 5, 6, 7, 8, 9, 10, 11, 12, 13, 14, 15, 16, 17, 18, 19, 20 or more) vessels. In embodiments, the reagents in the collections described herein are in different vessels. In embodiments, some of the reagents in the collections described herein are in the same vessels. In embodiments, one or more of the vessels includes storage medium or reaction buffer.

In embodiments, the term "at least one" (for example, at least one 5'-phosphate primer, at least one barcode adaptor, at least one primer that is complementary to the barcode adaptor, at least one universal adaptor, at least one primer that is complementary to the universal adaptor, at least one primer for sequencing) used herein means 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400 or more.

One aspect provided herein is a kit. The kit includes at least one (e.g., 1, 2, 3, 4, 5, 6, 7, 8, 9, 10 or more) instruction and any of the collections of the reagents described herein.

Another aspect provided herein is a kit that includes at least one instruction, at least one 5'-phosphate primer and at least one barcode adaptor. In embodiments, the at least one 5'-phosphate primer is complementary to the nucleic acid region to be detected by the methods described herein. Exemplary barcode adaptor includes, but is not limited to, those listed in Table 2.

In embodiments, the at least one 5'-phosphate primer is within a first vessel, and the at least one nucleic acid adaptor is within a second vessel. In embodiments, the first vessel and the second vessel are the same vessel.

In embodiments, the kit also includes at least one primer that is complementary to the barcode adaptor. In embodiments, the primer that is complementary to the barcode adaptor includes a spacer region. Any spacer region known in the art can be used.

In embodiments, the kit further includes at least one primer that is complementary to the barcode adaptor. In embodiments, the primer that is complementary to the barcode adaptor includes a spacer region. In embodiments, the kit includes at least one 5'-phosphate primer and at least one barcode adaptor and at least one primer that is complementary to the barcode adaptor.

In embodiments, the kit also includes a separation agent. In embodiments, the kit includes at least one 5'-phosphate primer and at least one barcode adaptor and a separation agent. In embodiments, the separation agent includes a support. In embodiments, the support includes a magnetic bead.

In embodiments, the kit also includes a DNase (e.g., DNase I or DNase II). In embodiments, the kit includes at least one 5'-phosphate primer and at least one barcode adaptor and a DNase (e.g., DNase I or DNase II). In embodiments, the kit also includes an ION SHEAR™ Plus Enzyme Mix. In embodiments, the kit includes at least one 5'-phosphate primer and at least one barcode adaptor and an ION SHEAR™ Plus Enzyme Mix.

In embodiments, the kit also includes a transposon-transposase complex. In embodiments, the kit includes at least one 5'-phosphate primer and at least one barcode adaptor and a transposon-transposase complex. In embodiments, the kit also includes a MuSeek Enzyme Mix. In embodiments, the kit includes at least one 5'-phosphate primer and at least one barcode adaptor and a MuSeek Enzyme Mix.

In embodiments, the kit also includes at least one universal adaptor. Exemplary universal adaptor includes, but is not limited to, those in Table 1. In embodiments, the kit includes at least one 5'-phosphate primer and at least one barcode adaptor and at least one universal adaptor.

In embodiments, the kit also includes at least one primer that is complementary to the universal adaptor. In embodiments, the kit includes at least one 5'-phosphate primer and at least one barcode adaptor and at least one universal adaptor and at least one primer that is complementary to the universal adaptor.

In embodiments, the kit also includes at least one primer for sequencing. In embodiments, the kit includes at least one 5'-phosphate primer and at least one barcode adaptor and at least one primer for sequencing.

In embodiments, the kit includes at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, and at least one primer for sequencing.

In embodiments, the kit can also include one or more of the following reagents: beads for purifying nucleic acid, dNTP mix, DNA ligase, nick repair polymerase, PHUSION® Hot Start II High-Fidelity DNA Polymerase and one or more primers in Table 4.

In embodiments, the kit includes at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the kit includes reagents for isolating genomic DNA from cells that have been contacted a donor nucleic acid molecule under a condition that is suitable for the integration of the donor nucleic acid molecule into the genome DNA of the cells, where the donor nucleic acid molecule has been integrated to the genomic DNA of the cells, and at least one 5'-phosphate primer and at least one barcode adaptor and optionally one or more of the following: at least one primer complementary to the barcode adaptor, a separation agent, a DNase, a transposon-transposase complex, at least one universal adaptor, at least one primer complementary to the universal adaptor, at least one primer for sequencing, beads for purifying nucleic acid, dNTP mix, DNA ligase, nick repair polymerase, PHUSION® Hot Start II High-Fidelity DNA Polymerase and one or more primers in Table 4.

In embodiments, the term "at least one" (for example, at least one 5'-phosphate primer, at least one barcode adaptor, at least one primer that is complementary to the barcode adaptor, at least one universal adaptor, at least one primer that is complementary to the universal adaptor, at least one primer for sequencing) used herein means 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400 or more.

EXAMPLES

Example 1. Detection and Localization of Targeted Nucleic Acid Sequence Integrated or Pre-Existed in Genome Rationale. Nucleic acid sequences (tags/regions) can be site-specifically or randomly integrated to different loci of genome in any cells/animals through transfection or infection. The sequence tag can be artificially synthesized oligos or large piece of virus DNA/RNA or plasmid containing monoclonal antibody for bio-production, or nature DNA/chromosome translocated from different loci. Accordingly, quick and highly-sensitive detection and localization method for specific tags in genome can be very useful for many applications, e.g., CRRIPR-cas9 genome-wide off-target detection, understanding viral infection-related diseases, high-stable expression mAb bio-production and DNA/chromosome translocation study.

Without wishing to be by any theory, it is believed that the following steps are required to detect and localize the tag: 1. Fragmentation of genomic DNA; 2. Amplification of tag-contained fragments; 3. Adaptation of NGS (Next Generation Sequencing) sequences to both sides of amplicon; and 4. NGS and data analysis to detect and localize tag.

Introduction.

CRISPR-Cas9 has been broadly used for different applications that rely on a RNA-guided nuclease (RGN) to create a DNA double strand break (DSB) in cells followed by non-homologous end joining (NHEJ) for gene knock out, or DNA donor integration for gene correction through homology directed repair (HDR). However, the potential therapeutic application will require a comprehensive knowledge of their off-target effects to minimize the risk of deleterious outcomes. Several in vivo or in vitro methods have been developed to detect off-target (Wang, et al. (2015); Frock, et al. (2015); Crosetto, et al. (2013)). Most of methods rely on an integration of viral DNA (Wang, et al. (2015)) or short double strand DNA tag (Wang, et al. (2015); Frock, et al. (2015)) into the DSB followed by PCR amplification and NGS. These methods can only detect partial off-targets due to DNA tag degradation in cells, led to the low efficiency of tag integration in DSB. Recently, a method of "Genome-wide, Unbiased Identification of DSBs Enabled by sequencing" (GUIDE-seq) was developed in Keith Joung's lab and used phosphorothioate-modified double strand DNA as tag that prevented degradation and increased integration efficiency of tag into DSB in cells (Tsai, et al., (2015)). After the tag integrated in DSB of genome, the DNA sample can be sheared, e.g., by sonication. With an adapter ligated to both ends of DNA fragments, the tagged targeting fragments can be amplified with two rounds of PCR using tag- and adapter-specific primers in two opposite directions, followed by one round of PCR using the primers containing sequencing primers.

After performed many different tests, we found the GUIDE-seq method still affords limitations and issues following: (1) DNA fragmentation using sonication limits high throughput application and requires sonication methodology; and (2) a major issue is the non-specific (non-targeting) PCR amplification that causes a high background and requires more deep sequencing to detect the low frequent (<0.1%) DSB that was discussed in the publication (5).

To solve the first issue, we modified the gDNA fragmentation method by using enzyme-based ION SHEAR™ (6) or transposase-based MuSeek (7) that are optimized for Ion-NGS (FIG. 1).

For the second issue of non-specific amplification, without wishing to be bound by any theory, it is believed that it was mainly caused by amplification of adaptor primer (P1) ligated to both ends of DNA fragments. After gDNA fragmentation, only a small fraction (less than 1%) of fragments contains the tag. The majority (more than 99%) of DNA fragments does not contain the tag, but could be amplified by P1/P1 primer resulting in excessive non-specific products over the specific product of P1 and tag specific primers (F1 and R1). We found that only small percentage of NGS reads from the sample prepared above were the tag-containing targeting sequences.

To solve this problem, we first changed tag-specific primers (F2 and R2) by adding a phosphate at 5' end of primers (5P-F2 and 5P-R2). So, only the tag contained product of P1/5P-F2 and P1/5P-R2 from $2^{nd}$ round PCR contains a phosphate at 5' ends, but not P1/P1 product. Then, a barcode adaptor A (BC-A), which is needed for Ion-Torrent NGS, was ligated to a second PCR product. In this case, only the tag-containing PCR product have 5'P and can be ligated with "BC-A" adaptor. The P1/P1 product that does not contain 5'P cannot be ligated with "BC-A" adaptor. We then performed a third round of PCR using P1 and "A-tail" primer that contains a modified nucleotide in the middle of the primer to stop polymerase extension, which leaves a single strand at the tail of $3^{rd}$ PCR product (FIG. 1). We then use a biotinylated oligo that is complementary to the tail of "A-tail" primer to enrich A/P1 product using streptavidin beads for Ion-Torrent NGS. Streptavidin can bind to biotin which is added at 3' end of Capture oligo (see Table 4). So, the specific A-P1 amplicons (A-P1 PCR product in Step 4 of FIG. 1) are captured by biotinylated Capture oligo, and separated (enriched) from the rest of non-specific amplicons through magnetic bead.

Exemplary oligonucleotide sequences are set forth in Table 4 following.

TABLE 4

Oligonucleotide sequences.

| Name of Oligo | Sequence | SEQ ID |
|---|---|---|
| P1 Adaptor-Up | 5'-CCACTACGCCTCCGCTTTCCTCTCTATGGGCAGTCGGTGA*-3' | 33 |
| P1 Adaptor-Down | 5'-TCACCGACTGCCCATAGAGAGGA*C*C-3' | 34 |
| MuP1 Adaptor primer | 5'-CCACTACGCCTCCGCTTTCCTCTCTATGGGCAGTCGGTGATTTCGTGCGTCAGTTCA-3' | 35 |
| P1 primer | 5'-CCACTACGCCTCCGCTTTCCTCTCTATG-3' | 36 |
| F1 primer | 5'-GTTTAATTGAGTTGTCATATGTTAAT-3' | 37 |
| R1 primer | 5'-ATACCGTTATTAACATATGACAACTC-3' | 38 |
| 5p-F2 primer | 5'-PHO-GTTGTCATATGTTAATAACGGTAT-3' | 39 |
| 5p-R2 primer | 5'-PHO-TAACATATGACAACTCAATTAAAC-3' | 40 |
| BC-A adaptor-Up | 5'-CCATCTCATCCCT*G*CGTGTCTCCGACTCAGNNNNNNNNNNGAT-3' | 41 |
| BC-A adaptor-Down | 5'-ATCGTTACCTTAGCTGAGTCGGAGACACGC-3' | 42 |
| Equalizer A Primer | 5'-GGGAAAAGATGG/iSp18/CCATCTCATCCCTGCGTGTC-3' | 43 & 243 |
| Equalizer P1-Primer | 5'-CCACTACGCCTCCGCTTTCCTCTCTATG-3' | 44 |
| Capture oligo | 5'-CCATCTTTTCCC/3BioTEG/ | 45 |

G*, T*, A* and C* represent phosphorothioate linkage at N 3' end; NNNNNNNNNN (Seq ID No. 46) is barcode sequence Protocol.

Protocols for conducting the methods disclosed herein include Steps 1-4 following. As a general rule, the symbol "*" used in the protocol represent the unit minute, and the symbol """ used in the protocol represents the unit second.

Step 1. gDNA Fragmentation and Adaptor*Ligation Using Ion-Shear (1.1) or MuSeek (1.2):

| Option 1.1. ION SHEAR™ for gDNA fragmentation | 1x (µl) |
|---|---|
| ION SHEAR™ Plus 10X Buffer | 5 |
| gDNA (121ng/µl) | 5 |
| H₂O | 35 |
| ION SHEAR™ Plus Enzyme Mix | 5 |
| | 50 |
| 37°C, | 8' |
| Stop buffer | 5 |
| Total | 55 |

Purification using AMPURE® Beads (warm up at RT for 10')

Beads (1.8x sample volume) — 99

Mix 5x, 5 mins. at RT, MagSep it, remove supernatant 2x wash with 500µl 70% ethanol while on the Mag and move beads side to side Elute in Low TE (µl) — 25

| P1 (or any) Adapters Ligation | 1x (µl) |
|---|---|
| sheared DNA | 10 |
| 10X Ligase Buffer (µL) | 5 |
| P1 adaptor (µL) | 2 |
| dNTP Mix (µL) | 1 |
| Nuclease-free Water 51 µL 41 µL | 26 |
| DNA Ligase (µL) | 2 |
| Nick Repair Polymerase (µL) | 4 |
| Total (µL) | 50 |

Incubate at 15 min at 37°C, 5 min at 72°C and hold at 4°C

Purification by using AMPURE® beads:

Beads (1.5x sample volume)

Mix 5x, 5' at RT, MagSep it, remove sup

2xwash with 500 µl 70% ethanol while on the Mag and move beads side to side

Elute in 25 µl Low TE

| Option 1.2. MuSeek for gDNA Fragmentation | 1x30 |
|---|---|
| MuSeek Fragmentation Buffer* | 10 |
| gDNA (121ng/µl) | 1 |
| MuSeek Enzyme Mix (kept at -70° C) | 1 |

| | |
|---|---|
| H₂O | 18 |
| Total | 30 |

Mix gently to avoid foaming
5' at 30° C water bath

| | |
|---|---|
| MuSeek Stop Buffer | 3 |
| Total | 33 |

Brief vortex and keep it at RT

Purification:
AMPURE® beads in 1.5ml tube:
Warm up beads at RT for 30min

| | |
|---|---|
| Beads (1.5xsample volume) | 49.5 |
| Total | 82.5 |

Mix 10x, 5' at RT, MagSep it, remove sup
2xwash with 400µl 70% ethanol while on the Mag, move beads side to side
Dry beads at RT for 2'
Resuspend beads in H₂O            25
Run 7.5µl+7.5µl on 1% EXgel

| Adding MuP1 Adaptor | 1x100 |
|---|---|
| 5x Adaptor Add Rea Buffer | 20 |
| MuP1 primer Mix (MuP1+P1) | 2 |
| Purified fragmented gDNA | 10 |
| Phusion Hot Start II FH polymerase | 1 |
| H₂O | 67 |
| Total | 100 |

| | Temp | Time |
|---|---|---|
| | 66°C | 3' |
| | 98°C | 30" |
| | 98°C | 10" |
| MuSeek-1 program | 60°C | 50" |
| | 72°C | 10" |
| | 72°C | 1' |
| | 4°C | Hold |

Purification:
AMPURE® beads in 1.5ml tube:

| | |
|---|---|
| MuP1-DNA PCR product | 100 |
| Warm up beads at RT for 30min | |
| Beads (1.8xsample volume) | 180 |
| Total | 280 |

Mix 10x, 5' at RT, MagSep it, remove supernatant
2xwash with 400 µl 70% ethanol while on the Mag and move beads side to side
Dry beads at RT for 2 minutes

| | |
|---|---|
| Resuspend beads in H$_2$O | 20 |

* Ion Compatible MuSeek Library Preparation Kit (Thermo Fisher Scientific, cat. no. K1331)

[00227] Step 2. PCR Amplification:

| 1st PCR | Forward | Reverse |
|---|---|---|
| 5x ION AMPLISEQ™ HiFi Mix (red cap) | 5 | 5 |
| P1-24-8' | 4 | 4 |
| P1-24-12' | | |
| 5xP1 primer (1μM) | 4 | 4 |
| 5xF1 primer (1μM) | 4 | |
| 5xR1 primer (1μM) | | 4 |
| H$_2$O | 8 | 8 |
| Total | 25 | 25 |

Ampliseq-1

| Temp | Time | Cycles |
|---|---|---|
| 99°C | 2' | 1 |
| 99°C | 15" | |
| 60°C | 60" | 17 |
| 60°C | 5' | 1 |
| 4°C | Hold | |

| 2$^{nd}$ PCR | Forward | Reverse |
|---|---|---|
| 5xPhusion Green HF Buffer | 5 | 5 |
| 10mM dNTP | 0.5 | 0.5 |
| 100%DMSO | 0.75 | 0.75 |
| Phusion HF | 0.25 | 0.25 |
| 5xP1 primer (1μM) | 4 | 4 |
| H$_2$O | 8.5 | 8.5 |
| Sub Total | 19 | 19 |
| 1st PCR 8' | 2 | 2 |
| 5x 5P_F2 (1μM) | 4 | |
| 5x 5P_R2 (1uM) | | 4 |
| Total | 25 | 25 |

Ampliseq-2

| Temp | Time | Cycles |
|---|---|---|
| 98°C | 2' | 1 |
| 98°C | 15" | |
| 66 to 58°C | 15" | 2cycle/ea + 56°C |
| 72°C | 20" | 8cycles |
| 72°C | 5' | 1 |

| | 4°C | Hold |

| Purification using AMPURE® | Forward | Reverse |
|---|---|---|
| Nest PCR-5P product | 20 | 20 |
| Beads (1.5x sample volume) | 30 | 30 |
| Total | 50 | 50 |

Mix 10x, 5' at RT, MagSep it, remove sup
2xwash with 150μl 70% ethanol while on the Mag and move beads side to side
Remove 70% ethanol; Dry beads at RT for 5'

| | Forward | Reverse |
|---|---|---|
| Resuspend beads in H2O for 5' at RT | 20 | 20 |

[00228] Step 3: BC-A adaptor ligation and BC-A/P1 enrichment PCR

| | Forward | Reverse |
|---|---|---|
| BC-A adaptor Ligation (in PCR tube) | BC5 | BC6 |
| 10x ligation buffer | 3 | 3 |
| dNTP mix | 0.6 | 0.6 |
| DNA ligase (5u/μl) | 1 | 1 |
| Nick Repair Poly | 2 | 2 |
| $H_2O$ | 18.4 | 18.4 |
| | 25 | 25 |
| P1 PCR-5P product | 4 | 4 |
| BC-A adaptor BC5-8 | 1 | 1 |
| | 30 | 30 |

| | Temp | Time |
|---|---|---|
| | 25°C | 15' |
| Adaptor Lig | 72°C | 5' |
| | 4°C | Hold |

Combine two tube                (F+R)

| BC-A/P1 Equalize PCR (3x reactions) | (F+R) |
|---|---|
| Purified barcode A/P1 product on | AMPbeads |
| PLATINUM® HF Supermix | 100 |
| Equalizer Primers (pink cap) | 10 |
| Total | 110 |
| Mix | |

| | Temp | Time | Cycles |
|---|---|---|---|
| | 98°C | 2 | 1 |
| | 98°C | 15" | 10 |
| Equ-PCR | 64°C | 1' | |
| | 72°C | 1' | 1 |

[00229] Step 4: Enrichment of BC-A/P1 product.

| | 10°C | Hold up to 1h |
|---|---|---|

| | |
|---|---|
| To Equalize PCR beads | 110 |
| Add H₂O | 50 |
| Add Equalizer Capture (purple cap) | 30 |
| Mix 5x and incubate 5' at RT | 190 |

| Wash Equalizer beads (SA) | 1x |
|---|---|
| Transfer mixed SA-bead | 10 |
| wash with Equ Wash Buffer | 50 |
| Resuspend in 6μl Equ Wash Buffer | 10 |
| Mix 6μl SA-bead to Capture-reaction | 190 |
| Total | 200 |

Mix and incubate 5' at RT
MagSep 2', remove sup
2xwash (300μl EquWashBuffer while on the Mag and move beads side to side)
Remove wash buffer completely

| Elute the equalized library with | (F+R) |
|---|---|
| Equalizer Elution Buffer | 25 |

Mix, incubate 5' at 32°C
Mag it and transfer sup to fresh tube
Using 5μl for Qubit HS to determine concentration (ng/μl)

Example 2. Studies on Improved Ion-GUIDEseq (5pBE)

Figure 2A:
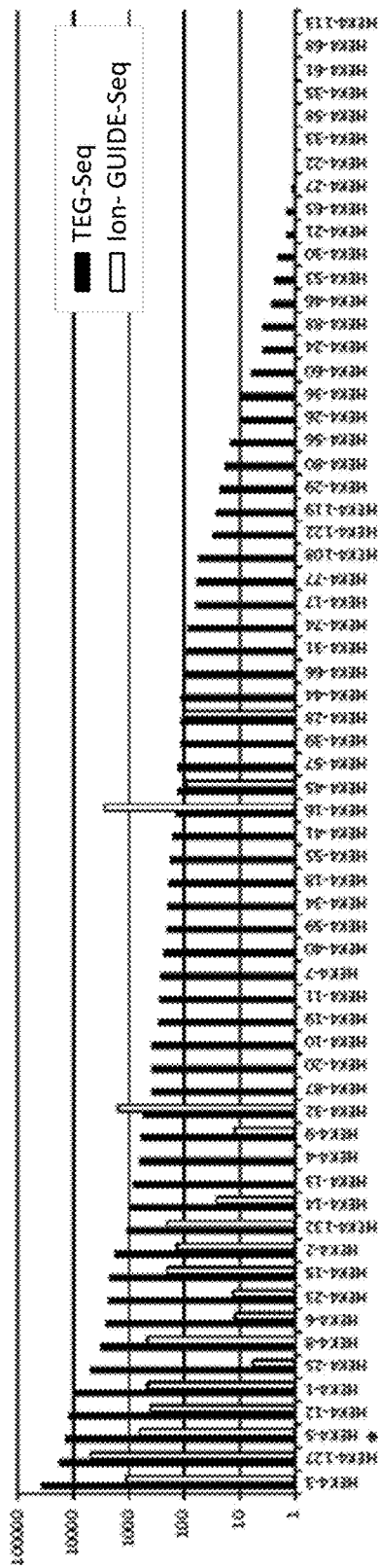
FIGS. 2A-2B.
Figure 2B:
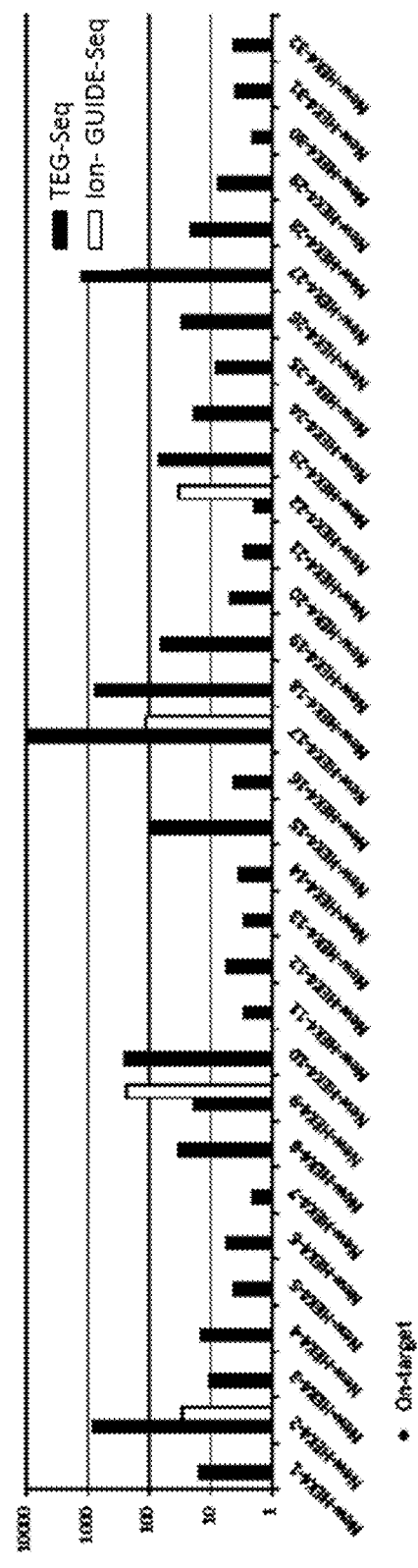

The methodology disclosed in Example 1 (FIG. 1) was tested to detect HEK4 off-targets (published in Tsai, et al., (2015)) transfected with All-in-One plasmid, in a single ION PGM™ (Personal Genome Machine) run. As depicted in FIGS. 2A-2B, the improved Ion-GUIDEseq (i.e., 5pBE) protocol afforded significant increases in specificity associated with Ion-GUIDEseq to a level seen, e.g., with ION AMPLISEQ™ Validation method (a NGS method that is used to validate a single amplified PCR product. Here, in this case, we designed a pair of primers flanking each off-target and PCR amplify the off-target and then sequence it using NGS, count % of indel or dsTag that are caused by double strand break. This method is more sensitive since it only amplifies and sequences a single product (off-target). However, it can only be used for known sequence off-targets and only be used for validation and confirmation). Indeed, a single ION PGM™ run with about 1-3 million reads detected 93% (i.e., 40/43) off-targets at a level of 0.01% or higher, as verified by ION AMPLISEQ™.

Example 3: TEG-Seq: An Improved Workflow for in Cellulo Mapping of CRISPR Specificity Abstract: Engineered nucleases, including the CRISPR/Cas9 system, have been widely used for genome editing in higher eukaryotic cells due to their simplicity and high cleavage activity. However, lack of specificity leading to off-target cleavage is still a concern, especially for their application in gene and cell therapies. To measure this, there have been several methods developed recently (REF), including an in cellulo method, genome-wide unbiased identification of double stranded breaks enabled by sequencing (GUIDE-seq) for genome-wide detection of double strand breaks (REF).

This system represents a major step in the evolution of platforms for unbiased identification of genomic cleavage events. However, this method as originally reported was associated with a significant level of non-specific target amplification which reduced sensitivity and increased the cost to detect low-frequency off-target events.

In an attempt to improve robustness and sensitivity of this tool, we present a modified method we term Target-Enriched GUIDE-seq (TEG-seq). This recent workflow advancement improves the sensitivity approximately 10 fold over Ion-GUIDE-seq and is comparable to the level reached with targeted single-plex PCR based next generation sequencing (Targeted ION AMPLISEQ™). In addition to the increased specificity, we developed a more cost-effective high throughput workflow that enables the study of multiple samples in a parallel. We show application of TEG-seq for the evaluation of various Cas9/gRNA configurations which suggests that delivery of formulated Cas9 protein/gRNA ribonucleoprotein complexes (RNPs) results in significantly fewer off-target events than that from Cas9/gRNA delivered by plasmid. TEG-seq evaluation of two previously reported high-fidelity Cas9 variants (SpCas9HF-1, SpeCas9) in RNP format showed a significant lower on-target activity compared with wild type SpCas9 although their off-target activities were significantly reduced or below the detection limit of this technology. Finally, we used TEG-seq to map on- and off-target cleavage events for the wild type SpCas9 RNP complexed with 22 gRNAs targeting a set of therapeutically relevant mutations and verified as highly specific from in silico CRISPR design tools.

Our result revealed that a majority (78%) of the in silico designed highly ranking gRNAs do not create off-target events detectable using this platform (i.e., fewer than 1 event in 1 million reads). This study demonstrates that using modern in silico design tools to predict specificity; it is possible to achieve highly efficient editing with high specificity using wild type SpCas9 RNPs. The specificity levels seen with this limited set of gRNAs are more than sufficient for cell model development. Deeper sequencing detection analysis will likely be required for testing edited cells for therapeutic applications.

INTRODUCTION

The evolution of genome editing technologies promises the powerful concept of directly correcting mutations or disrupting abnormal genes to cure and prevent diseases, particularly inherited genetic disorders.

Over 50,000 single nucleotide polymorphisms (SNPS) in nearly 3000 genes have been associated to more than 6,000 human diseases and phenotypes (see, e.g., Cox et al., (2015) *Therapeutic Genome Editing: Prospects and Challenges. Nat Med.* 21:121-131; www.omim.org/statistics/geneMap; www.disgenet.org/web/DisGeNET/menu; jsessionid=4aqu6smfdc4c13gfeo11snax1). These SNP/mutations are potentially correctable or disruptable using genome editing tools, such as CRISPR-Cas9 (see, e.g., Mali, P. et al., (2013) *RNA-guided human genome engineering via Cas9. Science* 339:823-826; Cong, et al., (2013) *Multiplex genome engineering using CRISPR/Cas systems. Science* 339:819-823; Kim, et al., (2014) *Highly efficient RNA-guided genome editing in human cells via delivery of purified Cas9 ribonucleoproteins. Genome Res* 24:1012-1019; Schumann, et al., (2015) *Generation of knock-in primary human T cells using Cas9 ribonucleoproteins. Proc Natl Acad Sci USA* 112:10437-10442), TALEN (see, e.g., Kim, et al. (2013a) *A library of TAL effector nucleases spanning the human genome. Nat. Biotechnol.* 31:251-258; Kim, et al., (2013c) *TALEN-based knockout library for human microRNAs. Nat. Struct. Mol. Biol.* 20:1458-1464; Miller, et al. (2011) *A TALE nuclease architecture for efficient genome editing. Nat. Biotechnol.* 29:143-148; Mussolino, et al., (2011) *A novel TALE nuclease scaffold enables high genome editing activity in combination with low toxicity. Nucleic Acids Res* 39: 9283-9293) and ZFN (see, e.g., Bibikova, et al., (2003) *Enhancing gene targeting with designed zinc finger nucleases. Science* 300:764; Kim, et al., (2009) *Targeted genome editing in human cells with zinc finger nucleases constructed via modular assembly. Genome Res.* 19:1279-1288; Kim, et al., (2010) *Genome editing with modularly assembled zinc-finger nucleases. Nat. Methods* 7:91; 91-92).

One recent successful example is the correction of a SNP in the CYBB gene in mouse hematopoietic stem cells using CRISPR/Cas9 (Ravin, et al., (2017) *CRISPR-Cas9 gene repair of hematopoietic stem cells from patients with X-linked chronic granulomatous disease. Science Translational Medicine.* 9:2-10) which cured the X-linked chronic granulomatous disease (X-CGD). Another example of this approach are the clinical trials using various therapeutic engineered nucleases to disrupt CCR5, a co-receptor for HIV, by a zinc finger nuclease (ZFN) (see, e.g., DiGiusto, et al., (2016) *Preclinical development and qualification of ZFN-mediated CCR5 disruption in human hematopoietic stem/progenitor cells. Molecular Therapy—Methods & Clinical Development.* 3:1-12; Perez, et al., (2008) *Establishment of HIV-1 resistance in CD4+ T cells by genome* editing using zinc-finger nucleases. *Nat. Biotechnol.* 26:808-816; Holt, et al. (2010) *Human hematopoietic stem/progenitor cells modified by zinc-finger nucleases targeted to CCR5 control HIV-1 in vivo. Nat. Biotechnol.* 28:839-847; Tebas, et al., (2014) *Gene editing of CCR5 in autologous CD4 T cells of persons infected with HIV. N. Engl. J. Med.* 370: 901-910; Li, et al., (2013) *Genomic editing of the HIV-1 coreceptor CCR5 in adult hematopoietic stem and progenitor cells using zinc finger nucleases. Mol. Ther.* 21:1259-1269), TALEN (see, e.g., Mussolino, et al., (2011) *A novel TALE nuclease scaffold enables high genome editing activity in combination with low toxicity. Nucleic Acids Res.* 39:9283-9293; Ye, et al., (2014) *Seamless modification of wild-type induced pluripotent stem cells to the natural CCR5Delta32 mutation confers resistance to HIV infection. Proc. Natl. Acad. Sci. USA* 111:9591-9596) and CRISPR/Cas9 (Ye, et al., (2014); Mandal, et al., (2014) *Efficient ablation of genes in human hematopoietic stem and effector cells using CRISPR/Cas9. Cell Stem Cell* 15:643-652). However, these nucleases are known to induce off-target mutations at sites with homology to the target sites. Gene and cell therapeutic applications of these nucleases require a comprehensive knowledge of their off-target effects to minimize the risk of deleterious outcomes.

Many strategies have been explored to improve the specificity of targeted nucleases. Modifications to the FokI dimerization domain increased the specificity of ZFNs and TALENs by requiring two obligate heterodimers to bind the target DNA in a specific orientation and spacing (Miller, et al., (2007) *An improved zinc-finger nuclease architecture for highly specific genome editing. Nat. Biotechnol.* 25:778-785; Guo, et al., (2010) *Directed evolution of an enhanced and highly efficient FokI cleavage domain for zinc finger nucleases. J. Mol. Biol.* 400:96-107). Also, the inactivation of Cas9 nuclease domains to create Cas9 nickases or Cas9-FokI fusions has increased specificity by requiring two gRNA/Cas9 complexes, each cleaving a single strand of DNA to generate a double strand break (DSB) in a precise distance and orientation (Ran, et al., (2013) *Double nicking by RNA-guided CRISPR Cas9 for enhanced genome editing specificity. Cell* 154:1380-1389; Mali, et al., (2013) *CAS9 transcriptional activators for target specificity screening and paired nickases for cooperative genome engineering. Nat. Biotechnol.* 31:833-838; Tsai, et al., (2014) *Dimeric CRISPR RNA-guided FokI nucleases for highly specific genome editing. Nat. Biotechnol.* 32:569-576; Guilinger, et al., (2014) *Fusion of catalytically inactive Cas9 to FokI nuclease improves the specificity of genome modification. Nat. Biotechnol.* 32:577-582).

Reducing the length of complementarity between the gRNA and the target site from 20 to 17 nucleotides was shown to increase the specificity of DNA cleavage by Cas9 (Fu, et al., (2014) *Improving CRISPR-Cas nuclease specificity using truncated guide RNAs. Nat. Biotechnol.* 32:279-284). Recently, structure-guided protein engineering has been used to develop novel Cas9 variants that showed low or no off-target cleavage (Slaymaker, et al., (2016) *Rationally engineered Cas9 nucleases with improved specificity. Science* 351:84-88; Kleinstiver, et al., (2016) *High-fidelity CRISPR-Cas9 nucleases with no detectable genome-wide off-target effects. Nature* 529(7587):490-495). These improvements have significantly mitigated initial concerns over the specificity of CRISPR/Cas nucleases. However, regardless of the nuclease technology, it is difficult to determine the full spectrum of off-target cleavage in a complex genome under various experimental conditions.

An efficient, unbiased and reliable genome-wide off-target detection method is crucial for the application of genome editing-based gene and cell therapy as well as for benchmarking the fidelity evaluation of different gene editing tools.

Various methods have been developed to identify nuclease-cleaved off-target sites. These methods rely on the double strand breaks (DSBs) caused by nucleases that can be marked by a DNA tag either through in vitro ligation or in cellulo integration. The marked DSBsite is then amplified and sequenced using next generation sequencing (NGS). Several in vitro methods including BLESS-seq (Crosetto, et al., (2013) *Nucleotide-resolution DNA double-strand break mapping by next-generation sequencing. Nature Methods* 10:361-368), HTGTS (Frock, et al. (2016) *Genome-wide detection of DNA double-stranded breaks induced by engineered nucleases. Nat. Biotechnol.* 33:179-187), CIRCLE-Seq (Tsai et al., (2017) *CIRCLE-seq: a highly sensitive in vitro screen for genome-wide CRISPR-Cas9 nuclease off-targets. Nature Method* 14:607-614) have been developed for off-target detection. These methods, by nature of the fact that the genomic DNA substrate has been removed from a cellular context and stripped of all protein, tend to identify all possible on- and off-target cleavage sites for a particular gRNA. The data analysis can also be challenging due to the potentially high non-specific noise caused by PCR amplification used to enrich the marked DSB. Digenome-Seq (Kim, et al., (2015) *Digenome-seq: genome-wide profiling of CRISPR-Cas9 off-target effects in human cells. Nat Method.* 12:237-243), another in vitro method which relies on whole genome sequencing, may reduce the noise and false positive calls, but sacrifices the sensitivity necessary to faithfully identify off-target sites that are cleaved at low frequencies. In cellulo approaches more closely simulate the cellular nuclease-based gene editing environment in which off-target cleavage events occur and are tagged in living cells. Two methods, IDLV-seq (Gabriel, et al., (2011) *An unbiased genome-wide analysis of zinc-finger nuclease specificity. Nat. Biotech.* 29:816:824; Wang, et al., (2015) *Unbiased detection of off-target cleavage by CRISPR-Cas9 and TALENs using integrase-defective lentiviral vectors. Nat Biotechnol* 33:175-179) and GUIDE-seq (Tsai, et al., (2015)) were developed with this goal. IDLV-seq relies on the integration of a viral DNA to DSBsite. However, the viral DNA is not chemically protected which could lead to partial degradation and low efficiency of the tag integration to DSB and low sensitivity of the detection. GUIDE-seq uses phosphorothioate-modified double strand DNA oligos (dsOND) as tags that prevents degradation and improves tag integration efficiency to DSBs in living cells. However, GUIDE-seq also requires an exponential PCR amplification step to enrich the marked DSBsites that may cause higher non-specific noise and potential false positive calls.

We addressed these drawbacks of the original GUIDE-seq method and developed Target-Enriched Guide-seq (TEG-seq), in which 5' phosphose primers were used for PCR amplification that differentially marked the amplicon containing DSBsite from non-specifically amplified products and results in preferential magnetic bead enrichment of marked DSB amplicons. This series of improvements significantly reduced non-specific amplification and improved sensitivity of DSB detection. We also developed a 96-well format workflow that enables us to study multiple samples in a parallel and more cost-effectively. The sensitivity of this unbiased TEG-seq method reached the level of Targeted ION AMPLISEQ™ that has been widely used to validate the known and predicted gRNA off-target sites through direct amplification and next generation sequencing. In this study, we applied TEG-seq to various applications including: 1) Profiling of genome-wide off-targets using different formats of CRISPR-Cas9 for transfection, for example Cas9-gRNA in plasmid DNA vs Cas9 protein/gRNA ribonucleoprotein complexes (Cas9 RNPs); 2) Validation of high-fidelity Cas9 variant RNP complexes and 3) Genome-wide off-target study on highly scoring CRISPR gRNAs designed by in silico CRISPR design tools to simulate the scenario of HDR-based SNP/gene correction.

Results:

Ion-GUIDE-Seq and TEG-Seq Workflow

Using a similar double strand DNA Tag (dsTag) reported by Tsai's et al. (Tsai, et al., (2015)), we tested the GUIDE-seq method using Ion Torrent NGS (Ion-GUIDE-seq). We found that only a very small portion of the PCR products contain the desired dsTag sequence and the majority of PCR products amplified using dsTag specific primer (F1 or R1) paired with adaptor primer (P1) were actually P1/P1 product. This was confirmed by using the P1 primer only under different conditions for multiple samples. Our initial NGS results from multiple sequencing runs also showed that a significant number the most frequent read-count hits were not related to CRISPR/Cas9 editing. This, in turn, likely impairs the sensitivity of Ion-GUIDE-seq for genome-wide off-target detection.

To reduce the undesired P1/P1 product amplified in Ion-GUIDE-seq and enrich the targeted DSB amplicons for NGS, we developed TEG-seq sample preparation procedure and data analysis plug-in tool. As shown in the diagram (FIG. 1), we used 5' phosphorylated primers paired with the P1 product for the second round PCR amplification. This resulted in a 5' phosphate overhang on the products (5P-F2/P1 and 5P-R2/P1) but not on the P1/P1 product. In the next step (M3), a non-phosphorylated barcoded adaptor (BC-A, containing the Ion sequencing primer A) was specifically ligated to the phosphorylated product but not the P1/P1 product (which lacks a 5' phosphate required to ligate the non-phosphorylated barcode adaptor). A third round of PCR was then performed using P1 and "A-tail" primers to further enrich the P1-A product (step M4). The BC-A-tail primer contains an internal spacer that stops the polymerase-mediated nucleotide extension and leaves a single strand tail at the end of the PCR product. Finally, the dsTag-specific A-P1 product was enriched using a biotinylated oligo complimentary to the tail sequence and captured by streptavidin (SA) magnetic bead selection (step M5). The barcoded A-P1 product was then sequenced.

To compare the off-target detection levels between the two methods, we performed Ion-GUIDE-seq and TEG-seq using a gRNA target HEK4 (previously identified to have the highest number of off-target sites in Tsai, et al., (2015)). As shown in FIG. 2, the number of targets detected by TEG-seq was 96, which is four fold more than the Ion-GUIDE-seq at 22 targets. For the same 22 positive targets, the average of RPM (reads per million) was about 10 fold higher with TEG-seq than that of Ion-GUIDE-seq (Table 8). The off-target profile of the HEK4 gRNA generated by TEG-seq is significantly different from Tsai's published data (Tsai, et al., (2015)), especially for the low read-listed off-targets. Of 95 off-targets, 32 were new (FIG. 2B, Table 8) that were not identified by GUIDE-seq, data described here and in Tsai's published data (Tsai, et al., (2015)).

Comparison of Sensitivity of TEG-Seq to Targeted Ion AmpliSeq™

Figure 3A:
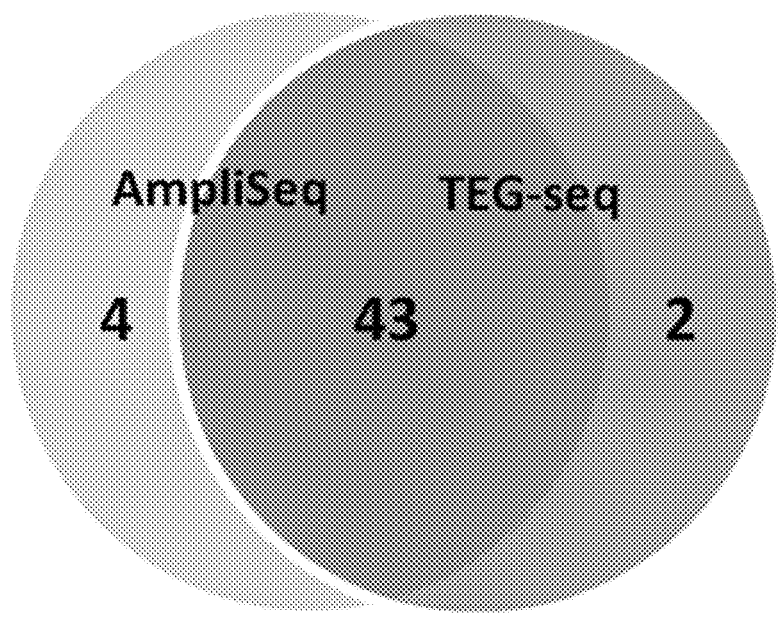
FIGS. 3A-3B shows comparisons of off-target detection level between Targeted ION AMPLISEQ™, TEG-seq and Ion-Guide-seq. Data related to this is set out in Table 8.
Figure 3B:
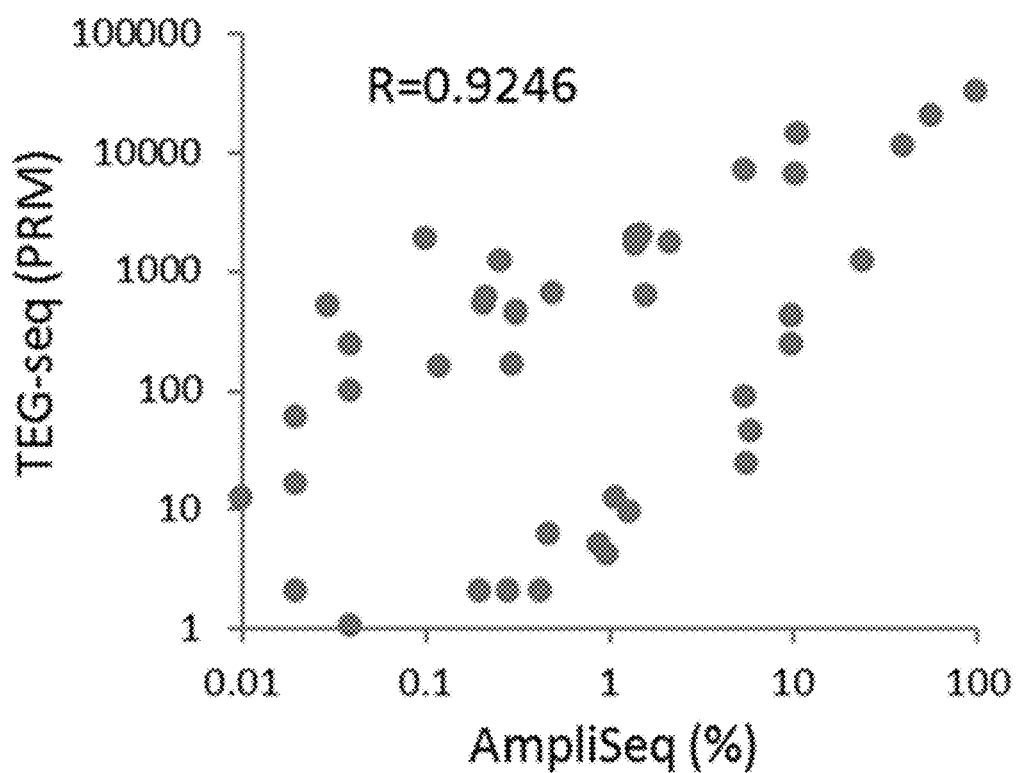

To evaluate the sensitivity of TEG-seq, we compared it with Targeted Ion AmpliSeq™, which is currently the most sensitive way to detect nuclease-induced editing at predicted target and non-target sites. We chose four gRNA sites (HEK1, VEG1, VEG3 and HEK4 (Tsai, et al., (2015)) with a range of in silico design scores (Table 6) for our study. Sixty on- and off-target sequences (Table 9) that had top-read counts using GUIDE-seq (Tsai, et al., (2015)) were chosen and gRNA template sequences were cloned into a plasmid that expressed both gRNA and Cas9 in the same construct. Of the 30 targets of HEK4, 27 were detected by Targeted Ion AmpliSeq™ (Table 9). The percentage of Targeted Ion AmpliSeq™ cleavage efficiency was calculated by dividing the number of reads containing any indel or dsTag by the total number of mapped reads at that loci. Using this calculation, we found that the on-target cleavage percentage (HEK4-5*) was 40%. In agreement with Tsai et al., we found the most highly edited site was the off-target locus, HEK4-3 which contained indels measured at 99%. Approximately 50% (15 of 27) of the loci tested for off-target cleavage events demonstrated indels or dsTAG integration with frequencies less than 1%. The rarest event detected by Targeted Ion AmpliSeq™ was 0.01% (HEK4-29). For the same 30 HEK4 targets, TEG-seq detected 29 while Ion-GUIDE-seq detected 17. The RPMs were generally higher in the targets of identified by TEG-seq compared to those of Ion-GUIDE-seq. Two off-target loci (HEK4-17 and HEK4-24) were detected by TEG-seq, but not by Targeted Ion AmpliSeq™. For the 30 targets predicted from the VEG1, VEG3 and HEK1 gRNAs, 20 were detected by Targeted Ion AmpliSeq™ (Table 8), 16 by TEG-seq and 11 by Ion-GUIDE-seq. Four (VEG1-8, VEG3-9, VEG3-12 and VEG3-14) were detected by Ion AmpliSeq™, but not by TEG-seq (Table 8). Overall, from 60 targets chosen from previous published data, 49 were detected in our study either by Ion AmpliSeq™ or TEG-seq. Of the 49 positive targets, Ion AmpliSeq™ detected 47 (95.9%) and TEG-seq detected 45 (91.3%). 43 were detected by both TEG-seq and Targeted Ion AmpliSeq™ (FIG. 3A). Four were detected by Ion AmpliSeq™, but not by TEG-seq, vice versa; 2 were detected by TEG-seq, but not by Ion AmpliSeq™. The similar percentage of detected targets by TEG-seq (91.3%) and Targeted Ion AmpliSeq™ (95.9%) indicated their detection sensitivity is similar under current NGS throughput, i.e., 1 to 5 million reads per target site for TEG-seq and 30,000 to 150,000 reads per target site for Targeted Ion AmpliSeq™. There is a high correlation (R=0.9246) between the RPM from TEG-seq and the percentage cleavage from Targeted Ion AmpliSeq™ (FIG. 3B).

Comparison of Genome-Wide Off-Target Cleavage Using Different CRISPR/Cas9 Formats In comparison with Cas9 delivered to the cell via plasmid DNA, direct transfection of Cas9 protein complexed with purified gRNA provides a transient burst of activity with no opportunity for direct integration and persistent cleavage activity (Liang et al. (2015) *Rapid and highly efficient mammalian cell engineering via Cas9 protein transfection. J. Biotech.* 208:44-53). The Cas9/gRNA ribonucleoprotein (RNP) is quickly turned over by the cell which likely lowers the cellular concentration and thus the opportunity for off-target cleavage at unintended and possibly lower affinity sites in the genome on the chromosome.

CRISPR RNP delivery has grown in popularity but validation of genome-wide off-target effects among wild type and various 'high fidelity' Cas9 as RNPs has not been carefully validated. This type of specificity evaluation benchmarking of various RNPs will be important particularly for therapeutic applications, where the DNA plasmid format is not optimal.

Figure 5:
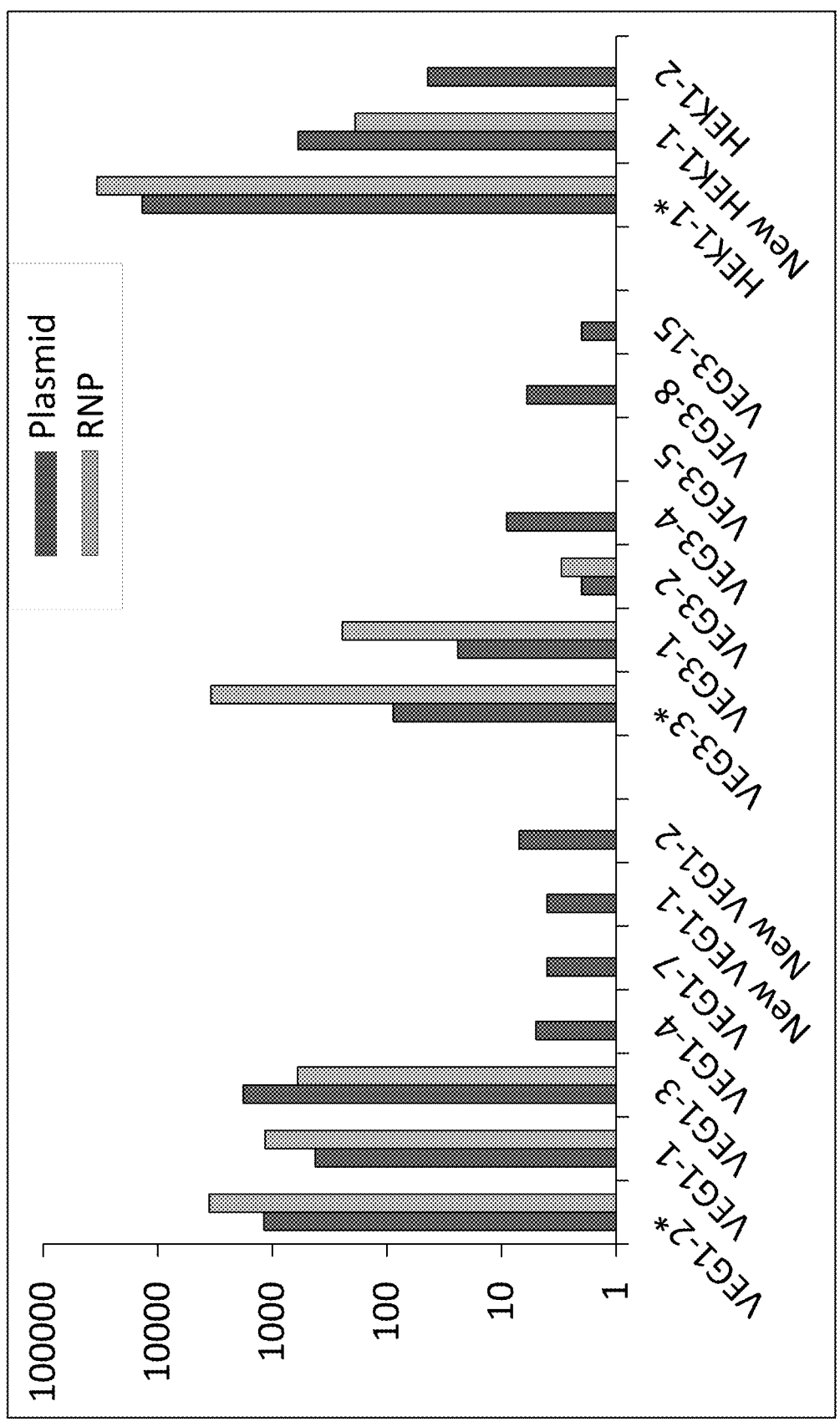
FIG. 5 shows a comparison of on- and off-target activity detected by TEG-seq on HEK1, VEG1 and VEG3 transfected with RNP of eSpCas9-1.1, SpCas9-HF1 and wide-type SpCas9. Data used to generate this figure is set out in Table 11.

In an effort to more clearly define the differences in specificity between Cas9 plasmid and RNP delivery, we applied TEG-seq to the more promiscuous HEK4 gRNA and found that RNP delivery yielded approximately 9 fold fewer detectable off-target events (11 vs. 95) as compared with Cas9 plasmid delivery (see, e.g., FIG. 5 and Table 11). In general, we found significantly lower off-target reads with the RNP format than that of plasmid format. More importantly, the ratio of on-target to the next highest off-target site using RNP is considerably higher than with the plasmid format. In agreement with Tsai et al., when using the plasmid format, two off-target events (HEK4-3 and HEK4-127) are actually more frequent than that of on target (HEK4-5*). This phenomenon was not seen with RNP. As indicated in FIG. 5, results using gRNAs with higher specificity scores (VEG1, VEG3 and HEK1) showed marked improvement with RNP delivery but a subset of significantly active off-target sites remain.

These results suggest that using wild type Cas9 as RNP reduces the number of detectable off-target events and improves overall specificity over plasmid DNA delivery as measured by the ratio of on-target to next highest detectable off target event. This is important when considering cell line development where a log difference in on- to next highest off-target event represents an approximate 1 in 10 chance of isolating a cell line with both events occurring in the same genome. Conversely, for therapeutic applications of Cas9 RNPs in non-dividing primary cells, complete elimination of off-target events would be desirable as clonal isolation is generally not achievable prior to application of cells to the patient.

Validation for High Fidelity Cas9 Variants in RNP Format

The ideal genome editing tool for both cell line development and therapy will have high on target activity with absolute specificity. To facilitate development of such a tool, GUIDE-seq has been used for searching and validating mutants of Cas9 for potential high-fidelity Cas9 with high on-target activity and low or no off-target activity (Kleinstiver, et al., (2016)). Based on the complex crystal structure of SpCas9, gRNA and target DNA (Nishimasu, et al. (2014) Crystal structure of Cas9 in complex with guide RNA and target DNA. Cell 156:935-949; Anders, et al. (2014) Structural basis of PAM dependent target DNA recognition by the Cas9 endonuclease. Nature 513:569-573), two potential high-fidelity SpCas9 were identified that showed no off-target at the genome-wide scale with comparable on-target cleavage activity to the wild-type Cas9. One, SpCas9 HF-1, was engineered through quadruple amino acid substitutions to abolish hydrogen bonds between Cas9 and the targeted DNA (Kleinstiver, et al., (2016)). Another, eSpCas9, was engineered through triple amino acid substitutions to reduce the positively-charged residues within nt-groove, weakening the binding of non-target DNA to Cas9 RNP (Slaymaker, et al., (2016).

In all these cases, the targeted mutations effectively lower the affinity of the RNP for its substrate (DNA) in turn reducing the binding and cleavage of lower affinity off-target sites. In the reports cited above, the mutant Cas9s were delivered to cells via plasmid DNA, likely leading to very high levels of expression and local concentration of the RNP in the nucleus. This likely led to effectively overcoming a reduction in affinity the RNP has for its target while reducing or eliminating binding of lower affinity off-target sites.

As mentioned above, direct delivery of RNP to cells is desirable for various reasons other than purely specificity, so we set out to evaluate the efficacy and specificity of these mutants in under these conditions.

We expressed and purified eSpCas9 1.1 and SpCas9-HF1 proteins and validated their genome-wide off-target loci with four guide RNAs (HEK1, HEK4, VEG1 and VEG3) using TEG-seq. Although no off-target loci were detected for SpCas9-HF1 from the four gRNAs tested, the on-target activity was approximately 10 to 100 fold lower than the wild type SpCas9 (FIGS. 5A and 5B). eSpCas9 also yielded equivalent or lower on target activity and several off-target loci were detected. Interestingly, several off target loci (two from HEK4 and one from VEG3) had not been detected previously from plasmid or RNP (FIGS. 5A and 5B). The dramatic drop of on-target activity for the two high fidelity Cas9 proteins were confirmed by using T7 endonuclease-based genome cleavage detection (GCD) assay on additional 23 guide sites (FIG. 5C), in which the relative % activity was normalized to wild type of Cas9. The SpCas9-HF1 lost at least 50% activity in 21 out of 23 sites tested. Majority of them are totally lost activity. The eSpCas9 lost at least 50% activity in 15 out of 23 sites tested (FIG. 5C). We noticed six target sites (EMX1-1, EMX1-2, EMX-3, VEGFA-2, VEGFA-3 and VEGFA5) were also validated for eSpCas9 in the previous published data using the plasmid format (Kleinstiver, et al., (2016)). In comparison, 5 out 6 targets (except VEGFA5, which is corresponding VEGFA1 in Kleinstiver's paper) lost on-target activity for at least 50% in our study while they were all maintained a comparable activity level to the wtCas9.

Off-Target Detection Level Under Different Sequencing Depth

The sensitivity of TEG-seq and GUIDE-seq detection is directly proportional to the sequencing depth. The data from our lab and other groups (Kleinstiver, et al., (2016), Tsai, et al., (2015)) were generated using either ION PGM™ or ILLUMINA® MISEQ® which yield approximately 1-5 million reads per run. To enable a fair comparison between different runs, experiments, and platforms, we normalized data by 'total mapped reads' using Reads Per Million (RPM). We detected a significant number of relatively low frequency off-target events at the level of 1-10 RPM which corresponded to approximately 0.01% to 0.1% by ION AMPLISEQ™ using the ION PGM™ (FIG. 3). The detection level using current sequencing platforms (e.g., ION PGM™ and MISEQ®) is approximately 1 RPM. Since it is likely that off target verify this, we used the ION PROTON™ and re-sequenced two samples, HEK4 with a low (24) and HEK1 with a high (76) in silico design score (Table 6), that were delivered with wild type SpCas9 RNP. The ION PROTON™ generated 53 million reads for HEK4 and 34 million reads for HEK1, which is approximately 17 fold more than the number of reads (3 million for HEK4 and 2 million for HEK1) from the ION PGM™. With this increase depth, we did not detect any additional off-target events for the HEK1 gRNA (Table 8), but did detect 15 additional off-targets from the HEK4 gRNA with the read counts all less than 0.2 RPM from ION PROTON™. All of the 15 additional off-targets detected by ION PROTON™ using the RNP format were detected by the ION PGM™ in the when the plasmid format was used (FIGS. 2 and 5). When we normalized reads by total mapped reads, the RPM profile between ION PGM™ and ION PROTON™ is very similar with the exception of the additional 15 off-targets detected by ION PROTON™ (FIG. 5).

Genome Wide Off-Targets on in Silico Designed "High Score" gRNAs for Therapeutic Application Significant effort has been made to create a rule set to enable better in silico prediction of CRISPR specificity. However, there remains a relatively large discrepancy between off-target events detected by directed approaches (GUIDEseq, ION AMPLISEQ™, and others) with those predicted using the current in silico design tools (Tsai, et al., (2015)). Still, since the design space (PAM availability) is so vast across genomes, an in silico filter is a critical tool to narrow the number of gRNAs to empirically test. In general, each of the currently available tools integrate gRNA binding sites using a scoring system that compares other sites across the genome and ranks them with respect to various penalty scores according to criteria such as the homology, total number of mismatches, the position of a particular mismatch with respect to the PAM, the PAM sequence itself, and the appearance of specific nucleotides and homopolymers. These rules are applied and each gRNA receives a ranking score, the higher the score, the fewer the potential off-targets. Given the recent evolution of directed off-target monitoring platforms, it's only been recently that data comparing in silico ranking and non-biased detection of actual off target events has emerged (Tsai, et al., (2015) and Wang, et al., (2015)). We felt it pertinent to apply TEG-seq in what we feel is the optimal configuration of CRISPR for editing in mammalian cells which is wild type spCas9 RNPs formed with highly ranking gRNAs. We chose wild type Cas9 due to its high activity as an RNP across multiple target sites. Most of the gRNAs evaluated above and in previous work were likely chosen as a model due to their propensity for off target cleavage. These gRNAs scored relatively poorly in the available screening tools, especially HEK4 and VEG3 with 24 and 27 respectively from MIT CRISPR Design used in this study (Table 9).

Figure 4:
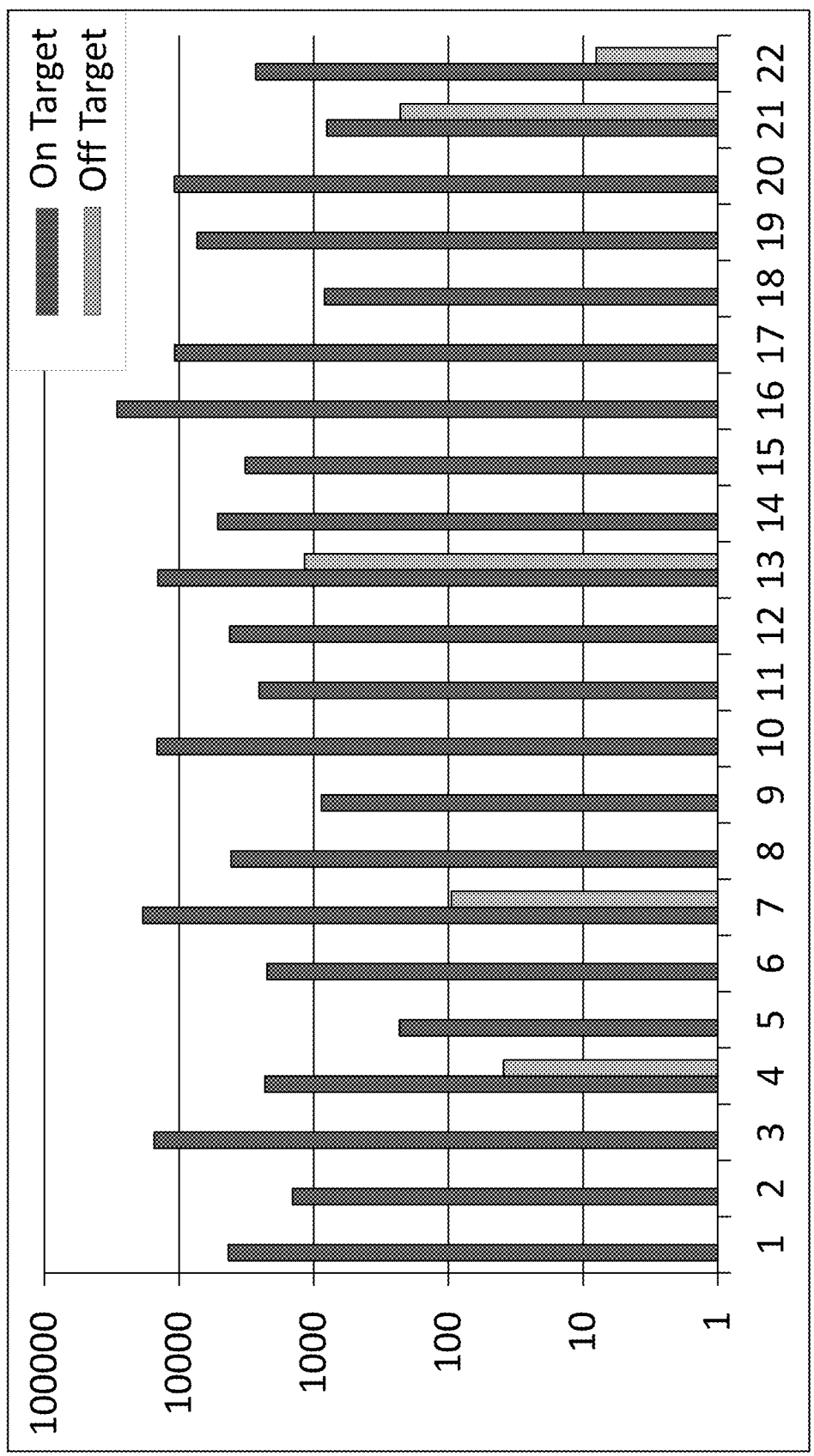
FIG. 4: On- and off-targets detected from high score ('good') gRNA targets by TEG-seq and confirmed by Targeted ION AMPLISEQ™: 22 good (high score) gRNA sites targeting disease-associated SNPs designed through CRISPR design tool. Their on- and off-targets were detected by TEG-seq and measured by PRM. Off-targets were also confirmed by Targeted ION AMPLISEQ™.

For this phase, we chose 22 SNPs from eight common genetic disorders (Table 2), with the intent to repair these SNPs via HDR with short single or double stranded donor templates (Ochiai, (2015) *Single-Base Pair Genome Editing in Human Cells by Using Site-Specific Endonucleases. Int. J. Mol. Sci.* 16:21128-21137; Singh, et al., (2015) *A Mouse Geneticist's Practical Guide to CRISPR Applications. Genetics,* 199:1-15; Yoshimi, et al., (2014) *Allele-specific genome editing and correction of disease-associated phenotypes in rats using the CRISPR-Cas platform. Nature Communications.* 5:4240). We chose a 50 base window (25 bases each side, Table 2) around each mutation site due to the reduction of HDR efficiency seen as the cleavage site moves away from the intended edit (Liang, et al., (2017) *Enhanced CRISPR/Cas9-mediated precise genome editing by improved design and delivery of gRNA, Cas9 nuclease, and donor DNA. Journal of Biotechnology* 241:136-146; Richardson, et al., (2016) *Enhancing homology-directed genome editing by catalytically active and inactive CRISPR-Cas9 using asymmetric donor DNA. Nat. Biotechnol.* 34:339-344). We used the MIT CRISPR design tool to choose gRNA (underlined) with PAM (Green colored Italic) and chose the gRNA with the highest score that cleaves DNA within 10 base distance to the SNP loci to facilitate efficient HDR-based SNP correction (Table 2). We then transfected HEK293FT cells with gRNA and wt Cas9 protein and performed TEG-seq analysis. We were able to detect all 22 on-target cleavage events (data not shown) with RPMs ranging from the low hundreds to tens of thousands. Of the 22 detected on-target 'SNP' gRNAs, five resulted in detectable off-target cleavage events by TEG-seq and were subsequently confirmed by Targeted ION AMPLISEQ™ (FIG. 4 and Table 12). Of the five gRNAs that had a single off-target event, those tended to be detected at 1 to 3 logs lower frequency. The exception was #21 which appeared less than 1 log less frequently than the on-target event. This was reflected by the percentage of indel detected by Targeted ION AMPLISEQ™, in which all were below 0.29% except gRNA #21 which had a high indel percentage (30%). The in silico design score from MIT design tool for gRNA #4 was 49, the lowest score of all the gRNAs tested in this experiment. The scores for the other four sites (#7, #13, #21 and #22) where off target indels were detected were not in the lower range compared to other sites with no off-target, suggesting the tools used in this study lacks the high predictability for some targets. We then checked MIT predicted off-target list for the five sites. Only two (#13 and #22) were in the predicted list (Table 3). Off target events with the rest (#4, #7 and #21) were not predicted by the design tool. Interestingly, the three unpredicted off-target loci contain a "bulge" mismatch base to the gRNA, suggesting the design tool used in this study lacks the predictability for the off-targets with "bulge" mismatch.

DISCUSSION

The recent rapid evolution of genome editing tools has brought the efficiency of chromosomal cleavage, and thus gene knock out and editing, to a point where cell model generation and gene correction therapy applications have become more tenable concepts. Now that the genome can be addressed and cut effectively, the specificity of that cut becomes a much more significant issue. GUIDE-seq (Tsai, et al., (2015)) and other genome-wide off-target detection methods (Crosetto, et al., (2013), Frock, et al. (2016), Wang, et al., (2015)) have been developed to provide unbiased mapping of on- and off-target cleavage events. These technologies depend on the exponential amplification of tagged segments of the genome followed by sequencing and identification of those amplicons.

In what we feel is a good method of in cellulo detection of these events, GUIDE-seq has proven a valuable improvement of technologies to tag and identify genomic breaks. While this technology has proven to be an advancement to the field, it is beset with high background reads and a technically challenging workflow. With the modification of PCR by using 5' phosphate primers followed by beads enrichment for targeted fragments, TEG-seq significantly reduced background and therefore increased its sensitivity. We set out to streamline this workflow in 96× format and create a more robust readout in an effort to democratize this technology. We also noticed many top-counted hits do not contain PAM sequence. They could be contributed by nature DSB (breakpoint hotspots and DNA translocation) and other large scale DNA structural alterations. It was described in the previous study (Tsai, et al., (2015)) and was not our focus in this study.

The profile of off-target detected by TEG-seq and GUIDE-seq (Tsai, et al., (2015)) was similar for those high-read count hits, however, it was quite different for the low-count off-targets that represent the rare-cleaved sites. This difference could be due to many factors including the cell type, reagents and other conditions. The sequencing depth may also contribute to the difference between the results of the two studies. The total mapped reads in this study is 1 to 5 million from the ION PGM™ for each sample. Deeper sequencing using the ION PROTON™ (17-fold) detected more off-targets, but their RPM values were all <0.2, which was one per 5 million reads. The ION PROTON™ did not detect any additional off-targets with RPM is >1 when compared to the lower depth ION PGM™ sequencing. This data indicated that with the throughput of 1-5 million reads generated by the ION PGM™ or $I_{LLUMINA}$®'s MISEQ®, off-target loci could be detected at the level of 1 RPM. Depending on the biological off-target tolerance for cell model development or gene therapy and the cost consideration of sequencing, different platforms of NGS could be chosen for TEG-seq. Theoretically, it is possible to avoid or minimize some rare-cleaved off-targets by using less starting cell number for editing. For example, those off-targets with RPM <0.2 could be potentially eliminated if using less than one million cells in this study. The requirement of the cell number for gene editing could be much less than million if using dividing cells like iPSC since it can be expanded after editing. However, it may require more than millions of cells if using the non-dividing cell such as primary T-cell that could potentially create more off-targets.

To date, there is no comprehensive comparison data regarding the sensitivity of different off-target methods on the same targets. The Targeted ION AMPLISEQ™ method using a single-plex PCR to amplify the target region followed by deep sequencing is currently the most sensitive way and has been widely used to evaluate sequence-known or predicted off-targets. To evaluate the sensitivity of TEG-seq, we compared it to the Targeted ION AMPLISEQ™ on the same set of off-targets from the previous published study (Tsai, et al., (2015)). The detection level of TEG-seq was shown to be close to the level of Targeted ION AMPLISEQ™. To reach a similar level of detection, more reads (1-5 million) from TEG-seq are required than that (30,000-100,000) from Targeted ION AMPLISEQ™ since TEG-seq is multi-plex PCR while Targeted ION AMPLISEQ™ is a single-plex PCR. There are still a few, especially the rare cleaved off-targets were not detected by either TEG-seq or Targeted ION AMPLISEQ™. This could be due to the low sequencing depth. The detection level for both methods could be higher by increase their sequencing depth.

There is a limitation for TEG-seq and GUIDE-seq for genome-wide off-target screening. It requires the integration of a dsTag into the targeting cell, which may not be feasible for editing the primary or embryonic stem cells, for which the cell numbers are limited or be toxic to the dsTag. A combination application of TEG-seq and Targeted ION AMPLISEQ™ may be a valuable option to compromise this limitation before a non-tag in cellulo analysis method is available. The TEG-seq and Targeted ION AMPLISEQ™ combination application includes: 1) perform pre-screen using TEG-seq on the similar cell to the targeting cell, that has no limitation for the cell numbers to identify off-target candidates; 2) then use Targeted ION AMPLISEQ™ to validate the candidates from TEG-seq on the edited targeting cell.

Unlike other specific nucleases (ZFNs, TALEN and Meganucleases) that rely on protein-DNA recognition, CRISPR/Cas9 relies on RNA-DNA recognition. It has quickly become the preferred system for genome engineering due to its high editing efficiency and simplicity, as it requires only Cas9 and a guide RNA. That is why CRISPR/Cas9 therapeutics have been pushed into many human testing (Cormac Sheridan, (2017) *CRISPR therapeutics push into human testing. Nat Biotech.* 35:3-5). Although studies have indicated CRISPR generated high off-targets (Tsai, et al., (2015) most of those reported studies have used DNA plasmid to express Cas9 and gRNA, which is not ideal for gene and cell therapies due to low efficiency of transfection of primary cells, DNA-related cytotoxicity, the presence of bacterial DNA sequences in plasmid backbones, and the possibility of random integration of plasmid fragments into the genome. Using purified Cas9 protein (Kim, et al., (2014), Schumann, et al., (2015)) and in vitro transcribed gRNA (Hendel, et al., (2015) *Chemically modified guide RNAs enhance CRISPR-Cas genome editing in human primary cells. Nat Biotechnol* 33:985-989) indicated high specificity in the human knock-in editing primary cells. Our results demonstrated that the Cas9 RNP format was more efficient for the on-target editing and more specific, as it generated much less off-target cleavage compared to the DNA plasmid format. We believe the Cas9 RNPs differ from plasmid-based delivery of CRISPR components with regards to how quickly the components are expressed and how long they are present within the cell (Liang, et al., (2017)).

Two major kinetic mechanisms may explain why Cas9 RNPs are more efficient and specific than Cas9 DNA plasmids. First, Cas9 RNPs are pre-mixed functional complexes capable of cleaving target DNA right after delivery into the cell and do not need to be transcribed and translated in the cell as required by DNA plasmids. Second, rapid clearance of Cas9 RNPs from the cell may increase CRISPR specificity by reducing the amount of time that Cas9 is available for off-target cleavage while expression of Cas9 and gRNA from plasmid can continue indefinitely until the DNA is lost through cell division, providing more opportunity for off-target cleavage.

Although Cas9 RNP format is more specific compared to plasmid, it is not off-target free. Two high fidelity SpCas9 variants, SpCas9-HF1 (Kleinstiver, et al., (2016)) and eSpCas9 (Slaymaker, et al., (2016)) were identified that showed a comparable on-target cleavage activity to the wild-type SpCas9, but with no detectable off-target activity in genome-wide scale. These variants were identified and validated using the format of plasmid DNA transfection, which is not ideal for gene and cell therapies for the reasons described above. We used SpCas9 RNP format and re-validated the two high fidelity SpCas9 variants. Out results showed the on-target activity of eSpCas9 was dramatically dropped although their off-target number and activity were also low, but still detectable. Although no off-target was detected from SpCas9-HF1, its on-target activity was crippled with a two-digit drop for most of targets tested. Interestingly, some new off-targets were detected from eSpCas9. That may relate to the different experimental conditions, sequencing depth or the Cas9 structure RNP conformation changes. The discrepant results between the Cas9 RNP format in this study and the plasmid format in previous studies (Kleinstiver, et al., (2016), Slaymaker, et al., (2016)) needs to be further investigated. It is pivotal to explore more rationally engineered variants to identify and validate the high-fidelity Cas9 at the RNP format.

The variety of on- and off-target cleavage rates induced by CRISPR/Cas9 systems raises hope that better selection of target sites, possibly through rational design tool and/or a pre-screen in cells, can result in gene editing with improved specificity to the non-detectable level. Our study on 22 disease-associated SNP sites to simulate HDR-based gene correction demonstrated that it is possible to have gene edited by CRISPR/Cas9 with no detectable off-target if 2 to 3 high-score gRNAs per target are chosen through in silico CRISPR design tools to perform a pre-screen of editing efficiency and genome-wide off-target. Our results showed 5 (22.7%) of 22 high-scored gRNAs still created off-targets that were detected by TEG-seq. However, currently available design tools including the tools that we used in this study are only based on the mismatch information, such as the number of mismatch and position-weighted mismatches in their off-target scoring algorithms. The missed base or additional base that causes "bulge" in DNA:RNA duplex were not implemented in their off-target prediction algorithms. That was why 3 out of 5 off-targets with high score in this study were not predicted by the design tools used. An enhanced design algorithm (Xu, (2017) *CRISPR-Cas9* cleavage efficiency correlates strongly with targets gRNA folding stability: from physical mechanism to off-target assessment. Nature Com/Scientific Reports 7:143 DOI: 10.1038/s41598-017-00180-1) that allows to format single-base "bulge" for off-target prediction may provide more accurate predicting score and limit more off-targets.

The data from this study provides the information that may help for cell model development as well as the future regulatory process for therapeutic applications. An efficient and safe gene and cell therapy will rely on a right strategy and workflow started with a good gRNA design, the usage of high efficient and specific editing reagents and high sensitive off-target detection methods. Current CRISPR design tools need to be improved to recognize the "bulge" mismatch between RNA:DNA. Using the RNP format of high-fidelity Cas9 will maximize on-target editing activity and minimize the off-target cleavage. A high sensitive in cellulo detection method, such as TEG-seq for initial off-target screening before editing followed by validation using deep Targeted ION AMPLISEQ™ after editing could be a good strategy to restrain the off-targets to the safe level for cell and gene therapy.

Materials and Methods:

Cell Culture and Transfection

HEK293FT was used for on-target and off-target studies. DMEM complete medium with GLUTAMAX™, glucose and sodium pyruvate pre-added and 10% FBS (GIBCO) was used for cell culture. For on-target study, 96-well plate was used that contains 20,000 cells per well. The 100 ng of Cas9 protein and 20 ng of in vitro transcribed (IVT) gRNA were premixed and transfected using LIPOFECTAMINE® RNAiMAX Transfection Reagent following the manufacture's protocol and incubated for 48 hours at 37° C. with 5% $CO_2$ and harvested after 48 hours. For GUIDEseq off-target study, 6-well plate with 1.5 million cells per well was used. In DNA plasmid delivering format of Cas9/gRNA cloned in the all-in-one GENEART® CRISPR Nuclease Vector with OFP Reporter (Thermo Fisher Scientific), 3 µg plasmid and 50 pmol of dsTag were used. In RNP format, 3 µg of purified Cas9 protein and 1 ug of IVT-gRNA (ordered through Invitrogen Genome Engineering Services) and 50 pmol of dsTag were premixed and transfected using NEON™ Electroporation System 100 µl Kit (INVITROGEN™). The setting of Neon electroporation was 1400 voltage, 20 width and 2 pulses. Cells were incubated at 37° C. with 5% $CO_2$ and harvested after 48 hours.

Oligonucleotides and Double Strand DNA Tag and Adaptors

The oligonucleotide sequences for Ion-GUIDE-seq, PCR-targeted ION AMPLISEQ™ were listed in (Table 9) and ordered from ThermoFisher Scientific. Double strand DNA Tag (dsTag) and adaptors were annealed in the reaction containing 1×TE buffer, 100 mM NaCl and 50 µM of up- and low-oligos, at 75° C. for 5 minutes and gradually cool down to room temperature in 20 to 30 minutes. The annealed dsTag or adaptors (1 µg) and single strand oligo used for annealing were side by side resolved on 3% of agarose gel to make sure no single strand oligos were are visible in the annealed samples.

gRNA Template Preparation and In Vitro Transcription (IVT)

In vitro transcribed gRNAs were synthesized as described in previous publication (Liang, et al., (2015)). Briefly, the 80 bp cr/tracrRNA constant region was PCR amplified from the GENEART® CRISPR Nuclease Vector (1 ng) using the Constant Forward and Universal Reverse oligos (10 µM) and purified via agarose gel extraction. The 80 bp cr/tracrRNA PCR products (0.15 µM) was equally mixed with universal forward and reverse oligos (10 µM) as well as target-specific forward and reverse oligos (0.3 µM). The in vitro transcription of gRNA was carried out using TranscriptAid T7 High Yield Transcription Kit (ThermoFisher Scientific) following manufacturer's protocol. The gRNA product was purified using MEGACLEAR™ Transcription Clean-Up kit (Thermo Fisher Scientific) as described in the manual. The concentration of RNA was determined using QuBIT® RNA BR Assay Kit.

SpCas9 Expression and Purification.

For plasmid format, the SpCas9 and gRNA were cloned in the GENEART® CRISPR Nuclease Vector (ThermoFisher Scientific) following manufacture's protocol. The recombinant wild type SpCas9 and its variant proteins were initially constructed and purified as described (Kim, et al., (2014)).

GCD Assay (T7 Endonuclease I Assays)

The nuclease-induced indel formation was detected using GENEART® Genomic Cleavage Detection Kit (GCD) following manufacture's protocol (Thermo Fisher Scientific, cat. no. A24372). Follow the recommended guide lines, a pair of primers were designed for each targeted sample to amplified a 400-500 bp PCR product, in which the potential cleavage site is not in the center of the amplicon, so that detection reaction yields two distinct product bands. The percentage of cleavage was determined based on the intensities of cleaved and non-cleaved bands on 2% E-GEL® (Thermo Fisher Scientific) and quantitated using the Alpha Imager software (Bio-Rad).

Ion-GUIDE-Seq and TEG-Seq Using Ion Torrent Platform

The genomic DNA was extracted using PURELINK™ Genomic DNA Mini Kit (Invitrogen). Genomic DNA sample was fragmentized into 200-600 base pair range using ION XPRESS™ Plus Fragment Library Kit and performed in 96-well plate. Each fragmentation contains 50 µl reaction with 5 µl of ION SHEAR™ Plus 10× Buffer, 5 µl of ION SHEAR™ Plus Enzyme Mix and 300 ng of genomic DNA. The reaction was incubated for 10 minutes at 37° C., and terminated by adding 5 µl of Stop Buffer. The fragmented genomic DNA was cleaned up using 1.8× sample volume of AMPURE® XP beads (Agencourt) following standard protocol and eluted in 25 µl of TE buffer. The genomic DNA was ligated to Ion P1 adaptor using ION XPRESS™ Plus Fragment Library Kit and performed in 96-well plate. Each ligation contains 50 µl reaction with 10 µl of sheared DNA, 5 µl of 10× Ligation Buffer, 2 µl of P1 adaptor, 1 µl of 10 mM dNTP, 2 µl of DNA ligase, 4 µl of Nick Repair Polymerase and 26 µl of Nuclease-free water. The reaction was incubated at 37° C. for 15 minutes and inactivated at 72° C. for 5 minutes. The P1 ligated DNA sample was cleaned up using 1.5× sample volume of AMPURE® XP bead (Agencourt) following standard protocol and eluted in 25 µl of TE buffer. The first PCR was performed in two separated reactions (forward and reverse) for each sample. Each amplification contains 25 µl reaction with 4 µl of P1-ligated DNA, 5 µl of 5× ION AMPLISEQ™ HiFi Mix (ThermoFisher Scientifics, ION LIBRARY EQUALIZER™ Kit), 4 µl of 1 µM P1 primer, 4 µl of 1 µM F1 or R1 primer and 8 µl of $H_2O$. The amplification was initiated at 99° C. for 2 minutes, 17 cycles of 99° C. for 15 seconds and 60° C. for 60 seconds, followed by final extension at 60° C. for 5 minutes. The second PCR was also performed using different protocols for Ion-GUIDE-seq and TEG-seq.

For GUIDE-seq, the second PCR using standard F2 and R2 primers paired with P1 primer in two separated reactions (forward and reverse) for each sample. Each amplification contains 25 µl reaction with 2 µl of $1^{st}$ PCR product, 5 µl of 5× PHUSION® Green HF Buffer, 0.25 µl of PHUSION® Green Hot Start II High-Fidelity DNA Polymerase (2 U/μL) (ThermoFisher Scientific), 0.5 μl of 10 mM dNTP, 0.75 μl of 100% DMSO, 4 μl of 1 μM P1 primer, 4 μl of 1 μM 5P-F1 or 5P-R1 primer and 8.5 μl of $H_2O$. The amplification was initiated at 98° C. for 2 minutes followed by a touchdown program that includes 2 cycles of 66° C. for 15 seconds and 72° C. for 20 seconds, 2 cycles of 64° C. for 15 seconds and 72° C. for 20 seconds, 2 cycles of 62° C. for 15 seconds and 72° C. for 20 seconds, 2 cycles of 60° C. for 15 seconds and 72° C. for 20 seconds, 2 cycles of 58° C. for 15 seconds and 72° C. for 20 seconds, 8 cycles of 56° C. for 15 seconds and 72° C. for 20 seconds, and a final extension at 72° C. for 5 minutes. The sample was cleaned up using 1.5× sample volume of AMPURE® XP bead (Agencourt), the beads were washed twice with 70% Ethanol and resuspended in 20 μl of $H_2O$. The $2^{nd}$ PCR products were ligated to Ion barcoded "A" (BC-A) adaptor that contains a 5' phosphate in 30 μl reaction containing 3 μl 10× ligatin buffer, 0.6 μl 10 mM dNTP, 5 units of ligase, 1 μl of Ion 5p-BC-A adaptor and 4 μl of $2^{nd}$ PCR product for 15 minutes at 25° C. and 5 minutes at 72° C. The forward and reverse reactions were pooled together. The enrichment of targeted PCR product containing BSD fragment is further enriched using Ion Library Equalizer kit (ThermoFisher Scientific) with some modifications as following. The pooled forward and reverse reactions were cleaned with 1.5× sample volume of AMPURE® XP bead (Agencourt), the beads were washed twice with 70% ethanol and eluted in 10 μl of Low TE buffer. The $3^{rd}$ PCR containing 100 μl PLATINUM® HF Supermix, 5 μl eluted DNA from $2^{nd}$ PCR and 5 μl standard Ion P1 and A primers mix was initiated at 95° C. for 5 minutes, 10 cycles of 95° C. for 15 seconds, 58° C. for 15 seconds, 70° C. for 30 seconds followed by final extension at 70° C. for 3 minutes. The PCR product was cleaned using 1.5× sample volume of AMPURE® XP bead (Agencourt) as described above. The eluted product was qualified using QUBIT® dsDNA HS Assay kit (ThermoFisher Scientific) and loaded on Ion Chef for emulsion following manufacture's protocol.

For TEG-seq, the second PCR using 5' phosphate F2 and R2 primers paired with P1 primer in two separated reactions (forward and reverse) for each sample. Each amplification contains 25 μl reaction with 2 μl of $1^{st}$ PCR product, 5 μl of 5× PHUSION® Green HF Buffer, 0.25 μl of PHUSION® Green Hot Start II High-Fidelity DNA Polymerase (2 U/μL) (ThermoFisher Scientific), 0.5 μl of 10 mM dNTP, 0.75 μl of 100% DMSO, 4 μl of 1 uM P1 primer, 4 μl of 1 uM 5P-F2 or 5P-R2 primer and 8.5 μl of $H_2O$. The amplification was initiated at 98° C. for 2 minutes followed by a touchdown program that includes 2 cycles of 66° C. for 15 seconds and 72° C. for 20 seconds, 2 cycles of 64° C. for 15 seconds and 72° C. for 20 seconds, 2 cycles of 62° C. for 15 seconds and 72° C. for 20 seconds, 2 cycles of 60° C. for 15 seconds and 72° C. for 20 seconds, 2 cycles of 58° C. for 15 seconds and 72° C. for 20 seconds, 8 cycles of 56° C. for 15 seconds and 72° C. for 20 seconds, and a final extension at 72° C. for 5 minutes. The sample was cleaned up using 1.5× sample volume of AMPURE® XP bead (Agencourt), the beads were washed twice with 70% ethanol and resuspended in 20 μl of PHUSION®. The $2^{nd}$ PCR products were ligated to the non-phosphate Ion barcoded "A" (BC-A) in 30 μl reaction containing 3 μl 10× ligation buffer, 0.6 μl 10 mM dNTP, 5 units of ligase, 1 μl of Ion BC-A adaptor and 4 μl of $2^{nd}$ PCR product for 15 minutes at 25° C. and 5 minutes at 72° C. The forward and reverse reactions were pooled together. The enrichment of targeted PCR product containing BSD fragment is further enriched using Ion Library Equalizer kit (ThermoFisher Scientific) with some modifications as following. The pooled forward and reverse reactions were cleaned with 1.5× sample volume of AMPURE® XP bead (Agencourt), the beads were washed twice with 70% Ethanol and resuspended in 110 μl of equalized PCR reaction containing 100 μl PLATINUM® HF Supermix and 10 μl Equalizer Primers. The amplification was initiated at 98° C. for 2 minutes, 10 cycles of 98° C. for 15 seconds and 64° C. for 60 seconds, followed by final extension at 72° C. for 2 minutes. To 110 μl of PCR reaction, adding 50 μl $H_2O$ and 30 μl Capture oligo and incubated 5 minutes in room temperature. To each 190 μl reaction, adding 10 μl of washed equalizer beads and incubated 5 minutes in room temperature. Wash twice with 300 μl Equalizer Wash Buffer. Elute final product in 25 μl of Equalizer Elution Buffer at 32° C. for 5 minutes. The eluted product can be qualified using QUBIT® dsDNA HS Assay kit (Thermo Fisher Scientific) and loaded on Ion Chef for emulsion following manufacture's protocol.

Targeted ION AMPLISEQ™ Validation

All candidates of off-targets from TEG-seq were validated using PCR-targeted ION AMPLISEQ™. The primers were designed to amplify 200-300 base of PCR product, in which the cleavage sites are in the middle of product. The PCR reaction contains 50 ng of genomic DNA, 5 μl of 5× PHUSION® Green HF Buffer, 0.25 μl of PHUSION® Green Hot Start II High-Fidelity DNA Polymerase (2 U/μL) (ThermoFisher Scientific), 0.5 μl of 10 mM dNTP, 0.75 μl of 100% DMSO, 1 μl mixed primer (10 μM) and in the final of 25 μl total volume. The amplification was initiated at 98° C. for 2 minutes, followed by a touchdown program that includes 2 cycles of 66° C. for 15 seconds and 72° C. for 20 seconds, 2 cycles of 64° C. for 15 seconds and 72° C. for 20 seconds, 2 cycles of 62° C. for 15 seconds and 72° C. for 20 seconds, 2 cycles of 60° C. for 15 seconds and 72° C. for 20 seconds, 2 cycles of 58° C. for 15 seconds and 72° C. for 20 seconds, 20 cycles of 56° C. for 15 seconds and 72° C. for 20 seconds, and a final extension at 72° C. for 5 minutes. The amplicons were purified using PURELINK™ PCR Purification kit (Invitrogen), treated with T4 kinase (Invitrogen) in 10 μl reaction containing 2 μl 5× forward buffer, 1 μl 10 mM ATP, 2.5 μl $H_2O$ and 4 μl purified PCR product for 20 minutes at room temperature and 30 minutes at 75° C. The PCR product was measured using Nano Drop (Thermo Fisher). Barcoded adaptor A (BC-A) and P1 were ligated to PCR product in a 25 μl reaction containing 2.5 μl 10× ligase buffer, 2.5 units of ligase (Invitrogen), 0.5 μl 10 mM dNTP, 0.5 μl Ion P1 adaptor, 0.5 μl BC-A adaptor and 2.5 μl kinase-treated PCR product for 30 minutes at 16° C., 30 minutes at 25° C., and 30 minutes at 75° C. The products were cleaned up using 1.5× sample volume of AMPURE® XP bead (Agencourt), washed twice with 70% Ethanol and resuspended in 20 μl of $H_2O$. The emulsion PCR was performed following manufacture protocol (Ion-Torrent). All samples were run NGS on ION PGM™ 318 chips.

Data Analysis for TEG-Seq and Targeted ION AMPLISEQ™

NGS reads from TEG-seq and Ion-Guide-seq were first aligned to human genome reference (hg19). To make more comparable between different samples and experiments, our non-targeting mapped reads is from one to five million for each sample from all ION PGM™ runs. If mapped reads is less than one million, we performed a $2^{nd}$ run and combined the reads from two runs for analysis. Mapped reads were further processed through in-house developed plug-in software that can, 1) sort barcodes for different samples, 2) pileup and count reads based on the gRNA genome positions. The candidates for potential CRISPR/Cas9 induced-DSBsites were compared to the control sample without CRISPR/Cas9 treatment to determine if the candidates are related to CRISPR/Cas9 induced DSBsites. To compare different samples from different experiments and different NGS runs, reads from all samples were normalized using RPM (Reads Per Million of mapped read).

NGS reads from the Targeted ION AMPLISEQ™ were aligned to the corresponding reference of PCR product. Our targeting mapped reads for each amplicon is 30,000 to 150,000. If the mapped reads is less than 30,000, $2^{nd}$ run was performed and reads from two runs were pooled for downstream data analysis. The Bam files were uploaded to Integrative Genomics Viewer (IGV). The percentage of indel was determined by indel reads divided by the total mapped reads at the cleavage site.

TABLE 5

Primer/Adapter Sequence

| Name | Sequence | SEQ ID |
|---|---|---|
| dsTag-Up | 5'-EZTTAATTGAGTTGTCATATGTTAATAACGGZFT-3' | 47 |
| dsTag-Down | 5'-FZACCGTTATTAACATATGACAACTCAATTAFFC-3' | 48 |
| P1 Adaptor-Up | 5'-CCACTACGCCTCCGCTTTCCTCTCTATGGGC AGTCGGTGA*-3' | 49 |
| P1 Adaptor-Down | 5'-TCACCGACTGCCCATAGAGAGGA*C*C-3' | 50 |
| P1 primer | 5'-CCACTACGCCTCCGCTTTCCTCTCTATG-3' | 51 |
| F1 primer | 5'-GTTTAATTGAGTTGTCATATGTTAAT-3' | 52 |
| R1 primer | 5'-ATACCGTTATTAACATATGACAACTC-3' | 53 |
| 5p-F2 primer | 5'-PHO-GTTGTCATATGTTAATAACGGTAT-3' | 54 |
| 5p-R2 primer | 5'-PHO-TAACATATGACAACTCAATTAAAC-3' | 55 |
| BC-A adaptor-Up | 5'-CCATCTCATCCCT*G*CGTGTCTCCGACTCAGNNNNN NNNNNNGAT-3' | 56 |
| BC-A adaptor-Down | 5'-ATCGTTACCTTAGCTGAGTCGGAGACACGC-3' | 57 |
| Equalizer A Primer | 5'-GGGAAAAGATGG/iSp18/CCATCTCATCCCTGCGTG TC-3' | 58 & 243 |
| Equalizer P1-Primer | 5-CCACTACGCCTCCGCTTTCCTCTCTATG-3' | 59 |
| Capture oligo | 5'-CCATCTTTTCCC/3BioTEG/ | 60 |

TABLE 6 gRNA sites for HEK1, VEG1, VEG3 and HEK4

| Name of gRNA site | gRNA sequence | MIT design score | SEQ ID |
|---|---|---|---|
| HEK1 | GGGAAAGACCCAGCATCCGTGGG | 76 | 61 |
| HEK4 | GGCACTGCGGCTGGAGGTGGGGG | 24 | 62 |
| VEG1 | GGGTGGGGGGAGTTTGCTCCTGG | 55 | 63 |
| VEG3 | GGTGAGTGAGTGTGTGCGTGTGG | 27 | 64 |

TABLE 7

Comparison of on-target activity using RNP of eSpCas9-1.1, SpCas9-HF1 and wide-type SpCas9

|  | WT | eSpCas9-1.1 | SpCas9-HF1 |
|---|---|---|---|
| EMX1-1 | 100 | 25 | 0 |
| EMX1-2 | 100 | 55 | 19 |
| EMX1-3 | 100 | 34 | 0 |
| EMX1-5 | 100 | 0 | 0 |
| EMX1-6 | 100 | 42 | 0 |
| EMX1-8 | 100 | 13 | 0 |
| EMX1-9 | 100 | 0 | 0 |
| DNMT1-1 | 100 | 4 | 0 |

TABLE 7-continued

Comparison of on-target activity using RNP of eSpCas9-1.1, SpCas9-HF1 and wide-type SpCas9

|  | WT | eSpCas9-1.1 | SpCas9-HF1 |
|---|---|---|---|
| VegFA-2 | 100 | 59 | 0 |
| VegFA-3 | 100 | 2 | 0 |
| VegFA-5 | 100 | 105 | 54 |
| HPRT | 100 | 97 | 60 |
| CMPK1 T1 | 100 | 88 | 9 |
| CMPK1 T2 | 100 | 18 | 0 |
| PRKCG | 100 | 80 | 23 |
| Casp8 | 100 | 9 | 0 |
| Srms T1 | 100 | 8 | 0 |
| Srms T2 | 100 | 20 | 0 |
| BTK T1 | 100 | 39 | 5 |

TABLE 7-continued

Comparison of on-target activity using RNP of eSpCas9-1.1, SpCas9-HF1 and wide-type SpCas9

|         | WT  | eSpCas9-1.1 | SpCas9-HF1 |
|---------|-----|-------------|------------|
| BTK T2  | 100 | 9           | 26         |
| IKBKE T1| 100 | 82          | 0          |
| PFKP T1 | 100 | 64          | 0          |
| CPSF1 T1| 100 | 18          | 0          |
| Average | 100 | 37.86       | 8.49       |
| >90%    |     | 0.1         | 0.0        |
| >50%    |     | 0.2         | 0.1        |
| >10%    |     | 0.5         | 0.1        |
| 0       |     | 0.09        | 0.70       |

Table 7 shows a comparison of on-target activity using GCD assay on 23 more loci transfected with RNP of eSpCas9-1.1, SpCas9-HF1 and wide-type SpCas9. The % of cleavage efficiency from eSpCas9-1.1 and SpCas9-HF1 was normalized against to wild type of Cas9 that are defined as 100%

TABLE 8

Off-targets from HEK4 detected by Ion-GUIDE-seq and TEG-seq using the plasmid format

| Name    | Position         | gRNA                      | SEQ ID | PAM | RPM_TEG-seq | RPM_Ion-GUIDE-seq |
|---------|------------------|---------------------------|--------|-----|-------------|-------------------|
| HEK4-5* | chr20: 31349772  | GGCACTGCGGCTGGAGGTGG      | 65     | GGG | 14171       | 671               |
| HEK4-1  | chr20: 60010563  | T..........C.....A..      | 66     | TGG | 9818        | 448               |
| HEK4-2  | chr19: 33382080  | ...T.............G..      | 67     | TGG | 1861        | 139               |
| HEK4-3  | chr10: 126694874 | .....GA.............      | 68     | GGG | 37606       | 1130              |
| HEK4-4  | chr10: 77103119  | ....TCA.............      | 69     | AGG | 640         | 0                 |
| HEK4-6  | chr15: 41044241  | ...G.......G........      | 70     | AGG | 2566        | 12                |
| HEK4-7  | chr19: 38616186  | .......A.A....G.....      | 71     | GGG | 272         | 0                 |
| HEK4-8  | chr13: 39262929  | A...G.......A.......      | 72     | TGG | 3209        | 462               |
| HEK4-9  | chr6: 160517881  | ........T.....G.....      | 73     | TGG | 613         | 13                |
| HEK4-10 | chr10: 13692637  | .......G......G..A..      | 74     | GGG | 394         | 0                 |
| HEK4-11 | chr13: 27629410  | .......G..T.........      | 75     | GGG | 285         | 0                 |
| HEK4-12 | chr7: 54561437   | A.G..........G.....       | 76     | TGG | 11899       | 405               |
| HEK4-13 | chr20: 45343010  | .......A...G........      | 77     | GGG | 846         | 0                 |
| HEK4-14 | chr17: 75429279  | .A...CA.........A...      | 78     | TGG | 962         | 25                |
| HEK4-15 | chr20: 1151854   | .......T.....C......      | 79     | AGG | 2219        | 204               |
| HEK4-16 | chr16: 50300347  | A......T......G..A..      | 80     | GGG | 139         | 2840              |
| HEK4-17 | chr19: 41220525  | ....A..T.....A......      | 81     | GGG | 61          | 0                 |
| HEK4-18 | chr20: 60895671  | .....A..A..........C      | 82     | TGG | 189         | 0                 |
| HEK4-19 | chr1: 171018460  | .C.....G......G.....      | 83     | GGG | 299         | 0                 |
| HEK4-20 | chr17: 176301    | T......T........A...      | 84     | GGG | 399         | 0                 |
| HEK4-21 | chr3: 51725451   | ...T...T.........A..      | 85     | TGG | 1           | 0                 |
| HEK4-22 | chr7: 110143150  | ........A...A.......      | 86     | AGG | 1           | 0                 |
| HEK4-23 | chr18: 37194557  | ..........G......C..      | 87     | GGG | 2343        | 14                |
| HEK4-24 | chr20: 37471343  | A......T.C....G.....      | 88     | GGG | 4           | 0                 |
| HEK4-25 | chr4: 56815199   | ....A............C..      | 89     | AGG | 5142        | 6                 |
| HEK4-26 | chr19: 46887173  | .AGG..........G.....      | 90     | AGG | 10          | 0                 |
| HEK4-27 | chr3: 10418955   | ...T.C..A...........      | 91     | GGG | 1           | 0                 |
| HEK4-28 | chr7: 134872031  | A......T......G..A..      | 92     | CGG | 116         | 101               |

TABLE 8-continued

Off-targets from HEK4 detected by Ion-GUIDE-seq
and TEG-seq using the plasmid format

| Name | Position | gRNA | SEQ ID | PAM | RPM_TEG-seq | RPM_Ion-GUIDE-seq |
|---|---|---|---|---|---|---|
| HEK4-29 | chr9: 133039176 | .T......A........A.. | 93 | GGG | 23 | 0 |
| HEK4-30 | chr3: 53375995 | ...T...A...CA....... | 94 | TGG | 2 | 0 |
| HEK4-31 | chr7: 1397398 | A.......A.....GA.... | 95 | AGG | 91 | 0 |
| HEK4-32 | chr3: 49055364 | ..G................. | 96 | GAA | 573 | 1566 |
| HEK4-33 | chr1: 201067377 | ........T...A.......C | 97 | AGG | 1 | 0 |
| HEK4-34 | chr22: 30130865 | ...TG......CA....... | 98 | AGG | 199 | 0 |
| HEK4-35 | chr19: 1295086 | .A.....A...A........ | 99 | GGG | 1 | 0 |
| HEK4-36 | chr8: 119227145 | .....AAT...........A | 100 | AGG | 10 | 0 |
| HEK4-39 | chr14: 24740271 | ........CA....G....A | 101 | GGG | 117 | 0 |
| HEK4-40 | chr13: 88900992 | CA........A......... | 102 | TGG | 241 | 0 |
| HEK4-41 | chr20: 60080554 | A.......A.A......A.. | 103 | CGG | 167 | 0 |
| HEK4-44 | chr7: 139244407 | .C.......A.......A.. | 104 | GGG | 115 | 0 |
| HEK4-45 | chr17: 29815563 | ...G.......C........ | 105 | GGC | 133 | 90 |
| HEK4-46 | chr6: 36761680 | CC.....G............ | 106 | GGG | 3 | 0 |
| HEK4-53 | chr9: 136602370 | .......G...A....A... | 107 | GGG | 2 | 0 |
| HEK4-55 | chr20: 61810738 | .T...........C..A... | 108 | CGG | 179 | 0 |
| HEK4-56 | chr16: 28266968 | ...T..T...........A. | 109 | CGG | 15 | 0 |
| HEK4-57 | chr12: 53453556 | T.G............AG.. | 110 | AGG | 129 | 0 |
| HEK4-58 | chr14: 21993454 | ..T..A........G..A.. | 111 | CGG | 1 | 0 |
| HEK4-59 | chr3: 52321883 | .....C.....C....C..T | 112 | GGG | 205 | 0 |
| HEK4-60 | chr3: 23651527 | .....A..A.G......... | 113 | AGG | 6 | 0 |
| HEK4-61 | chr15: 34081545 | A......TA..AA....... | 114 | AGG | 1 | 0 |
| HEK4-65 | chr1: 204463911 | ...G............CC.. | 115 | CGG | 1 | 0 |
| HEK4-66 | chr17: 16982385 | CAG........A..G..... | 116 | CGG | 102 | 0 |
| HEK4-68 | chr10: 73435247 | .TA............C..... | 117 | TGG | 1 | 0 |
| HEK4-74 | chr2: 241640853 | ..GG.......C........ | 118 | TGG | 84 | 0 |
| HEK4-77 | chr4: 183980137 | .......T...AA....... | 119 | GAG | 60 | 0 |
| HEK4-80 | chr16: 89469251 | ..........GA........ | 120 | GCG | 19 | 0 |
| HEK4-87 | chr12: 131356926 | ...A..G.....C.......T | 121 | AGG | 400 | 0 |
| HEK4-88 | chr8: 20854500 | .......G........AC.. | 122 | GGG | 4 | 0 |
| HEK4-108 | chr16: 67742859 | A......C...CA......A | 123 | GGG | 56 | 0 |
| HEK4-113 | chr13: 48891654 | .....C.A...C.......C | 124 | TGG | 1 | 0 |
| HEK4-119 | chr6: 40975969 | A....CAT....A......T | 125 | GGG | 26 | 0 |
| HEK4-122 | chr5: 139284046 | .......A.....C...C.. | 126 | CGG | 30 | 0 |
| HEK4-127 | chr6: 41374185 | .....-.........A... | 127 | GGG | 18181 | 4993 |
| HEK4-132 | chr22: 41620072 | ..GCA........A.... | 128 | TGG | 1106 | 193 |
| New-HEK4-1 | chr19: 4103518 | ...A....A....A.AG.G.. | 129 | CGG | 16 | 0 |

TABLE 8-continued

Off-targets from HEK4 detected by Ion-GUIDE-seq
and TEG-seq using the plasmid format

| Name | Position | gRNA | SEQ ID | PAM | RPM_TEG-seq | RPM_Ion-GUIDE-seq |
|---|---|---|---|---|---|---|
| New-HEK4-2 | chr19: 2474632 | .......-.........C.. | 130 | GGG | 829 | 28 |
| New-HEK4-3 | chr6: 159828153 | .....-G.............. | 131 | AGG | 11 | 0 |
| New-HEK4-4 | chr19: 42618262 | ...TA.A....A..T..... | 132 | AGG | 15 | 0 |
| New-HEK4-5 | chr20: 59063395 | ....G..A.......A.G.A | 133 | AGG | 4 | 0 |
| New-HEK4-6 | chr4: 153020013 | .A...A.A...GA....A.. | 134 | CGG | 6 | 0 |
| New-HEK4-7 | chr2: 25502012 | ....T.AAT.....C..G.. | 135 | AGG | 2 | 0 |
| New-HEK4-8 | chr4: 189190971 | ....GG.A..AG.....A.. | 136 | CGG | 34 | 0 |
| New-HEK4-9 | chr10: 6268265 | .....GG......-C....... | 137 | AGG | 20 | 237 |
| New-HEK4-10 | chr15: 29121806 | ........-..GA........ | 138 | AGG | 248 | 0 |
| New-HEK4-11 | chr2: 1708257 | .....a..C.A.G..A...... | 139 | GGG | 3 | 0 |
| New-HEK4-12 | chr13: 27580667 | .C.C.G.G...G..... | 140 | GGG | 6 | 0 |
| New-HEK4-13 | chr5: 178871203 | ..AG...T...C..GC.... | 141 | TGG | 3 | 0 |
| New-HEK4-14 | chr3: 37781680 | ....G..G...A..GCT... | 142 | AGG | 4 | 0 |
| New-HEK4-15 | chr10: 8093483 | ...C.......-..C..C.. | 143 | CGG | 95 | 0 |
| New-HEK4-16 | chr6: 119056796 | A...G..A.C......CA.. | 144 | AGG | 4 | 0 |
| New-HEK4-17 | chrX: 104846041 | A..T....-.........A.. | 145 | GGG | 9292 | 111 |
| New-HEK4-18 | chr1: 71218351 | AC....CG..G...G..... | 146 | TGG | 785 | 0 |
| New-HEK4-19 | chr2: 234737154 | ...T...T..a.A.....G.A | 147 | GGG | 65 | 0 |
| New-HEK4-20 | chr2: 43090287 | .A.......-TT.....A... | 148 | AGG | 5 | 0 |
| New-HEK4-21 | chr17: 26823462 | ...-...G.C......TG.. | 149 | AGG | 3 | 0 |
| New-HEK4-22 | chr11: 99290407 | TT..G.AG........TG.. | 150 | GGG | 2 | 34 |
| New-HEK4-23 | chr10: 30378103 | ........-T.....G..... | 151 | AGG | 71 | 0 |
| New-HEK4-24 | chr19: 33410105 | AC..T.T........C.C.. | 152 | TGG | 19 | 0 |
| New-HEK4-25 | chr10: 72259826 | .....-.CA......TC.... | 153 | TGG | 8 | 0 |
| New-HEK4-26 | chr10: 133908078 | ...T...-......TAC... | 154 | GGG | 31 | 0 |
| New-HEK4-27 | chr1: 29440356 | TA....CT......C.AG.. | 155 | AGG | 1262 | 0 |
| New-HEK4-28 | chr3: 17783613 | TT.C.....CC.A......C. | 156 | GGG | 21 | 0 |
| New-HEK4-29 | chr5: 51138758 | AA.C......GG..G..G.. | 157 | GGG | 8 | 0 |
| New-HEK4-30 | chr3: 154937526 | CA.....G...CT.TT.... | 158 | GGG | 2 | 0 |

TABLE 8-continued

Off-targets from HEK4 detected by Ion-GUIDE-seq
and TEG-seq using the plasmid format

| Name | Position | gRNA | SEQ ID | PAM | RPM_TEG-seq | RPM_Ion-GUIDE-seq |
|---|---|---|---|---|---|---|
| New-HEK4-31 | chr12: 68999879 | .AG..G.....G..G...G.. | 159 | GGG | 4 | 0 |
| New-HEK4-32 | chr5: 149772888 | ....G..-..G...-..... | 160 | TGG | 4 | 0 |

Table 8 shows a list of off-targets from HEK4 detected by Ion-GUIDE-seq in this study and also listed in the previously published data (Tsai, et al., (2015)). Data labeled 'New-HEK4-_" refer to off-targets from HEK4 detected in this study, but not presented in Tsai, et al., (2015).

TABLE 9

Detection level of top 30 HEK4 on-and off-targets presented in Tsai, et al., (2015) using Targeted AmpliSeq (%), TEG-seq and Ion-GUIDE-seq (RPM). Stars are on-targets.

| Target | Sequence | Seq ID | PAM | AmpliSeq (%) | TEG-Seq (RMP) | Ion-GUIDE-Seq (RPM) |
|---|---|---|---|---|---|---|
| HEK4-5* | GGCACTGCGGCTGGAGGTGG | 161 | GGG | 40.3 | 11045 | 436 |
| HEK4-3 | .....GA.............. | 162 | GGG | 99 | 31102 | 0 |
| HEK4-12 | A.G...........G..... | 163 | TGG | 10.7 | 14092 | 665 |
| HEK4-25 | ....A.............C.. | 164 | AGG | 10.5 | 6425 | 81 |
| HEK4-7 | .......A.A....G..... | 165 | GGG | 9.8 | 237 | 0 |
| HEK4-1 | T..........C.....A.. | 166 | TGG | 5.6 | 6992 | 96 |
| HEK4-2 | ...T.............G.. | 167 | TGG | 2.2 | 1689 | 1921 |
| HEK4-9 | ........T.....G..... | 168 | TGG | 1.6 | 615 | 6 |
| HEK4-15 | .......T.....C...... | 169 | AGG | 1.54 | 2000 | 91 |
| HEK4-8 | A...G.......A........ | 170 | TGG | 1.4 | 1906 | 475 |
| HEK4-6 | ...G.......G........ | 171 | AGG | 1.4 | 1599 | 172 |
| HEK4-26 | .AGG..........G..... | 172 | AGG | 1.1 | 12 | 0 |
| HEK4-4 | ....TCA.............. | 173 | AGG | 0.5 | 632 | 1646 |
| HEK4-16 | A......T.......G..A.. | 174 | GGG | 0.32 | 449 | 1441 |
| HEK4-13 | .......A..G.......... | 175 | GGG | 0.32 | 428 | 20 |
| HEK4-11 | .......G..T.......... | 176 | GGG | 0.3 | 163 | 95 |
| HEK4-23 | ..........G......C.. | 177 | GGG | 0.26 | 1192 | 135 |
| HEK4-20 | T......T........A... | 178 | GGG | 0.22 | 591 | 0 |
| HEK4-14 | .A...CA.........A... | 179 | TGG | 0.21 | 525 | 80 |
| HEK4-19 | .C.....G......G..... | 180 | GGG | 0.12 | 156 | 124 |
| HEK4-10 | .......G......G..A.. | 181 | GGG | 0.04 | 235 | 0 |
| HEK4-18 | .....A..A..........C | 182 | TGG | 0.04 | 96 | 0 |
| HEK4-27 | ...T.C..A............ | 183 | GGG | 0.03 | 506 | 0 |
| HEK4-28 | A......T.......G..A.. | 184 | CGG | 0.02 | 58 | 51 |
| HEK4-21 | ...T...T.........A.. | 185 | TGG | 0.02 | 2 | 0 |
| HEK4-30 | ...T...A...CA....... | 186 | TGG | 0.02 | 16 | 0 |

TABLE 9-continued

Detection level of top 30 HEK4 on-and off-targets presented in Tsai, et al., (2015) using Targeted AmpliSeq (%), TEG-seq and Ion-GUIDE-seq (RPM). Stars are on-targets.

| Target | Sequence | Seq ID | PAM | AmpliSeq (%) | TEG-Seq (RMP) | Ion-GUIDE-Seq (RPM) |
|---|---|---|---|---|---|---|
| HEK4-29 | .T......A........A.. | 187 | GGG | 0.01 | 12 | 0 |
| HEK4-17 | ....A..T.....A....... | 188 | GGG | 0 | 31 | 0 |
| HEK4-22 | ........A...A....... | 189 | AGG | 0 | 0 | 0 |
| HEK4-24 | A......T.C....G..... | 190 | GGG | 0 | 2 | 0 |

TABLE 10

Detection level on on- and off-targets from VEG1 (top 10), VEG1 (top 15) and HEK1 (top5) presented in Tsai, et al., (2015) using Targeted AmpliSeq (%), TEG-seq and Ion-Guide-seq (RPM). Stars are on-targets.

| Target | | Guide sequence | SEQ ID | PAM | % AmpliSeq | RPM TEG-seq | Ion GUIDE-seq |
|---|---|---|---|---|---|---|---|
| VEG1 | VEG1-2* | GGGTGGGGGGAGTTTGCTCC | 191 | TGG | 24 | 1186 | 274.7 |
| | VEG1-1 | ..A...A............ | 192 | TGG | 9.8 | 1795 | 105.2 |
| | VEG1-6 | C..G..A............ | 193 | TGG | 1 | 422 | 707.3 |
| | VEG1-4 | ...GA....A......... | 194 | TGG | 0.9 | 4 | 0.0 |
| | VEG1-5 | ...A...T........... | 195 | TGG | 0.5 | 5 | 0.0 |
| | VEG1-3 | TA....A......C..... | 196 | TGG | 0.1 | 12 | 0.0 |
| | VEG1-8 | ................C.. | 197 | AGG | 0.1 | 0 | 0.0 |
| | VEG1-7 | CT.GT.......C...... | 198 | AGG | 0 | 0 | 2.2 |
| | VEG1-9 | .C........T........ | 199 | CGG | 0 | 0 | 0.0 |
| | VEG1-10 | .T.G...TA.......... | 200 | AGG | 0 | 0 | 0.0 |
| VEG3 | VEG3-3* | GGTGAGTGAGTGTGTGCGTG | 201 | TGG | 5.6 | 88 | 79.9 |
| | VEG3-1 | A...............T... | 202 | GGG | 5.7 | 24 | 37.1 |
| | VEG3-4 | T...G............... | 203 | AGG | 1.3 | 9 | 18.0 |
| | VEG3-14 | C.C...............C. | 204 | GGG | 0.57 | 0 | 0.0 |
| | VEG3-8 | A....A........T..... | 205 | TGG | 0.48 | 6 | 0.0 |
| | VEG3-15 | .................T... | 2-6 | AGG | 0.43 | 2 | 0.0 |
| | VEG3-2 | A.A...............A.. | 2-7 | AGG | 0.29 | 2 | 0.0 |
| | VEG3-9 | T......A......T..... | 208 | TGG | 0.25 | 0 | 0.0 |
| | VEG3-11 | A.C.....G........... | 209 | GGG | 0.2 | 2 | 2.1 |
| | VEG3-12 | A...T............... | 210 | TGG | 0.1 | 0 | 0.0 |
| | VEG3-5 | .C...........A...... | 211 | TGG | 0.04 | 1 | 0.0 |
| | VEG3-6 | ...........C.....G. | 212 | TGG | 0 | 0 | 0.0 |
| | VEG3-7 | .T.......A.......... | 213 | AGG | 0 | 0 | 0.0 |
| | VEG3-10 | AC..T............... | 214 | AGG | 0 | 0 | 0.0 |
| | VEG3-13 | T...G............... | 215 | AGA | 0 | 0 | 0.0 |
| HEK1 | HEK1-1* | GGGAAAGACCCAGCATCCGT | 216 | GGG | 57.6 | 20070 | 689.7 |
| | HEK1-2 | .......T..........T. | 217 | TGG | 6 | 44 | 43.7 |
| | HEK1-3 | ......AG..........C. | 218 | TGG | 0 | 0 | 0.0 |
| | HEK1-4 | .....G...........TG | 219 | GGG | 0 | 0 | 0.0 |
| | HEK1-5 | ......T...........AA | 220 | TGG | 0 | 0 | 0.0 |

TABLE 11

Data used to generate FIG. 5.

| Name | RPM Plasmid | RPM RNP |
|---|---|---|
| VEG1-2* | 1186 | 3556 |
| VEG1-1 | 422 | 1155 |
| VEG1-3 | 1795 | 602 |
| VEG1-4 | 5 | 0 |
| VEG1-7 | 4 | 0 |
| New VEG1-1 | 4 | 0 |
| New VEG1-2 | 7 | 0 |
| VEG3-3* | 88 | 3439 |
| VEG3-1 | 24 | 245 |
| VEG3-2 | 2 | 3 |
| VEG3-4 | 9 | 0 |
| VEG3-5 | 1 | 0 |
| VEG3-8 | 6 | 0 |
| VEG3-15 | 2 | 0 |
| HEK1-1* | 13654 | 33979 |
| New HEK1-1 | 596 | 189 |
| HEK1-2 | 44 | 0 |

TABLE 12 gRNA design for SNP correction on genetic disorders

| Target No | Genetic Disorder | Gene | dbSNP# | Sequence of SNP, gRNA and flanking region | SEQ ID | MIT Score | TF Score |
|---|---|---|---|---|---|---|---|
| 1 | Cystic fibrosis | CFTR | rs75096551 | TCTTACCATATTTGACTTCAT*CCAG*[A/G]TA TGTAAAAATAAGTACCGTTAAGT | 211 | 61 | 76 |
| 2 | | CFTR | rs121909045 | AGAGACCATGCAGAGGTCGCCTC*TG*[C/*G*/ T]AAAAGGCCAGCGTTGTCTCCAAACT | 222 | 84 | 84 |
| 3 | Muscular Dystrophy | SMCHD1 | rs397514623 | AATATGCTGGTTTCATAACAGGCTC[*C*/T]*CT* GATAGATTGTCAGTAACTTGGCC | 223 | 74 | 80 |
| 4 | | SMCHD1 | rs387907319 | TTATCCGTTATCAT*CCA*TTCTTATA[-/TG ATA]GAGAAACTTACCCTGATGATCCATG | 224 | 49 | 78 |
| 5 | | SGCG | rs104894422 | TCTGTGGCCGGTGTGAGCACCACGT[A/G] CC*AGG*AGCACAGCCACATCTGCCTC | 225 | 77 | 83 |
| 6 | Sickle Cell Anemia | HBB | rs33940204 | AACCTCAAGGGCA*CCT*TTGCCACAC[C/G/ T]GAGTGAGCTGCACTGTGACAAGCTG | 226 | 70 | 80 |
| 7 | | HBB | rs33930165 | AGACACCATGGTGCATCTGACT*CCT*[A/C/ G]AGGAGAAGTCTGCCGTTACTGCCCT | 227 | 80 | 90 |
| 8 | Hemophilia B | F9-1 | rs587776735 | CTGAATTTTGGAAGCAGTATGT*TGG*[C/T] AAGCAATTCATTTTATCCTCTAGCT | 228 | 56 | 78 |
| 9 | | F10 | rs137852223 | TTCAGGTAAATTGGAAGAGTTTGTT[C/T] *AAG*GGAACCTTGAGAGAATGTAT | 229 | 50 | 80 |
| 10 | | F9-2 | rs267606792 | TTGAATGGTAAAGTTGATGCATTCT[C/G] TGG*AGG*CTCTATCGTTAATGAAAAA | 230 | 62 | 86 |
| 11 | Diabetes | LIPC | rs113298164 | AATAAAACGTATTCCTTTCTTATCA[C/T] GC*TGG*ATGTGGATATCGGCGAGCTG | 231 | 83 | 88 |
| 12 | | INS1 | rs80356668 | TACCTAGTGTGCGGGGAACG*AGG*CT[C/G/ T]CTTCTACACACCCAAGACCCGCCGG | 232 | 92 | 90 |
| 13 | | INS1 | rs121918101 | TGTGAACCAACACCTGTGCGGCTCA[C/G] A*CCT*GGTGGAAGCTCTCTACCTAGT | 233 | 74 | 85 |
| 14 | Polycystic kidney disease | PKD1 | rs199476102 | TGTTCCTGCGCAGGCTGCG*CCT*CTG[A/G] ATGGGCCTCAGCAAGGTCAAGG*AGG* | 234 | 69 | 83 |
| 15 | | PKD1 | rs199476094 | GGTGGTGCTCGGGGTAGCCTACG*CC*[C/ T]AGCTGGCCATCCTGGTAGGTGACTG | 235 | 68 | 84 |
| 16 | | PKD1 | rs199476095 | CGAGGCCCTGCTCAC*CCA*GTTTGAC[C/T] GACTCAACCAGGCCACAGAGGACGT | 236 | 93 | 89 |
| 17 | Haemo- chromatosis | HFE2 | rs74315324 | TGTTGGGGGGTGCCCT*CCA*AGTCAG[C/T] GACTCTCTCGATCAGAGCGCAATCG | 237 | 90 | 89 |
| 18 | | HFE | rs1800562 | CCTGGGGAAGAGCAGAGATATACGT[A/G] CC*AGG*TGGAGCACCCAGGCCTGGAT | 238 | 87 | 85 |
| 19 | | HFE | rs1800758 | GAGCTGAGAAAATCTATTGG*GGG*TT[A/G] AGAGGAGTGCCTGAGGAGGTAATTA | 239 | 69 | 86 |
| 20 | Phenylketo- nuria | PAH | rs62644499 | ACCTCGGCCCTTCTCAGTTCGCTAC[A/G] A*CCC*ATACACCCAAAGGATTGAGGT | 240 | 81 | 88 |
| 21 | | PAH | rs5030858 | TAGGAACTTTGCTGCCACAATA*CCT*[C/T] GGCCCTTCTCAGTTCGCTACGACCC | 241 | 75 | 85 |
| 22 | | PAH | rs62642936 | TTACAGGAAATTGGCCTTG*CCT*CTC[C/T] GGGTGCACCTGATGAATACATTGAA | 242 | 63 | 88 |

With respect to Table 12, CRISPR gRNAs were designed using MIT "Optimized CRISPR Design" tool to target 24 SNP loci from 8 top genetic disorders and cleavage positions were all less than 10 bases from SNPs to facilitate HDR in the real scenario of SNP correction. Top score gRNAs met condition above were chosen.

All publications, patents and patent applications mentioned in this Specification are indicative of the level of skill of those of ordinary skill in the art and are herein incorporated by reference to the same extent as if each individual publication, patent, or patent applications was specifically and individually indicated to be incorporated by reference.

What is claimed is:

1. A method of detecting off-target insertion of a donor nucleic acid molecule in the genome of a cell, the method comprising:
   (i) collecting nucleic acid from the cell to generate a nucleic acid sample;
   (i) fragmenting the nucleic acid present in the nucleic acid sample to generate a plurality of nucleic acid fragments;
   (iii) ligating a first nucleic acid adapter to termini of the plurality of nucleic acid fragments, thereby forming a plurality of adapted nucleic acid fragments;
   (iv) amplifying the plurality of adapted nucleic acid fragments by a first polymerase chain reaction procedure using a plurality of primers, wherein the plurality of primers comprise (a) a first primer that is capable of hybridizing to at least one of the nucleic acid adapters and (b) a second primer that is capable of hybridizing to the donor nucleic acid molecule and wherein the second primer contains a 5' terminal phosphate, thereby forming a plurality of amplified 5'-phosphate nucleic acid segments;
   (v) ligating a second nucleic acid adapter to the plurality of amplified 5'-phosphate nucleic acid segments, wherein the second nucleic acid adapter is ligated to the plurality of amplified 5'-phosphate nucleic acid segments, thereby forming a plurality of adapter nucleic acid segments;
   (vi) amplifying the plurality of adapter nucleic acid segments by a second polymerase chain reaction procedure, thereby forming a plurality of amplified adapter nucleic acid segments;
   (vii) attaching a separation agent to the plurality of amplified adapter nucleic acid segments, thereby forming a plurality of separation agent adapter nucleic acid segments;
   (viii) separating the separation agent adapter nucleic acid segments from nucleic acid molecules that are not attached to the separation agent, thereby generating a population of separation agent adapter nucleic acid segments; and
   (ix) sequencing individual members of the population of separation agent adapter nucleic acid segments, thereby detecting off-target insertion of the donor nucleic acid molecule into the genome of the cell.

2. The method of claim 1, wherein the plurality of nucleic acid fragments comprise chromosomal nucleic acid.

3. The method of claim 1, wherein the plurality of nucleic acid fragments are blunt-ended.

4. The method of claim 1, wherein the cell is a mammalian cell.

5. The method of claim 4, wherein the mammalian cell is a human cell.

6. The method of claim 1, wherein the fragmenting of the nucleic acid is performed by sonication or by contacting with a DNAse.

7. The method of claim 1, wherein the second nucleic acid adapter is a barcode adapter.

8. The method of claim 1, wherein the plurality of amplified adapter nucleic acid segments comprises a single strand tail on at least one end.

9. The method of claim 8, wherein the separation agent comprises a biotinylated tag oligonucleotide that is complementary to the single strand tail.

10. The method of claim 1, wherein the separating of the separation agent adapter nucleic acid segments from nucleic acid molecules that are not attached to the separation agent is mediated by the association of the separation agent adapter nucleic acid segments with a support.

11. The method of claim 1, wherein the sequencing is next generation sequencing.

* * * * *

UNITED STATES PATENT AND TRADEMARK OFFICE
CERTIFICATE OF CORRECTION

| | | |
|---|---|---|
| PATENT NO. | : 12,116,571 B2 | Page 1 of 1 |
| APPLICATION NO. | : 16/864445 | |
| DATED | : October 15, 2024 | |
| INVENTOR(S) | : Pei-Zhong Tang | |

It is certified that error appears in the above-identified patent and that said Letters Patent is hereby corrected as shown below:

In the Claims

Column 165, Claim 1, Lines 38-40, delete the text "(i) fragmenting the nucleic acid present in the nucleic acid sample to generate a plurality of nucleic acid fragments;" and insert the following text:
-- (ii) fragmenting the nucleic acid present in the nucleic acid sample to generate a plurality of nucleic acid fragments; --

Signed and Sealed this
Twenty-second Day of April, 2025

Coke Morgan Stewart
*Acting Director of the United States Patent and Trademark Office*